US009714401B2

(12) United States Patent
Frankenbach

(10) Patent No.: US 9,714,401 B2
(45) Date of Patent: Jul. 25, 2017

(54) PARTICLES FOR MALODOR REDUCTION

(71) Applicant: The Procter & Gamble Company, Cincinnati, OH (US)

(72) Inventor: Gayle Marie Frankenbach, Cincinnati, OH (US)

(73) Assignee: The Procter & Gamble Company, Cincinnati, OH (US)

(*) Notice: Subject to any disclaimer, the term of this patent is extended or adjusted under 35 U.S.C. 154(b) by 0 days.

(21) Appl. No.: 14/886,855

(22) Filed: Oct. 19, 2015

(65) Prior Publication Data

US 2017/0107455 A1 Apr. 20, 2017

(51) Int. Cl.

| | |
|---|---|
| ***C11D 3/00*** | (2006.01) |
| ***C11D 3/50*** | (2006.01) |
| ***A61L 2/23*** | (2006.01) |
| ***A61L 9/01*** | (2006.01) |

(52) U.S. Cl.
CPC .............. *C11D 3/0068* (2013.01); *A61L 2/23* (2013.01); *A61L 9/01* (2013.01); *C11D 3/50* (2013.01); *C11D 3/505* (2013.01)

(58) Field of Classification Search
None
See application file for complete search history.

(56) References Cited

U.S. PATENT DOCUMENTS

| | | | | |
|---|---|---|---|---|
| 3,716,498 | A | 2/1973 | Hall | |
| 4,234,627 | A | 11/1980 | Schilling | |
| 6,153,567 | A | 11/2000 | Hughes | |
| 6,656,923 | B1 | 12/2003 | Trinh et al. | |
| 7,186,680 | B2 | 3/2007 | Caswell et al. | |
| 7,786,027 | B2 | 8/2010 | Aouad et al. | |
| 7,867,968 | B1 | 1/2011 | Aouad | |
| 8,158,571 | B2 | 4/2012 | Alonso et al. | |
| 8,609,600 | B2 | 12/2013 | Warr et al. | |
| 9,347,022 | B1 * | 5/2016 | Frentzel | C11B 9/00 |
| 9,416,339 | B2 | 8/2016 | Bianchetti et al. | |
| 9,453,188 | B2 | 9/2016 | Brown et al. | |
| 2005/0112152 | A1 * | 5/2005 | Popplewell | A61K 8/11 424/401 |
| 2007/0269651 | A1 | 11/2007 | Denome et al. | |

(Continued)

FOREIGN PATENT DOCUMENTS

| | | | |
|---|---|---|---|
| DE | 10 2004 023720 | A1 | 12/2005 |
| GB | 2 450 727 | A | 1/2009 |

(Continued)

OTHER PUBLICATIONS

Non-Final Office Action for U.S. Appl. No. 14/865,010, dated Nov. 4, 2016, 14 pages.

(Continued)

*Primary Examiner* — Aradhana Sasan
(74) *Attorney, Agent, or Firm* — Gary J. Foose

(57) ABSTRACT

A composition including a plurality of particles, wherein the particles include: about 30% to about 95% by weight of a carrier; about 0.1% to about 30% by weight of a perfume; and about 0.00025% to about 30% by weight of a malodor agent; wherein the malodor agent comprises one or more malodor reduction materials having a Blocker Index of less than 3 or a Blocker Index average of 3 to about 0.001; and wherein each of the particles has a mass between about 0.1 mg to about 5 g.

19 Claims, 2 Drawing Sheets

(56) References Cited

U.S. PATENT DOCUMENTS

| | | | | |
|---|---|---|---|---|
| 2008/0003245 | A1 | 1/2008 | Kroepke et al. | |
| 2008/0176780 | A1 | 7/2008 | Warr et al. | |
| 2009/0215664 | A1 | 8/2009 | Raehse | |
| 2011/0059179 | A1* | 3/2011 | Shefer | A61K 8/0279 424/490 |
| 2011/0098209 | A1 | 4/2011 | Smets et al. | |
| 2011/0245134 | A1 | 10/2011 | Smets et al. | |
| 2016/0090556 | A1 | 3/2016 | Frankenbach et al. | |
| 2016/0090558 | A1* | 3/2016 | Frankenbach | C11B 9/0015 424/455 |
| 2016/0369211 | A1* | 12/2016 | Dykstra | C11B 9/00 |

FOREIGN PATENT DOCUMENTS

| | | | |
|---|---|---|---|
| WO | WO 96/04937 | A1 | 2/1996 |
| WO | WO 00/30691 | A1 | 6/2000 |
| WO | WO 2004/020566 | | 3/2004 |
| WO | WO 2008/061658 | A1 | 5/2008 |
| WO | WO 2009/118349 | A1 | 10/2009 |
| WO | WO 2012/136651 | A1 | 10/2012 |

OTHER PUBLICATIONS

Non-Final Office Action for U.S. Appl. No. 14/865,412, dated Nov. 4, 2016, 17 pages.

Partial International Search Report for International Application Serial No. PCT/US2016/057573, mailed Mar. 10, 2017, 24 pages.

International Search Report for International Application Serial No. PCT/US2015/052090, mailed Jan. 19, 2016, 13 pages.

International Search Report for International Application Serial No. PCT/US2015/052225, mailed Jan. 20, 2016, 15 pages.

U.S. Appl. No. 15/064,171, filed Mar. 8, 2016, Valdivieso et al.

U.S. Appl. No. 15/421,481, filed Feb. 1, 2017, Frankenbach et al.

U.S. Appl. No. 15/421,642, filed Feb. 1, 2017, Frankenbach et al.

* cited by examiner

PARTICLES FOR MALODOR REDUCTION

FIELD OF THE INVENTION

Particles including malodor reduction compositions and methods of using such particles for managing malodor in laundry articles.

BACKGROUND OF THE INVENTION

Laundry articles having significant malodors is a problem that continues to face consumers.

People enjoy wearing garments that smell fresh and clean. Maintaining a full wardrobe that is populated with a sufficient number of garments that are fresh and clean can be a burden on many people because they are too busy to regularly spend their time taking care of their laundry and do not wish to pay for a service that will take care of their laundry. Further, many people have garments that comprise fabrics or appurtenances that may not be durable enough to withstand multiple wearing, washing, and drying cycles without a the appearance or function of the garment being degraded.

To compensate for these problems, many people wear garments multiple times before they launder the garment. In many circumstances, wearing a garment multiple times between washings or dry cleaning is fine. A shirt, pants, or skirt may be worn multiple times between washings if the garment has not picked up any visible stains, the person has not perspired appreciably, the person has not been in an environment having odiferous air such as a smoky environment, restaurant selling strong smelling foods, or the person has not contacted strongly smelling objects such as a pet. However, the typical experience for most people is that they do perspire, are in environments where strong odors are present, or come into contact with smelly pets and the like. So even if a person avoids acquiring a stain or smudge on their garment during wear, it is probable that the garment has picked up some odors during wear.

Sometimes laundered garments are stored in a closet for weeks or months prior to being worn. By the time the garment is worn, the scent of the garment acquired during laundering has worn off. Depending on the environment in which the garment is stored, the garment may have a neutral or no odor or may have a musty, moldy, stale malodor. The malodors associated with long term storage of garments can negatively impact the experience of the person, and those around her, who chooses to wear a garment that has been stored for an appreciable period of time.

A similar situation arises when a person wants to continue to wear an article of clothing that has been worn earlier in the day. For example, after getting off work, a person may want to go out with friends to a restaurant, pub, or movie. After wearing the clothing during the work day, the clothing may have a neutral or non-noticeable odor, or even worse may have an unattractive odor that was acquired during the course of the day. The neutral or even negative malodor can have a negative impact on the psyche of the wearer and form a negative impression upon the people around the wearer of such a garment.

Similar problems can be associated with storing laundry articles that have been worn. With wear, clothing can become sweaty and smelly. Prior to laundering, the soiled laundry article might be stored in a gym bag, trunk of the car, laundry hamper, or pile of clothing. Over time, the level of malodor can increase to a degree such that it becomes repulsive for the consumer and those around her. Further, the malodor may be experienced by the consumer when she handles the soiled laundry prior to washing.

Common malodors and sources thereof can include amine-based malodors (e.g. fish and urine), thiol and sulfide-based malodors (e.g. garlic and onion), $C_2$-$C_{12}$ carboxylic acid based malodors (e.g. body and pet odor), indole based malodors (e.g. fecal and bad breath), short chain fatty aldehyde based malodors (e.g. grease) and geosmin based malodors (e.g. mold/mildew). The typical technical approach for managing malodors is to apply a malodor reduction ingredient or to mask the malodor with perfume. Unfortunately, malodor control technologies typically cover up the malodor with a stronger scent and thus interfere with the scent of the perfumed or unperfumed laundry article that is treated with the malodor control technology. Thus, limited nature of the current malodor control technologies is constraining.

With these limitations in mind, there is a continuing unaddressed need for technologies for managing malodors in laundered and soiled laundry articles.

SUMMARY OF THE INVENTION

A composition comprising a plurality of particles, wherein said particles comprise: about 30% to about 95% by weight of a carrier; about 0.1% to about 30% by weight of a perfume; and about 0.00025% to about 30% by weight of a malodor agent; wherein said malodor agent comprises from about 1 to about 30 malodor reduction materials having a Blocker Index of less than 3 or a Blocker Index average of 3 to about 0.001; and wherein each of said particles has a mass between about 0.1 mg to about 5 g.

DETAILED DESCRIPTION OF THE INVENTION

Figure 1:
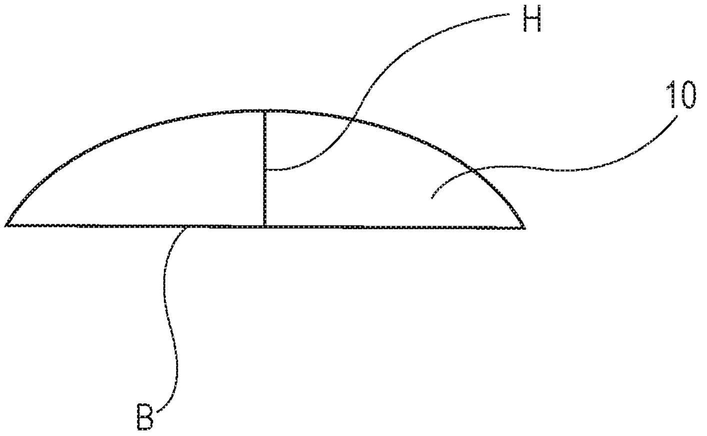
FIG. 1 is a particle.

As used herein "MORV" is the calculated malodor reduction value for a subject material. A material's MORV indicates such material's ability to decrease or even eliminate the perception of one or more malodors. For purposes of the present application, a material's MORV is calculated in accordance with method found in the test methods section of the present application.

As used herein, the term "perfume" does not include malodor reduction materials. Thus, the perfume portion of a composition does not include, when determining the perfume's composition, any malodor reduction materials found in the composition as such malodor reduction materials are described herein. In short, if a material has a malodor reduction value "MORV" that is within the range of the MORV recited in the subject claim, such material is a malodor reduction material for purposes of such claim.

As used herein, "malodor" refers to compounds generally offensive or unpleasant to most people, such as the complex odors associated with bowel movements.

As used herein, "odor blocking" refers to the ability of a compound to dull the human sense of smell.

Unless otherwise noted, all component or composition levels are in reference to the active portion of that component or composition, and are exclusive of impurities, for example, residual solvents or by-products, which may be present in commercially available sources of such components or compositions.

All percentages and ratios are calculated by weight unless otherwise indicated. All percentages and ratios are calculated based on the total composition unless otherwise indicated.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Malodor Reduction Materials

A non-limiting set of suitable malodor reduction materials are provided in the tables below. For ease of use, each material in Tables 1-3 is assigned a numerical identifier which is found in the column for each table that is designated Number. Table 4 is a subset of Table 1, Table 5 is a subset of Table 2 and Table 6 is a subset of Table 3and there for Tables 4, 5and 6 each use the same numerical identifier as found, respectively, in Tables 1-3.

| Codes |
|---|
| A = Vapor Pressure > 0.1 torr |
| B = Vapor Pressure is between 0.01 torr and 0.1 torr |
| C = logP < 3 |
| D = logP > 3 |
| E = Probability of Ingredient Color Instability = 0% |
| F = Probability of Ingredient Color Instability < 71% |
| G = Odor Detection Threshold less than p.ol = 8 |
| H = Odor Detection Threshold greater than p.ol = 8 |
| I = Melamine formaldehyde PMC Headspace Response Ratio greater than or equal to 10 |
| J = Melamine formaldehyde PMC leakage less than or equal to 5% |
| K = Log of liquid dish neat product liquid-air partition coefficient greater than or equal to −7 |
| L = Log of liquid dish neat product liquid-air partition coefficient greater than or equal to −5 |

TABLE 1

List of materials with at least one MORV from 1 to 5

| Number | Material Name | CAS Number | Comment Code |
|---|---|---|---|
| 1 | 2-ethylhexyl (Z)-3-(4-methoxyphenyl)acrylate | 5466-77-3 | DEFHJ |
| 2 | 2,4-dimethyl-2-(5,5,8,8-tetramethyl-5,6,7,8-tetrahydronaphthalen-2-yl)-1,3-dioxolane | 131812-67-4 | DFHJ |
| 3 | 1,1-dimethoxynon-2-yne | 13257-44-8 | ACEFHJK |
| 4 | para-Cymen-8-ol | 1197-01-9 | BCGIJK |
| 7 | 3-methoxy-7,7-dimethyl-10-methylenebicyclo[4.3.1]decane | 216970-21-7 | BDEFHJK |
| 9 | Methoxycyclododecane | 2986-54-1 | DEFHJK |
| 10 | 1,1-dimethoxycyclododecane | 950-33-4 | DEFHJK |
| 11 | (Z)-tridec-2-enenitrile | 22629-49-8 | DEFHJK |
| 13 | Oxybenzone | 131-57-7 | DEFGJ |
| 14 | Oxyoctaline formate | 65405-72-3 | DFHJK |
| 16 | 4-methyl-1-oxaspiro[5.5]undecan-4-ol | 57094-40-3 | CFGIJK |
| 17 | 7-methyl-2H-benzo[b][1,4]dioxepin-3(4H)-one | 28940-11-6 | CGIK |
| 18 | 1,8-dioxacycloheptadecan-9-one | 1725-01-5 | DGJ |

TABLE 1-continued

List of materials with at least one MORV from 1 to 5

| Number | Material Name | CAS Number | Comment Code |
|---|---|---|---|
| 21 | 4-(tert-pentyl)cyclohexan-1-one | 16587-71-6 | ADFGIJKL |
| 22 | o-Phenyl anisol | 86-26-0 | DEFHJK |
| 23 | 3a,5,6,7,8,8b-hexahydro-2,2,6,6,7,8,8-heptamethyl-4H-indeno(4,5-d)-1,3-dioxole | 823178-41-2 | DEFHJK |
| 25 | 7-isopropyl-8,8-dimethyl-6,10-dioxaspiro[4.5]decane | 62406-73-9 | BDEFHIJK |
| 28 | Octyl 2-furoate | 39251-88-2 | DEFHJK |
| 29 | Octyl acetate | 112-14-1 | BDEFHJKL |
| 30 | octanal propylene glycol acetal | 74094-61-4 | BDEFHJKL |
| 31 | Octanal | 124-13-0 | ACHIKL |
| 32 | Octanal dimethyl acetal | 10022-28-3 | ACEFGJKL |
| 33 | Myrcene | 123-35-3 | ADEFGIKL |
| 34 | Myrcenol | 543-39-5 | BCEFGIJK |
| 35 | Myrcenyl acetate | 1118-39-4 | ADEFGJK |
| 36 | Myristaldehyde | 124-25-4 | DFHJK |
| 37 | Myristicine | 607-91-0 | CGJK |
| 38 | Myristyl nitrile | 629-63-0 | DEFHJK |
| 39 | 2,2,6,8-tetramethyl-1,2,3,4,4a,5,8,8a-octahydronaphthalen-1-ol | 103614-86-4 | DEFHIJK |
| 42 | Ocimenol | 5986-38-9 | BCHIJK |
| 43 | Ocimenol | 28977-58-4 | BCHIJK |
| 47 | Nopyl acetate | 128-51-8 | DEFHJK |
| 48 | Nootkatone | 4674-50-4 | DHJK |
| 49 | Nonyl alcohol | 143-08-8 | BDEFGIJKL |
| 50 | Nonaldehyde | 124-19-6 | ADHIKL |
| 52 | 12-methyl-14-tetradec-9-enolide | 223104-61-8 | DFHJK |
| 57 | N-ethyl-p-menthane-3-carboxamide | 39711-79-0 | DEFGIJK |
| 61 | 1-(3-methylbenzofuran-2-yl)ethan-1-one | 23911-56-0 | CEFHIK |
| 62 | 2-methoxynaphthalene | 93-04-9 | BDEFHK |
| 63 | Nerolidol | 7212-44-4 | DEFHJK |
| 64 | Nerol | 106-25-2 | BCHIK |
| 65 | 1-ethyl-3-methoxytricyclo[2.2.1.02,6]heptane | 31996-78-8 | ACEFHIJKL |
| 67 | Methyl (E)-non-2-enoate | 111-79-5 | ADEFHJKL |
| 68 | 10-isopropyl-2,7-dimethyl-1-oxaspiro[4.5]deca-3,6-diene | 89079-92-5 | BDEFHIJK |
| 69 | 2-(2-(4-methylcyclohex-3-en-1-yl)propyl)cyclopentan-1-one | 95962-14-4 | DHJK |
| 70 | Myrtenal | 564-94-3 | ACFHIJKL |
| 71 | (E)-4-(2,2,3,6-tetramethylcyclohexyl)but-3-en-2-one | 54992-90-4 | BDEFHIJK |
| 74 | Myraldyl acetate | 53889-39-7 | DHJK |
| 75 | Musk tibetine | 145-39-1 | DHIJ |
| 76 | 1,7-dioxacycloheptadecan-8-one | 3391-83-1 | DGJ |
| 77 | Musk ketone | 81-14-1 | DHJ |
| 78 | Musk ambrette | 83-66-9 | DHIJ |
| 79 | 3-methylcyclopentadecan-1-one | 541-91-3 | DEFHJK |
| 80 | (E)-3-methylcyclopentadec-4-en-1-one | 82356-51-2 | DHJK |
| 82 | 3-methyl-4-phenylbutan-2-ol | 56836-93-2 | BCEFHIK |
| 83 | 1-(4-isopropylcyclohexyl)ethan-1-ol | 63767-86-2 | BDEFHIJK |
| 85 | Milk Lactone | 72881-27-7 | DEFHJK |
| 91 | Methyl octine carbonate | 111-80-8 | BDEFHKL |
| 92 | Methyl octyl acetaldehyde | 19009-56-4 | ADFHJKL |
| 93 | 6,6-dimethoxy-2,5,5-trimethylhex-2-ene | 67674-46-8 | ACHIJKL |
| 98 | Methyl phenylethyl carbinol | 2344-70-9 | BCEFHIK |
| 100 | Methyl stearate | 112-61-8 | DEFHJ |
| 101 | Methyl nonyl acetaldehyde dimethyl acetal | 68141-17-3 | BDEFHJK |
| 102 | Methyl nonyl ketone | 112-12-9 | BDFHJKL |
| 103 | Methyl nonyl acetaldehyde | 110-41-8 | BDFHJK |
| 104 | Methyl myristate | 124-10-7 | DEFHJK |
| 105 | Methyl linoleate | 112-63-0 | DEFHJ |
| 106 | Methyl lavender ketone | 67633-95-8 | CFHJK |
| 108 | Methyl isoeugenol | 93-16-3 | ACEFHK |
| 109 | Methyl hexadecanoate | 112-39-0 | DEFHJK |
| 110 | Methyl eugenol | 93-15-2 | ACEFHK |
| 112 | Methyl epijasmonate | 1211-29-6 | CHJK |
| 113 | Methyl dihydrojasmonate | 24851-98-7 | DFHJK |
| 114 | Methyl diphenyl ether | 3586-14-9 | DEFHJK |
| 117 | Methyl cinnamate | 103-26-4 | BCEFHK |

TABLE 1-continued

List of materials with at least one MORV from 1 to 5

| Number | Material Name | CAS Number | Comment Code |
|---|---|---|---|
| 119 | Methyl chavicol | 140-67-0 | ADEFHK |
| 120 | Methyl beta-naphthyl ketone | 93-08-3 | CEFHK |
| 122 | Methyl 2-octynoate | 111-12-6 | ACEFHKL |
| 123 | Methyl alpha-cyclogeranate | 28043-10-9 | ACHIJKL |
| 126 | Methoxycitronellal | 3613-30-7 | ACFGIJK |
| 128 | Menthone 1,2-glycerol ketal (racemic) | 67785-70-0 | CEFHJ |
| 130 | Octahydro-1H-4,7-methanoindene-1-carbaldehyde | 30772-79-3 | BCFHIJKL |
| 134 | 3-(3-(tert-butyl)phenyl)-2-methylpropanal | 62518-65-4 | BDHJK |
| 135 | (E)-4-(4,8-dimethylnona-3,7-dien-1-yl)pyridine | 38462-23-6 | DEFHJK |
| 137 | (E)-trideca-3,12-dienenitrile | 134769-33-8 | DEFHJK |
| 140 | 2,2-dimethyl-3-(m-tolyl)propan-1-ol | 103694-68-4 | CEFHIJK |
| 141 | 2,4-dimethyl-4,4a,5,9b-tetrahydroindeno[1,2-d][1,3]dioxine | 27606-09-3 | CEFHJK |
| 142 | Maceal | 67845-30-1 | BDFHJK |
| 143 | 4-(4-hydroxy-4-methylpentyl)cyclohex-3-ene-1-carbaldehyde | 31906-04-4 | CHJ |
| 145 | 1-Limonene | 5989-54-8 | ADEFGIJKL |
| 146 | (Z)-3-hexen-1-yl-2-cyclopenten-1-one | 53253-09-1 | BDHK |
| 148 | Linalyl octanoate | 10024-64-3 | DEFHJ |
| 149 | Linalyl isobutyrate | 78-35-3 | BDHJK |
| 152 | Linalyl benzoate | 126-64-7 | DFHJ |
| 153 | Linalyl anthranilate | 7149-26-0 | DFHJ |
| 155 | Linalool oxide (furanoid) | 60047-17-8 | BCHIJK |
| 156 | linalool oxide | 1365-19-1 | CGIJK |
| 158 | (2Z,6E)-3,7-dimethylnona-2,6-dienenitrile | 61792-11-8 | BDEFHJK |
| 159 | 3-(4-methylcyclohex-3-en-1-yl)butanal | 6784-13-0 | ACFHIJK |
| 161 | (2,5-dimethyl-1,3-dihydroinden-2-yl)methanol | 285977-85-7 | CEFHJK |
| 162 | 3-(4-(tert-butyl)phenyl)-2-methylpropanal | 80-54-6 | BDHJK |
| 167 | (E)-1-(1-methoxypropoxy)hex-3-ene | 97358-54-8 | ACEFGJKL |
| 168 | Leaf acetal | 88683-94-7 | ACEFGJKL |
| 170 | 1-Carveol | 2102-58-1 | BCHIJK |
| 174 | Lauryl alcohol | 112-53-8 | DEFGJK |
| 175 | Lauryl acetate | 112-66-3 | DEFHJK |
| 176 | Lauric acid | 143-07-7 | DEFHJ |
| 177 | Lactojasmone | 7011-83-8 | BDEFHIJKL |
| 178 | Lauraldehyde | 112-54-9 | BDFHJK |
| 179 | 3,6-dimethylhexahydrobenzofuran-2(3H)-one | 92015-65-1 | BCEFHIJKL |
| 182 | 4-(1-ethoxyvinyl)-3,3,5,5-tetramethylcyclohexan-1-one | 36306-87-3 | BDFHIJK |
| 183 | Khusimol | 16223-63-5 | CEFHJK |
| 184 | 5-(sec-butyl)-2-(2,4-dimethylcyclohex-3-en-1-yl)-5-methyl-1,3-dioxane | 117933-89-8 | DEFHJ |
| 185 | (1-methyl-2-((1,2,2-trimethylbicyclo[3.1.0]hexan-3-yl)methyl)cyclopropyl)methanol | 198404-98-7 | DEFHJK |
| 186 | 2-propylheptanenitrile | 208041-98-9 | ADEFHIJKL |
| 187 | (E)-6-(pent-3-en-1-yl)tetrahydro-2H-pyran-2-one | 32764-98-0 | BCFHIKL |
| 189 | 2-hexylcyclopentan-1-one | 13074-65-2 | BDFHJKL |
| 190 | 2-methyl-4-phenyl-1,3-dioxolane | 33941-99-0 | BCEFGIK |
| 192 | 2,6,9,10-tetramethyl-1-oxaspiro(4.5)deca-3,6-diene | 71078-31-4 | BDEFHIJK |
| 193 | Isopulegol | 89-79-2 | BCEFHIJKL |
| 195 | Isopropyl palmitate | 142-91-6 | DEFHJ |
| 196 | Isopropyl myristate | 110-27-0 | DEFHJK |
| 197 | Isopropyl dodecanoate | 10233-13-3 | DEFHJK |
| 199 | Isopimpinellin | 482-27-9 | CFGJ |
| 206 | Iso3-methylcyclopentadecan-1-one | 3100-36-5 | DEFGJK |
| 208 | Isomenthone | 491-07-6 | ADEFGIJKL |
| 209 | Isojasmone | 95-41-0 | BDFHJKL |
| 210 | Isomenthone | 36977-92-1 | ADEFGIJKL |
| 211 | Isohexenyl cyclohexenyl carboxaldehyde | 37677-14-8 | DFHJK |

TABLE 1-continued

List of materials with at least one MORV from 1 to 5

| Number | Material Name | CAS Number | Comment Code |
|---|---|---|---|
| 212 | Isoeugenyl benzyl ether | 120-11-6 | DFHJ |
| 215 | 1-((2S,3S)-2,3,8,8-tetramethyl-1,2,3,4,5,6,7,8-octahydronaphthalen-2-yl)ethan-1-one | 54464-57-2 | DHJK |
| 218 | Isocyclocitral | 1335-66-6 | ACFHIJKL |
| 221 | Isobutyl quinoline | 65442-31-1 | DEFHJK |
| 227 | Isobornylcyclohexanol | 68877-29-2 | DEFHJK |
| 228 | Isobornyl propionate | 2756-56-1 | BDEFHIJK |
| 229 | Isobornyl isobutyrate | 85586-67-0 | BDEFHIJK |
| 230 | Isobornyl cyclohexanol | 66072-32-0 | DEFHJK |
| 231 | Isobornyl acetate | 125-12-2 | ADEFHIJKL |
| 233 | Isobergamate | 68683-20-5 | DEFHJK |
| 234 | Isoamyl undecylenate | 12262-03-2 | DEFHJK |
| 238 | Isoamyl laurate | 6309-51-9 | DEFHJK |
| 242 | Isoambrettolide | 28645-51-4 | DGJ |
| 243 | Irisnitrile | 29127-83-1 | ADEFHKL |
| 244 | Indolene | 68527-79-7 | DEFHJ |
| 246 | Indol/Hydroxycitronellal Schiff base | 67801-36-9 | DEFHJ |
| 247 | 4,4a,5,9b-tetrahydroindeno[1,2-d][1,3]dioxine | 18096-62-3 | BCEFGJK |
| 249 | Hydroxy-citronellol | 107-74-4 | CEFGIJK |
| 252 | 2-cyclododecylpropan-1-ol | 118562-73-5 | DEFHJK |
| 253 | Hydrocitronitrile | 54089-83-7 | CEFHJK |
| 254 | Hydrocinnamyl alcohol | 122-97-4 | BCEFHIK |
| 256 | Hydratropaldehyde dimethyl acetal | 90-87-9 | ACEFHJK |
| 259 | 5-ethyl-4-hydroxy-2-methylfuran-3(2H)-one | 27538-09-6 | CFGIK |
| 260 | 2,3-dihydro-3,3-dimethyl-1H-indene-5-propanal | 173445-44-8 | DHJK |
| 261 | 3-(3,3-dimethyl-2,3-dihydro-1H-inden-5-yl)propanal | 173445-65-3 | DHJK |
| 263 | Hexyl octanoate | 1117-55-1 | DEFHJK |
| 267 | Hexyl hexanoate | 6378-65-0 | DEFHJKL |
| 269 | Hexyl cinnamic aldehyde | 101-86-0 | DHJ |
| 271 | Hexyl benzoate | 6789-88-4 | DEFHJK |
| 274 | Hexenyl tiglate | 84060-80-0 | BDEFHJK |
| 276 | (E)-3,7-dimethylocta-2,6-dien-1-yl palmitate | 3681-73-0 | DEFHJ |
| 277 | Hexadecanolide | 109-29-5 | DEFGJK |
| 278 | 2-butyl-4,4,6-trimethyl-1,3-dioxane | 54546-26-8 | ADEFHIJKL |
| 280 | Ethyl (1R,2R,3R,4R)-3-isopropylbicyclo[2.2.1]hept-5-ene-2-carboxylate | 116126-82-0 | BDEFHIJK |
| 281 | 3a,4,5,6,7,7a-hexahydro-1H-4,7-methanoinden-6-yl acetate | 5413-60-5 | CEFGJK |
| 285 | 2-(1-(3,3-dimethylcyclohexyl)ethoxy)-2-methylpropyl propionate | 141773-73-1 | DEFHJ |
| 286 | Heliotropine diethyl acetal | 40527-42-2 | CEFGJ |
| 288 | Helional | 1205-17-0 | CHJK |
| 289 | (E)-oxacyclohexadec-13-en-2-one | 111879-80-2 | DGJK |
| 290 | Gyrane | 24237-00-1 | ADEFHIJKL |
| 292 | Guaiol | 489-86-1 | DEFHJK |
| 293 | 1-(2,6,6-trimethylcyclohex-2-en-1-yl)pentan-3-one | 68611-23-4 | DHJK |
| 294 | Ethyl 2-ethyl-6,6-dimethylcyclohex-2-ene-1-carboxylate | 57934-97-1 | BDEFHIJK |
| 295 | Germacrene B | 15423-57-1 | DEFHJK |
| 296 | Germacrene D | 23986-74-5 | DEFHJK |
| 300 | Geranyl phenylacetate | 102-22-7 | DFHJ |
| 301 | Geranyl phenyl acetate | 71648-43-6 | DFHJ |
| 303 | Geranyl linalool | 1113-21-9 | DFHJ |
| 307 | Geranyl cyclopentanone | 68133-79-9 | DHJK |
| 316 | gamma-Undecalactone (racemic) | 104-67-6 | DEFHJKL |
| 317 | gamma-Terpinyl acetate | 10235-63-9 | BDHJK |
| 318 | gamma-Terpineol | 586-81-2 | BCGIJK |
| 321 | gamma-Nonalactone | 104-61-0 | BCEFHIKL |
| 322 | gamma-Muurolene | 30021-74-0 | DEFHJKL |
| 323 | gamma-(E)-6-(pent-3-en-1-yl)tetrahydro-2H-pyran-2-one | 63095-33-0 | BCEFHKL |
| 324 | gamma-Ionone | 79-76-5 | BDEFHIJK |
| 325 | gamma-Himachalene | 53111-25-4 | BDEFHJKL |
| 328 | gamma-Gurjunene | 22567-17-5 | DEFHJKL |
| 329 | gamma-Eudesmol | 1209-71-8 | DFHJK |
| 330 | gamma-Dodecalactone | 2305-05-7 | DEFHJK |

TABLE 1-continued

List of materials with at least one MORV from 1 to 5

| Number | Material Name | CAS Number | Comment Code |
|---|---|---|---|
| 331 | gamma-Damascone | 35087-49-1 | BDEFHIJK |
| 332 | gamma-Decalactone | 706-14-9 | BDEFHIJKL |
| 333 | gamma-Cadinene | 39029-41-9 | DEFHJKL |
| 334 | 1-(3,3-dimethylcyclohexyl)pent-4-en-1-one | 56973-87-6 | BDEFHJK |
| 335 | 4,6,6,7,8,8-hexamethyl-1,3,4,6,7,8-hexahydrocyclopenta[g]isochromene | 1222-05-5 | DEFHJK |
| 336 | Furfuryl octanoate | 39252-03-4 | DEFHJK |
| 338 | Furfuryl hexanoate | 39252-02-3 | CEFHJK |
| 339 | Furfuryl heptanoate | 39481-28-2 | CEFHJK |
| 342 | 2-methyldecanenitrile | 69300-15-8 | BDEFHJKL |
| 343 | 8,8-dimethyl-3a,4,5,6,7,7a-hexahydro-1H-4,7-methanoinden-6-yl propionate | 76842-49-4 | DEFHJK |
| 344 | Ethyl (3aR,4S,7R,7aR)-octahydro-3aH-4,7-methanoindene-3a-carboxylate | 80657-64-3 | DEFHIJK |
| 347 | Diethyl cyclohexane-1,4-dicarboxylate | 72903-27-6 | CEFHJK |
| 349 | (6-isopropyl-9-methyl-1,4-dioxaspiro[4.5]decan-2-yl)methanol | 63187-91-7 | CEFHJ |
| 350 | 2-isobutyl-4-methyltetrahydro-2H-pyran-4-ol | 63500-71-0 | BCEFHIJK |
| 352 | Undec-10-enenitrile | 53179-04-7 | BDEFHJK |
| 353 | (Z)-6-ethylideneoctahydro-2H-5,8-methanochromen-2-one | 69486-14-2 | CEFGJK |
| 356 | 3-(2-ethylphenyl)-2,2-dimethylpropanal | 67634-15-5 | BDHJK |
| 358 | (E)-4,8-dimethyldeca-4,9-dienal | 71077-31-1 | BDFHJK |
| 359 | (E)-4-((3aR,4R,7R,7aR)-1,3a,4,6,7,7a-hexahydro-5H-4,7-methanoinden-5-ylidene)-3-methylbutan-2-ol | 501929-47-1 | DEFHJK |
| 360 | 8,8-dimethyl-3a,4,5,6,7,7a-hexahydro-1H-4,7-methanoinden-6-yl acetate | 171102-41-3 | DEFHJK |
| 361 | 3-(4-ethylphenyl)-2,2-dimethylpropanenitrile | 134123-93-6 | DEFHJK |
| 362 | 2-heptylcyclopentan-1-one | 137-03-1 | DFHJKL |
| 363 | 1-ethoxyethoxy Cyclododecane | 389083-83-4 | DEFHJK |
| 364 | 3-cyclohexene-1-carboxylic acid, 2,6,6-trimethyl-, methyl ester | 815580-59-7 | ACHIJKL |
| 368 | Farnesyl acetate | 29548-30-9 | DEFHJK |
| 369 | Farnesol | 4602-84-0 | DEFHJK |
| 370 | Oxacyclohexadecan-2-one | 106-02-5 | DEFGJK |
| 371 | 1-cyclopentadec-4-en-1-one | 14595-54-1 | DEFGJK |
| 372 | 1-cyclopentadec-4-en-1-one | 35720-57-1 | DEFGJK |
| 373 | 2-methoxy-4-(4-methylenetetrahydro-2H-pyran-2-yl)phenol | 128489-04-3 | CGJ |
| 374 | Eugenyl acetate | 93-28-7 | CFHJK |
| 375 | Eugenol | 97-53-0 | CHIK |
| 377 | Ethylmethylphenylglycidate | 77-83-8 | CFHJK |
| 378 | Ethylene brassylate | 105-95-3 | DFGJ |
| 381 | Ethyl undecylenate | 692-86-4 | DEFHJK |
| 385 | Ethyl palmitate | 628-97-7 | DEFHJ |
| 386 | Ethyl nonanoate | 123-29-5 | BDEFHJKL |
| 388 | Ethyl myristate | 124-06-1 | DEFHJK |
| 390 | Ethyl linalool | 10339-55-6 | BCEFHJK |
| 391 | Ethyl laurate | 106-33-2 | DEFHJK |
| 394 | Ethyl hexyl ketone | 925-78-0 | ADFHIKL |
| 397 | Ethyl decanoate | 110-38-3 | BDEFHJK |
| 398 | Ethyl gamma-Safranate | 35044-57-6 | ADHIJK |
| 407 | Ethyl 3-phenylglycidate | 121-39-1 | CGJK |
| 413 | 6-ethyl-2,10,10-trimethyl-1-oxaspiro[4.5]deca-3,6-diene | 79893-63-3 | BDEFHIJK |
| 414 | Elemol | 639-99-6 | DEFHJK |
| 415 | (2-(1-ethoxyethoxy)ethyl)benzene | 2556-10-7 | BCEFHJK |
| 416 | (E)-3-methyl-5-(2,2,3-trimethylcyclopent-3-en-1-yl)pent-4-en-2-ol | 67801-20-1 | DHJK |
| 417 | d-xylose | 58-86-6 | CGIJ |
| 418 | (E)-4-((3aS,7aS)-octahydro-5H-4,7-methanoinden-5-ylidene)butanal | 30168-23-1 | DFHJK |
| 421 | Dodecanal dimethyl acetal | 14620-52-1 | DEFHJK |

TABLE 1-continued

List of materials with at least one MORV from 1 to 5

| Number | Material Name | CAS Number | Comment Code |
|---|---|---|---|
| 424 | d-Limonene | 5989-27-5 | ADEFGIJKL |
| 425 | Dipropylene Glycol | 25265-71-8 | CEFGIK |
| 426 | Dispirone | 83863-64-3 | BDEFHJK |
| 428 | Diphenyloxide | 101-84-8 | BDEFHK |
| 429 | Diphenylmethane | 101-81-5 | DEFGK |
| 432 | Dimethyl benzyl carbinyl butyrate | 10094-34-5 | DEFHJK |
| 436 | 2,6-dimethyloct-7-en-4-one | 1879-00-1 | ADEFHIJKL |
| 441 | Octahydro-1H-4,7-methanoinden-5-yl acetate | 64001-15-6 | DEFHJKL |
| 444 | Dihydrocarveol acetate | 20777-49-5 | BDEFHIJK |
| 445 | Dihydrocarveol | 619-01-2 | BCEFHIJKL |
| 449 | Dihydro Linalool | 18479-51-1 | BCEFGIJKL |
| 450 | Dihydro Isojasmonate | 37172-53-5 | DHJK |
| 453 | Dibutyl sulfide | 544-40-1 | ADEFHIKL |
| 457 | Dibenzyl | 103-29-7 | DEFGJK |
| 459 | delta-Undecalactone | 710-04-3 | DEFHJKL |
| 461 | delta-Elemene | 20307-84-0 | BDEFHJK |
| 462 | delta-Guaiene | 3691-11-0 | DEFHJKL |
| 463 | delta-Dodecalactone | 713-95-1 | DEFHJK |
| 464 | delta-Decalactone | 705-86-2 | BDEFHIJKL |
| 465 | delta-Cadinene | 483-76-1 | DEFHJKL |
| 466 | delta-damascone | 57378-68-4 | ADHIJK |
| 467 | delta-Amorphene | 189165-79-5 | DEFHJKL |
| 468 | delta-3-Carene | 13466-78-9 | ADEFGIJKL |
| 470 | Decylenic alcohol | 13019-22-2 | BDEFHJK |
| 471 | Decyl propionate | 5454-19-3 | DEFHJK |
| 473 | Decanal diethyl acetal | 34764-02-8 | DEFHJK |
| 474 | Decahydro-beta-naphthol | 825-51-4 | BCEFGIK |
| 475 | 1-cyclohexylethyl (E)-but-2-enoate | 68039-69-0 | BDFHJK |
| 478 | 3-(4-isopropylphenyl)-2-methylpropanal | 103-95-7 | BDFHJK |
| 479 | Cyclotetradecane | 295-17-0 | DEFGJKL |
| 480 | Cyclopentadecanone | 502-72-7 | DEFGJK |
| 482 | Cyclohexyl salicylate | 25485-88-5 | DFGJ |
| 484 | 3a,4,5,6,7,7a-hexahydro-1H-4,7-methanoinden-6-yl butyrate | 113889-23-9 | DEFHJK |
| 485 | Cyclic ethylene dodecanedioate | 54982-83-1 | DFGJ |
| 486 | 8,8-dimethyl-1,2,3,4,5,6,7,8-octahydronaphthalene-2-carbaldehyde | 68991-97-9 | DHJK |
| 487 | 3a,4,5,6,7,7a-hexahydro-1H-4,7-methanoinden-5-yl isobutyrate | 67634-20-2 | DEFHJK |
| 488 | Curzerene | 17910-09-7 | DHJK |
| 491 | Cumic alcohol | 536-60-7 | CHIJK |
| 493 | Coumarone | 1646-26-0 | BCEFHIK |
| 497 | 2-(3-phenylpropyl)pyridine | 2110-18-1 | CEFHJK |
| 498 | Dodecanenitrile | 2437-25-4 | DEFHJK |
| 501 | (E)-cycloheptadec-9-en-1-one | 542-46-1 | DEFGJ |
| 502 | Citryl acetate | 6819-19-8 | DFHJK |
| 503 | Citrus Propanol | 15760-18-6 | CEFHIJK |
| 505 | Citronitrile | 93893-89-1 | CEFHJK |
| 519 | Citral propylene glycol acetal | 10444-50-5 | CEFHJK |
| 520 | Citral dimethyl acetal | 7549-37-3 | BCEFHJK |
| 521 | Citral diethyl acetal | 7492-66-2 | BDEFHJK |
| 524 | cis-Ocimene | 3338-55-4 | ADGIKL |
| 527 | cis-Limonene oxide | 13837-75-7 | ADEFGIJKL |
| 529 | Cis-iso-ambrettolide | 36508-31-3 | DGJ |
| 530 | cis-6-nonenol | 35854-86-5 | BCEFHIKL |
| 531 | cis-carveol | 1197-06-4 | BCHIJK |
| 532 | cis-4-Decen-1-al | 21662-09-9 | ADHKL |
| 534 | cis-3-hexenyl-cis-3-hexenoate | 61444-38-0 | BDEFHJK |
| 537 | cis-3-Hexenyl salicylate | 65405-77-8 | DEFGJ |
| 541 | Cis-3-hexenyl Benzoate | 25152-85-6 | DEFHJK |
| 544 | cis-3-Hexenyl 2-methylbutyrate | 53398-85-9 | ADEFHJKL |
| 546 | cis-3, cis-6-nonadienol | 53046-97-2 | ACEFHK |
| 548 | Cinnamyl propionate | 103-56-0 | DEFHJK |
| 550 | Cinnamyl isobutyrate | 103-59-3 | DEFHJK |
| 551 | Cinnamyl formate | 104-65-4 | BCEFHK |
| 552 | Cinnamyl cinnamate | 122-69-0 | DHJ |
| 553 | Cinnamyl acetate | 103-54-8 | BCEFHK |
| 555 | Cinnamic alcohol | 104-54-1 | BCEFHIK |
| 558 | Cetyl alcohol | 36653-82-4 | DEFHJ |
| 559 | (E)-1-(2,6,6-trimethylcyclohex-2-en-1-yl)hepta-1,6-dien-3-one | 79-78-7 | DHJK |

TABLE 1-continued

List of materials with at least one MORV from 1 to 5

| Number | Material Name | CAS Number | Comment Code |
|---|---|---|---|
| 560 | 2-methyl-4-(2,6,6-trimethylcyclohex-1-en-1-yl)butanal | 65405-84-7 | DFHJK |
| 561 | (3aR,5aR,9aR,9bR)-3a,6,6,9a-tetramethyldodecahydronaphtho[2,1-b]furan | 3738-00-9 | DEFHJK |
| 562 | 1,6-dioxacycloheptadecan-7-one | 6707-60-4 | DGJ |
| 563 | 1-(6-(tert-butyl)-1,1-dimethyl-2,3-dihydro-1H-inden-4-yl)ethan-1-one | 13171-00-1 | DEFHJK |
| 565 | Cedryl methyl ether | 19870-74-7 | ADEFHJK |
| 566 | Cedryl formate | 39900-38-4 | BDEFHJK |
| 567 | Cedryl acetate | 77-54-3 | DEFHJK |
| 568 | (4Z,8Z)-1,5,9-trimethyl-13-oxabicyclo[10.1.0]trideca-4,8-diene | 71735-79-0 | DFHJK |
| 569 | Cedrol | 77-53-2 | DEFHJK |
| 570 | 5-methyl-1-(2,2,3-trimethylcyclopent-3-en-1-yl)-6-oxabicyclo[3.2.1]octane | 139539-66-5 | DEFHJK |
| 571 | 5-methyl-1-(2,2,3-trimethylcyclopent-3-en-1-yl)-6-oxabicyclo[3.2.1]octane | 426218-78-2 | DFHJ |
| 572 | 1,1,2,3,3-pentamethyl-1,2,3,5,6,7-hexahydro-4H-inden-4-one | 33704-61-9 | BDEFHIJK |
| 573 | Caryophyllene alcohol acetate | 32214-91-8 | DEFHJK |
| 574 | Caryolan-1-ol | 472-97-9 | DEFHJK |
| 577 | Carvyl acetate | 97-42-7 | BDHIJK |
| 578 | Caprylnitrile | 124-12-9 | ACEFGIKL |
| 580 | Caprylic alcohol | 111-87-5 | ACEFGIKL |
| 581 | Caprylic acid | 124-07-2 | BCEFHIK |
| 582 | Capric acid | 334-48-5 | DEFHJK |
| 584 | Capraldehyde | 112-31-2 | ADHKL |
| 586 | 3-(4-methoxyphenyl)-2-methylpropanal | 5462-06-6 | BCHJK |
| 587 | Camphorquinone | 10373-78-1 | ACEFGIJK |
| 589 | Camphene | 79-92-5 | ADEFGIJKL |
| 591 | Ethyl 2-methyl-4-oxo-6-pentylcyclohex-2-ene-1-carboxylate | 59151-19-8 | DHJ |
| 592 | Butylated hydroxytoluene | 128-37-0 | DEFGIJK |
| 594 | Butyl stearate | 123-95-5 | DEFHJ |
| 595 | Butyl butyryl lactate | 7492-70-8 | CEFGJK |
| 599 | Butyl 10-undecenoate | 109-42-2 | DEFHJK |
| 600 | 2-methyl-4-(2,2,3-trimethylcyclopent-3-en-1-yl)butan-1-ol | 72089-08-8 | DEFHJK |
| 601 | 3-(4-(tert-butyl)phenyl)propanal | 18127-01-0 | BDHJK |
| 603 | Bornyl isobutyrate | 24717-86-0 | BDEFHIJK |
| 604 | Bornyl acetate | 76-49-3 | ADEFHIJKL |
| 606 | 2-ethoxy-2,6,6-trimethyl-9-methylenebicyclo[3.3.1]nonane | 68845-00-1 | BDEFHJK |
| 607 | (ethoxymethoxy)cyclododecane | 58567-11-6 | DEFHJK |
| 608 | Bisabolene | 495-62-5 | DEFHJK |
| 609 | Bigarade oxide | 72429-08-4 | ADEFHJKL |
| 610 | beta-Vetivone | 18444-79-6 | DHJK |
| 611 | beta-Terpinyl acetate | 10198-23-9 | BDHJK |
| 612 | beta-Terpineol | 138-87-4 | BCGIJK |
| 613 | beta-Sinensal | 60066-88-8 | DHJK |
| 614 | beta-Sesquiphellandrene | 20307-83-9 | DEFHJK |
| 615 | beta-Selinene | 17066-67-0 | BDEFGJK |
| 616 | beta-Santalol | 77-42-9 | DEFHJK |
| 618 | beta-Pinene | 127-91-3 | ADEFGIJKL |
| 620 | beta-Naphthyl ethyl ether | 93-18-5 | BDEFHJK |
| 621 | beta-Patchoulline | 514-51-2 | BDEFGJKL |
| 624 | beta-Himachalene Oxide | 57819-73-5 | BDFHJK |
| 625 | beta-Himachalene | 1461-03-6 | DEFHJKL |
| 626 | beta-Guaiene | 88-84-6 | DEFHJKL |
| 627 | (2,2-dimethoxyethyl)benzene | 101-48-4 | DHJK |
| 628 | beta-Farnesene | 18794-84-8 | DEFHJK |
| 631 | beta-Copaene | 18252-44-3 | BDEFHJKL |
| 632 | beta-Cedrene | 546-28-1 | BDEFGJKL |
| 633 | beta-Caryophyllene | 87-44-5 | DEFHJKL |
| 635 | beta-Bisabolol | 15352-77-9 | DFHJK |
| 636 | Beta ionone epoxide | 23267-57-4 | BDEFHIJK |
| 638 | Bergaptene | 484-20-8 | CGJ |
| 639 | Benzyl-tert-butanol | 103-05-9 | CEFGJK |
| 644 | Benzyl laurate | 140-25-0 | DEFHJ |
| 649 | Benzyl dimethyl carbinol | 100-86-7 | BCEFGIK |

TABLE 1-continued

List of materials with at least one MORV from 1 to 5

| Number | Material Name | CAS Number | Comment Code |
|---|---|---|---|
| 650 | Benzyl cinnamate | 103-41-3 | DHJ |
| 653 | Benzyl benzoate | 120-51-4 | DHJ |
| 655 | Benzophenone | 119-61-9 | DEFHK |
| 658 | 7-isopentyl-2H-benzo[b][1,4]dioxepin-3(4H)-one | 362467-67-2 | DHJ |
| 659 | 2'-isopropyl-1,7,7-trimethylspiro[bicyclo[2.2.1]heptane-2,4'-[1,3]dioxane] | 188199-50-0 | DEFHJK |
| 660 | 4-(4-methylpent-3-en-1-yl)cyclohex-3-ene-1-carbonitrile | 21690-43-7 | DEFHJK |
| 661 | Aurantiol | 89-43-0 | DEFHJ |
| 663 | Anisyl phenylacetate | 102-17-0 | DFHJ |
| 668 | Methyl (E)-octa-4,7-dienoate | 189440-77-5 | ACEFHKL |
| 671 | Amyl Cinnamate | 3487-99-8 | DEFHJK |
| 673 | (3aR,5aS,9aS,9bR)-3a,6,6,9a-tetramethyldodecahydronaphtho[2,1-b]furan | 6790-58-5 | DEFHJK |
| 674 | (4aR,5R,7aS,9R)-2,2,5,8,8,9a-hexamethyloctahydro-4H-4a,9-methanoazuleno[5,6-d][1,3]dioxole | 211299-54-6 | DEFHJK |
| 675 | 2,5,5-trimethyl-1,2,3,4,5,6,7,8-octahydronaphthalen-2-ol | 71832-76-3 | DEFHJK |
| 676 | 2,5,5-trimethyl-1,2,3,4,5,6,7,8-octahydronaphthalen-2-ol | 41199-19-3 | DEFHJK |
| 677 | 1-((2-(tert-butyl)cyclohexyl)oxy)butan-2-ol | 139504-68-0 | DEFHJK |
| 678 | (3S,5aR,7aS,11aS,11bR)-3,8,8,11a-tetramethyldodecahydro-5H-3,5a-epoxynaphtho[2,1-c]oxepine | 57345-19-4 | DEFHJ |
| 679 | 2,2,6,7,8,8-heptamethyldecahydro-2H-indeno[4,5-b]furan | 476332-65-7 | ADEFHJK |
| 680 | 2,2,6,6,7,8,8-heptamethyldecahydro-2H-indeno[4,5-b]furan | 647828-16-8 | ADEFHJK |
| 681 | Amber acetate | 37172-02-4 | BDEFHJK |
| 682 | Alpinofix ® | 811436-82-5 | DEFHJ |
| 683 | alpha-Thujone | 546-80-5 | ADEFGIJKL |
| 684 | alpha-Vetivone | 15764-04-2 | DHJK |
| 686 | alpha-Terpinyl propionate | 80-27-3 | BDEFHJK |
| 691 | alpha-Sinensal | 17909-77-2 | DHJK |
| 692 | alpha-Selinene | 473-13-2 | BDEFHJK |
| 693 | alpha-Santalene | 512-61-8 | ADEFHJKL |
| 694 | alpha-Santalol | 115-71-9 | DEFHJK |
| 696 | alpha-Patchoulene | 560-32-7 | ADEFHJKL |
| 697 | alpha-neobutenone | 56973-85-4 | BDHJK |
| 698 | alpha-Muurolene | 10208-80-7 | DEFHJKL |
| 700 | alpha-methyl ionone | 127-42-4 | BDHJK |
| 702 | alpha-Limonene | 138-86-3 | ADEFGIJKL |
| 704 | alpha-Irone | 79-69-6 | BDHJK |
| 706 | alpha-Humulene | 6753-98-6 | DEFHJK |
| 707 | alpha-Himachalene | 186538-22-7 | BDEFHJK |
| 708 | alpha-Gurjunene | 489-40-7 | BDEFHJKL |
| 709 | alpha-Guaiene | 3691-12-1 | DEFHJKL |
| 710 | alpha-Farnesene | 502-61-4 | DEFHJK |
| 711 | alpha-Fenchene | 471-84-1 | ADEFGIJKL |
| 712 | alpha-Eudesmol | 473-16-5 | DEFHJK |
| 713 | alpha-Curcumene | 4176-17-4 | DEFHJK |
| 714 | alpha-Cubebene | 17699-14-8 | ADEFHJKL |
| 715 | alpha-Cedrene epoxide | 13567-39-0 | ADEFHJK |
| 716 | alpha-Cadinol | 481-34-5 | DEFHJK |
| 717 | alpha-Cadinene | 24406-05-1 | DEFHJKL |
| 718 | alpha-Bisabolol | 515-69-5 | DFHJK |
| 719 | alpha-bisabolene | 17627-44-0 | DEFHJK |
| 720 | alpha-Bergamotene | 17699-05-7 | BDEFHJKL |
| 721 | alpha-Amylcinnamyl alcohol | 101-85-9 | DEFHJ |
| 722 | alpha-Amylcinnamyl acetate | 7493-78-9 | DEFHJ |
| 723 | alpha-Amylcinnamaldehyde diethyl acetal | 60763-41-9 | DEFHJ |
| 724 | alpha-Amylcinnamaldehyde | 122-40-7 | DHJK |
| 725 | alpha-Amorphene | 23515-88-0 | DEFHJKL |
| 726 | alpha-Agarofuran | 5956-12-7 | BDEFHJK |
| 727 | 1-methyl-4-(4-methyl-3-penten-1-yl)-3-Cyclohexene-1-carboxaldehyde | 52475-86-2 | DFHJK |
| 730 | 1-Phenyl-2-pentanol | 705-73-7 | CEFHK |
| 731 | 1-Phenyl-3-methyl-3-pentanol | 10415-87-9 | CEFHJK |
| 733 | 2,3,4-trimethoxy-benzaldehyde | 2103-57-3 | BCGI |

TABLE 1-continued

List of materials with at least one MORV from 1 to 5

| Number | Material Name | CAS Number | Comment Code |
|---|---|---|---|
| 735 | 2,4,5-trimethoxy-benzaldehyde | 4460-86-0 | BCG |
| 736 | 2,4,6-trimethoxybenzaldehyde | 830-79-5 | BCGI |
| 738 | 2,4-Nonadienal | 6750-03-4 | ACHKL |
| 741 | 2,6,10-Trimethylundecanal | 105-88-4 | BDFGJK |
| 742 | alpha,4-Dimethyl benzenepropanal | 41496-43-9 | ACHJK |
| 746 | Allyl cyclohexyl propionate | 2705-87-5 | BDEFHJK |
| 748 | Allyl amyl glycolate | 67634-00-8 | BCEFGJK |
| 750 | Allo-aromadendrene | 25246-27-9 | BDEFHJKL |
| 752 | Aldehyde C-11 | 143-14-6 | ADHJK |
| 754 | Methyl (E)-2-(((3,5-dimethylcyclohex-3-en-1-yl)methylene)amino)benzoate | 94022-83-0 | DEFHJ |
| 757 | 2,6,10-trimethylundec-9-enal | 141-13-9 | BDFHJK |
| 758 | Acetoxymethyl-isolongifolene (isomers) | 59056-62-1 | BDEFHJK |
| 763 | Acetate C9 | 143-13-5 | BDEFHJKL |
| 764 | Acetarolle ® | 744266-61-3 | DFHJK |
| 766 | Acetaldehyde phenylethyl propyl acetal | 7493-57-4 | CEFHJK |
| 767 | Acetaldehyde dipropyl acetal | 105-82-8 | ACEFGIKL |
| 768 | Acetaldehyde benzyl 2-methoxyethyl acetal | 7492-39-9 | BCEFHJK |
| 769 | (Z)-2-(4-methylbenzylidene)heptanal | 84697-09-6 | DHJ |
| 770 | 9-decenal | 39770-05-3 | ADHKL |
| 771 | 8-Hexadecenolide | 123-69-3 | DGJ |
| 772 | 7-Methoxycoumarin | 531-59-9 | CHK |
| 774 | 7-epi-alpha-Selinene | 123123-37-5 | BDEFHJK |
| 775 | 7-eip-alpha-Eudesmol | 123123-38-6 | DEFHJK |
| 776 | 7-Acetyl-1,1,3,4,4,6-hexamethyltetralin | 1506-02-1 | DEFHJ |
| 778 | 6-Isopropylquinoline | 135-79-5 | CEFHJK |
| 781 | 6,6-dimethyl-2-norpinene-2-propionaldehyde | 33885-51-7 | BCFHJK |
| 782 | 6,10,14-trimethyl-2-Pentadecanone | 502-69-2 | DEFHJK |
| 786 | 5-Isopropenyl-2-methyl-2-vinyltetrahydrofuran | 13679-86-2 | ACGIJKL |
| 788 | 5-Cyclohexadecenone | 37609-25-9 | DEFGJK |
| 791 | 4-Terpinenol | 562-74-3 | BCHIJK |
| 792 | 4-Pentenophenone | 3240-29-7 | BCEFHIK |
| 800 | 4-Carvomenthenol | 28219-82-1 | BCHIJK |
| 802 | 4,5,6,7-Tetrahydro-3,6-dimethylbenzofuran | 494-90-6 | BCEFHIJKL |
| 803 | 4-(p-Methoxyphenyl)-2-butanone | 104-20-1 | BCEFHJK |
| 804 | 3-Thujopsanone | 25966-79-4 | BDEFHJK |
| 805 | 3-Propylidenephthalide | 17369-59-4 | CEFHK |
| 806 | 3-Nonylacrolein | 20407-84-5 | BDFHJK |
| 807 | 3-Methyl-5-phenyl-1-pentanal | 55066-49-4 | BDFHJK |
| 814 | 3-Hexenyl isovalerate | 10032-11-8 | ADEFHJKL |
| 821 | 3,6-Dimethyl-3-octanyl acetate | 60763-42-0 | ADEFHIJKL |
| 824 | 3,4,5-trimethoxybenzaldehyde | 86-81-7 | BCGIK |
| 826 | 3-(p-Isopropylphenyl)propionaldehyde | 7775-00-0 | BDFHJK |
| 827 | 2-Undecenenitrile | 22629-48-7 | BDEFHJK |
| 828 | 2-Undecenal | 2463-77-6 | ADHJK |
| 829 | 2-trans-6-trans-Nonadienal | 17587-33-6 | ACHKL |
| 831 | 2-Phenylethyl butyrate | 103-52-6 | DEFHJK |
| 833 | 2-Phenyl-3-(2-furyl)prop-2-enal | 57568-60-2 | CHJ |
| 834 | 2-Phenoxyethanol | 122-99-6 | BCEFGIK |
| 837 | 2-Nonen-1-al | 2463-53-8 | ADHKL |
| 839 | 2-Nonanol | 628-99-9 | BDEFGIKL |
| 840 | 2-Nonanone | 821-55-6 | ADFHIKL |
| 849 | 2-Isobutyl quinoline | 93-19-6 | CEFHJK |
| 850 | 2-Hexylidene cyclopentanone | 17373-89-6 | DFHJKL |
| 852 | 2-Heptyl tetrahydrofuran | 2435-16-7 | BDEFHJKL |
| 856 | 2-Decenal | 3913-71-1 | ADHKL |
| 864 | 2,6-Nonadienal | 26370-28-5 | ACHKL |
| 865 | 2,6-Nonadien-1-ol | 7786-44-9 | ACEFHK |
| 866 | 2,6-dimethyl-octanal | 7779-07-9 | ADFGIJKL |
| 868 | 1-Decanol | 112-30-1 | BDEFGJK |
| 869 | 1-Hepten-1-ol, 1-acetate | 35468-97-4 | ACEFHKL |
| 870 | 10-Undecen-1-ol | 112-43-6 | DEFHJK |
| 871 | 10-Undecenal | 112-45-8 | ADHJK |
| 872 | 10-epi-gamma-Eudesmol | 15051-81-7 | DFHJK |
| 873 | 1,8-Thiocineol | 68391-28-6 | ADEFHIJKL |
| 876 | 1,3,5-undecatriene | 16356-11-9 | ADEFHJKL |

TABLE 1-continued

List of materials with at least one MORV from 1 to 5

| Number | Material Name | CAS Number | Comment Code |
|---|---|---|---|
| 877 | 1,2-Dihydrolinalool | 2270-57-7 | BCEFGIJKL |
| 878 | 1,3,3-trimethyl-2-norbornanyl acetate | 13851-11-1 | ADEFHIJKL |
| 879 | 1,1,2,3,3-Pentamethylindan | 1203-17-4 | ADHIJKL |
| 881 | (Z)-6,10-dimethylundeca-5,9-dien-2-yl acetate | 3239-37-0 | DEFHJK |
| 884 | (Z)-3-Dodecenal | 68141-15-1 | BCFHJK |
| 885 | (S)-gamma-Undecalactone | 74568-05-1 | DEFHJKL |
| 886 | (R)-gamma-Undecalactone | 74568-06-2 | DEFHJKL |
| 890 | (E)-6,10-dimethylundeca-5,9-dien-2-yl acetat | 3239-35-8 | DEFHJK |
| 892 | (2Z)-3-methyl-5-phenyl-2-Pentenenitrile | 53243-59-7 | DEFHJK |
| 893 | (2S,5S,6S)-2,6,10,10-tetramethyl-1-oxaspiro[4_5]decan-6-ol | 65620-50-0 | DFHIJK |
| 894 | (2E)-3-methyl-5-phenyl-2-pentenenitrile | 53243-60-0 | CEFHJK |
| 897 | (+)-Dihydrocarveol | 22567-21-1 | BCEFHIJKL |
| 905 | Menthone | 89-80-5 | ADEFGIJKL |
| 908 | (R,E)-2-methyl-4-(2,2,3-trimethylcyclopent-3-en-1-yl)but-2-en-1-ol | 185068-69-3 | CHJK |
| 912 | 2-(8-isopropyl-6-methylbicyclo[2.2.2]oct-5-en-2-yl)-1,3-dioxolane | 68901-32-6 | DEFHJK |
| 913 | gamma-methyl ionone | 7388-22-9 | BDHIJK |
| 914 | 3-(3-isopropylphenyl)butanal | 125109-85-5 | BDHJK |
| 916 | 3-(1-ethoxyethoxy)-3,7-dimethylocta-1,6-diene | 40910-49-4 | BDEFHJK |
| 919 | 3a,4,5,6,7,7a-hexahydro-1H-4,7-methanoinden-6-yl propionate | 17511-60-3 | CEFHJK |
| 920 | Bulnesol | 22451-73-6 | DEFHJK |
| 922 | Benzyl phenylacetate | 102-16-9 | DHJ |
| 923 | Benzoin | 119-53-9 | CEFHJ |
| 924 | (E)-1,2,4-trimethoxy-5-(prop-1-en-1-yl)benzene | 2883-98-9 | BCFGJK |
| 925 | alpha,alpha,6,6-tetramethyl bicyclo[3.1.1]hept-2-ene-propanal | 33885-52-8 | BDFHJK |
| 926 | 7-epi-sesquithujene | 159407-35-9 | DEFHJKL |
| 927 | 5-Acetyl-1,1,2,3,3,6-hexamethylindan | 15323-35-0 | DEFHJK |
| 928 | 3-Methylphenethyl alcohol | 1875-89-4 | BCEFHIK |
| 929 | 3,6-Nonadien-1-ol | 76649-25-7 | ACEFHK |
| 930 | 2-Tridecenal | 7774-82-5 | BDFHJK |
| 933 | Patchouli alcohol | 5986-55-0 | DEFHIJK |
| 937 | p-Cresyl isobutyrate | 103-93-5 | BDHJK |
| 939 | p-Cresyl n-hexanoate | 68141-11-7 | DEFHJK |
| 941 | 5-hexyl-4-methyldihydrofuran-2(3H)-one | 67663-01-8 | BDEFHIJKL |
| 942 | Ethyl (2Z,4E)-deca-2,4-dienoate | 3025-30-7 | BDEFHJK |
| 943 | Pelargene | 68039-40-7 | DEFHJK |
| 945 | 2-cyclohexylidene-2-phenylacetonitrile | 10461-98-0 | DFHJK |
| 946 | Perillaldehyde | 2111-75-3 | ACHIJK |
| 947 | Perillyl acetate | 15111-96-3 | DFHJK |
| 948 | Perillyl alcohol | 536-59-4 | CHIJK |
| 950 | (2-isopropoxyethyl)benzene | 68039-47-4 | ACEFHJKL |
| 951 | Ethyl (2Z,4E)-deca-2,4-dienoate | 313973-37-4 | BDEFHJK |
| 953 | (2-(cyclohexyloxy)ethyl)benzene | 80858-47-5 | DEFHJK |
| 954 | Phenethyl 2-methylbutyrate | 24817-51-4 | DEFHJK |
| 955 | Phenethyl alcohol | 60-12-8 | BCEFGIK |
| 959 | Phenethyl phenylacetate | 102-20-5 | DHJ |
| 962 | Phenoxanol | 55066-48-3 | DEFHJK |
| 965 | Phenyl benzoate | 93-99-2 | DFHJK |
| 967 | Phenyl ethyl benzoate | 94-47-3 | DHJ |
| 969 | Phenylacetaldehyde ethyleneglycol acetal | 101-49-5 | BCEFGIK |
| 973 | 2-(6,6-dimethylbicyclo[3.1.1]hept-2-en-2-yl)acetaldehyde | 30897-75-7 | ACFHIJKL |
| 974 | Pinocarveol | 5947-36-4 | BCEFGIJKL |
| 976 | Piperonyl acetone | 55418-52-5 | CEFGJ |
| 978 | 3a,4,5,6,7,7a-hexahydro-1H-4,7-methanoinden-6-yl pivalate | 68039-44-1 | DEFHJK |
| 980 | (4aR,8aS)-7-methyloctahydro-1,4-methanonaphthalen-6(2H)-one | 41724-19-0 | CEFGJKL |

TABLE 1-continued

| List of materials with at least one MORV from 1 to 5 | | | |
|---|---|---|---|
| Number | Material Name | CAS Number | Comment Code |
| 982 | p-Menth-3-en-1-ol | 586-82-3 | BCGIJK |
| 985 | (E)-3,3-dimethyl-5-(2,2,3-trimethylcyclopent-3-en-1-yl)pent-4-en-2-ol | 107898-54-4 | DHJK |
| 988 | 1-methyl-4-(4-methylpent-3-en-1-yl)cyclohex-3-ene-1-carbaldehyde | 52474-60-9 | DFHJK |
| 993 | Propylene glycol | 57-55-6 | ACEFGIKL |
| 998 | p-Tolyl phenylacetate | 101-94-0 | DFHJ |
| 1000 | Ethyl 2,4,7-decatrienoate | 78417-28-4 | BDEFHJK |
| 1003 | 2-benzyl-4,4,6-trimethyl-1,3-dioxane | 67633-94-7 | DEFHJK |
| 1006 | 2,4-dimethyl-4-phenyltetrahydrofuran | 82461-14-1 | BDEFHJK |
| 1007 | (2R,4a'R,8a'R)-3,7'-dimethyl-3',4',4a',5',8',8a'-hexahydro-1'H-spiro[oxirane-2,2'-[1,4]methanonaphthalene] | 41816-03-9 | DEFHJK |
| 1008 | (Z)-6-ethylideneoctahydro-2H-5,8-methanochromene | 93939-86-7 | BCEFHJKL |
| 1009 | 2-((S)-1-((S)-3,3-dimethylcyclohexyl)ethoxy)-2-oxoethyl propionate | 236391-76-7 | DFHJ |
| 1010 | Methyl 2,2-dimethyl-6-methylenecyclohexane-1-carboxylate | 81752-87-6 | ADHIJKL |
| 1012 | 2-methyl-5-phenylpentan-1-ol | 25634-93-9 | DEFHJK |
| 1016 | 4-methyl-2-phenyl-3,6-dihydro-2H-pyran | 60335-71-9 | BCEFGJK |
| 1020 | Sabinol | 471-16-9 | BCEFHIJKL |
| 1021 | Safrole | 94-59-7 | BCEFHK |
| 1022 | 2,2,7,9-tetramethylspiro(5.5)undec-8-en-1-one | 502847-01-0 | DHIJK |
| 1023 | 3-methyl-5-(2,2,3-trimethylcyclopent-3-en-1-yl)pentan-2-ol | 65113-99-7 | DEFHJK |
| 1024 | (Z)-2-ethyl-4-(2,2,3-trimethylcyclopent-3-en-1-yl)but-2-en-1-ol | 28219-61-6 | DEFHJK |
| 1025 | (E)-2-methyl-4-(2,2,3-trimethylcyclopent-3-en-1-yl)but-2-en-1-ol | 28219-60-5 | CHJK |
| 1026 | 5-methoxyoctahydro-1H-4,7-methanoindene-2-carbaldehyde | 86803-90-9 | CHJK |
| 1027 | 5-methoxyoctahydro-1H-4,7-methanoindene-2-carbaldehyde | 193425-86-4 | CHJK |
| 1028 | Sclareol | 515-03-7 | DEFHJ |
| 1029 | Sclareol oxide | 5153-92-4 | DEFHJK |
| 1031 | Selina-3,7(11)-diene | 6813-21-4 | DEFHJKL |
| 1032 | 2-(1-(3,3-dimethylcyclohexyl)ethoxy)-2-methylpropyl cyclopropanecarboxylate | 477218-42-1 | DEFHJ |
| 1033 | 3-(4-isobutylphenyl)-2-methylpropanal | 6658-48-6 | DHJK |
| 1035 | Spathulenol | 6750-60-3 | DEFHJK |
| 1036 | Spirambrene | 533925-08-5 | BCEFHJK |
| 1037 | Spirodecane | 6413-26-9 | BCEFGIJKL |
| 1038 | 1-(spiro[4.5]dec-7-en-7-yl)pent-4-en-1-one | 224031-70-3 | DGJK |
| 1042 | 2-(4-methylthiazol-5-yl)ethan-1-ol | 137-00-8 | CGIKL |
| 1043 | 2-(heptan-3-yl)-1,3-dioxolane | 4359-47-1 | ACEFHIJKL |
| 1045 | (Z)-dodec-4-enal | 21944-98-9 | BDFHJK |
| 1046 | tau-Cadinol | 5937-11-1 | DEFHJK |
| 1047 | tau-Muurolol | 19912-62-0 | DEFHJK |
| 1053 | Tetrahydrojasmone | 13074-63-0 | BDFHIJKL |
| 1057 | 2,6,10,10-tetramethyl-1-oxaspiro[4.5]dec-6-ene | 36431-72-8 | BDFHIJKL |
| 1059 | Thiomenthone | 38462-22-5 | BDEFHIJKL |
| 1060 | Thujopsene | 470-40-6 | BDEFGJKL |
| 1062 | Thymol methyl ether | 1076-56-8 | ADHIJKL |
| 1063 | 1-(2,2,6-trimethylcyclohexyl)hexan-3-ol | 70788-30-6 | DEFHJK |
| 1064 | trans,trans-2,4-Nonadienal | 5910-87-2 | ACHKL |
| 1065 | trans,trans-Farnesol | 106-28-5 | DEFHJK |
| 1066 | trans-2,cis-6-Nonadienal | 557-48-2 | ACHKL |
| 1067 | trans-2-Decenal | 3913-81-3 | ADHKL |
| 1070 | trans-2-Nonen-1-al | 18829-56-6 | ADHKL |

TABLE 1-continued

| List of materials with at least one MORV from 1 to 5 | | | |
|---|---|---|---|
| Number | Material Name | CAS Number | Comment Code |
| 1072 | trans-3,cis-6-nonadienol | 56805-23-3 | ACEFHK |
| 1073 | trans-4-Decen-1-al | 65405-70-1 | ADHKL |
| 1075 | trans-ambrettolide | 51155-12-5 | DGJ |
| 1077 | trans-beta-ocimene | 13877-91-3 | ADGIKL |
| 1078 | trans-beta-Ocimene | 3779-61-1 | ADGIKL |
| 1082 | trans-Geraniol | 106-24-1 | BCHIK |
| 1083 | trans-Hedione | 2570-03-8 | DFHJK |
| 1085 | 7-(1,1-Dimethylethyl)-2H-1,5-benzodioxepin-3(4H)-one | 195251-91-3 | CEFHJ |
| 1089 | Tricyclone | 68433-81-8 | DEFHJK |
| 1090 | Tridecyl alcohol | 112-70-9 | DEFGJK |
| 1091 | Triethyl citrate | 77-93-0 | CEFGJ |
| 1093 | Methyl 2-((1-hydroxy-3-phenylbutyl)amino)benzoate | 144761-91-1 | DFHJ |
| 1095 | 1-((2E,5Z,9Z)-2,6,10-trimethylcyclododeca-2,5,9-trien-1-yl)ethan-1-one | 28371-99-5 | DHJK |
| 1097 | Decahydro-2,6,6,7,8,8-hexamethyl-2h-indeno(4,5-b)furan | 338735-71-0 | BDEFHJK |
| 1099 | 13-methyl oxacyclopentadec-10-en-2-one | 365411-50-3 | DEFHJK |
| 1102 | Undecanal | 112-44-7 | BDHJK |
| 1104 | (E)-4-methyldec-3-en-5-ol | 81782-77-6 | BDEFHIJK |
| 1105 | Valencene | 4630-07-3 | BDEFHJK |
| 1107 | Valerianol | 20489-45-6 | DEFHJK |
| 1111 | Vanillin isobutyrate | 20665-85-4 | CHJ |
| 1113 | Vaniwhite ® | 5533-03-9 | CGIK |
| 1116 | (Z)-2-methyl-4-(2,6,6-trimethylcyclohex-2-en-1-yl)but-2-enal | 68555-62-4 | BDFHJK |
| 1117 | Methyl 2,4-dihydroxy-3,6-dimethylbenzoate | 4707-47-5 | CGIJ |
| 1120 | 1-methoxy-3a,4,5,6,7,7a-hexahydro-1H-4,7-methanoindene | 27135-90-6 | ACEFHJKL |
| 1121 | Methyl (Z)-2-((3-(4-(tert-butyl)phenyl)-2-methylpropylidene)amino)benzoate | 91-51-0 | DFHJ |
| 1125 | (Z)-hex-3-en-1-yl isobutyrate | 41519-23-7 | ADEFHJKL |
| 1126 | Vertacetal | 5182-36-5 | BCFHJK |
| 1129 | 1-((3R,3aR,7R,8aS)-3,6,8,8-tetramethyl-2,3,4,7,8,8a-hexahydro-1H-3a,7-methanoazulen-5-yl)ethan-1-one | 32388-55-9 | DHJK |
| 1131 | Methyl (Z)-2-(((2,4-dimethylcyclohex-3-en-1-yl)methylene)amino)benzoate | 68738-99-8 | DEFHJ |
| 1135 | Vetiverol | 89-88-3 | CEFHIJK |
| 1136 | Vetivert Acetate | 117-98-6 | DEFHJK |
| 1137 | Decahydro-3H-spiro[furan-2,5'-[4,7]methanoindene] | 68480-11-5 | DEFGJKL |
| 1138 | (2Z,6E)-nona-2,6-dienenitrile | 67019-89-0 | ACEFHKL |
| 1139 | (Z)-cyclooct-4-en-1-yl methyl carbonate | 87731-18-8 | BCHJKL |
| 1140 | (1aR,4S,4aS,7R,7aS,7bS)-1,1,4,7-tetramethyldecahydro-1H-cyclopropa[e]azulen-4-ol | 552-02-3 | DEFHJK |
| 1142 | 3,5,5,6,7,8,8-heptamethyl-5,6,7,8-tetrahydronaphthalene-2-carbonitrile | 127459-79-4 | DHJ |
| 1143 | (1S,2S,3S,5R)-2,6,6-trimethylspiro[bicyclo[3.1.1]heptane-3,1'-cyclohexan]-2'-en-4'-one | 133636-82-5 | DEFHJK |
| 1144 | 1',1',5',5'-tetramethylhexahydro-2'H,5'H-spiro[[1,3]dioxolane-2,8'-[2,4a]methanonaphthalene] | 154171-76-3 | DEFHJK |
| 1145 | 1',1',5',5'-tetramethylhexahydro-2'H,5'H-spiro[[1,3]dioxolane-2,8'-[2,4a]methanonaphthalene] K | 154171-77-4 | DEFHJK |
| 1146 | 4-(4-hydroxy-3-methoxyphenyl)butan-2-one | 122-48-5 | CEFGJ |
| 1147 | (1R,8aR)-4-isopropyl-1,6-dimethyl-1,2,3,7,8,8a-hexahydronaphthalene | 41929-05-9 | DEFHJKL |
| 1148 | 4,5-epoxy-4,11,11-trimethyl-8-methylenebicyclo(7.2.0)undecane | 1139-30-6 | DEFHJK |

TABLE 1-continued

List of materials with at least one MORV from 1 to 5

| Number | Material Name | CAS Number | Comment Code |
|---|---|---|---|
| 1149 | 1,3,4,6,7,8alpha-hexahydro-1,1,5,5-tetramethyl-2H-2,4alpha-methanophtalen-8(5H)-one | 23787-90-8 | DEFHIJK |

TABLE 2

List of materials with at least one MORV greater than 5 to 10

| Number | Material Name | CAS Number | Comment Code |
|---|---|---|---|
| 2 | 2,4-dimethyl-2-(5,5,8,8-tetramethyl-5,6,7,8-tetrahydronaphthalen-2-yl)-1,3-dioxolane | 131812-67-4 | DFHJ |
| 23 | 3a,5,6,7,8,8b-hexahydro-2,2,6,6,7,8,8-heptamethyl-4H-indeno(4,5-d)-1,3-dioxole | 823178-41-2 | DEFHJK |
| 141 | 2,4-dimethyl-4,4a,5,9b-tetrahydroindeno[1,2-d][1,3]dioxine | 27606-09-3 | CEFHJK |
| 185 | (1-methyl-2-((1,2,2-trimethylbicyclo[3.1.0]hexan-3-yl)methyl)cyclopropyl)methanol | 198404-98-7 | DEFHJK |
| 227 | Isobornylcyclohexanol | 68877-29-2 | DEFHJK |
| 230 | Isobornyl cyclohexanol | 66072-32-0 | DEFHJK |
| 246 | Indol/Hydroxycitronellal Schiff base | 67801-36-9 | DEFHJ |
| 248 | Hydroxymethyl isolongifolene | 59056-64-3 | DEFHJK |
| 343 | 8,8-dimethyl-3a,4,5,6,7,7a-hexahydro-1H-4,7-methanoinden-6-yl propionate | 76842-49-4 | DEFHJK |
| 359 | (E)-4-((3aR,4R,7R,7aR)-1,3a,4,6,7,7a-hexahydro-5H-4,7-methanoinden-5-ylidene)-3-methylbutan-2-ol | 501929-47-1 | DEFHJK |
| 565 | Cedryl methyl ether | 19870-74-7 | BDEFHJK |
| 631 | beta-Copaene | 18252-44-3 | BDEFHJKL |
| 659 | 2'-isopropyl-1,7,7-trimethylspiro[bicyclo[2.2.1]heptane-2,4'-[1,3]dioxane] | 869292-93-3 | BDEFHJK |
| 674 | (4aR,5R,7aS,9R)-2,2,5,8,8,9a-hexamethyloctahydro-4H-4a,9-methanoazuleno[5,6-d][1,3]dioxole | 211299-54-6 | DEFHJK |
| 678 | (3S,5aR,7aS,11aS,11bR)-3,8,8,11a-tetramethyldodecahydro-5H-3,5a-epoxynaphtho[2,1-c]oxepine | 57345-19-4 | DEFHJ |
| 679 | 2,2,6,6,7,8,8-heptamethyldecahydro-2H-indeno[4,5-b]furan | 476332-65-7 | DEFHJK |
| 715 | alpha-Cedrene epoxide | 13567-39-0 | BDEFHJK |
| 758 | Acetoxymethyl-isolongifolene (isomers) | 59056-62-1 | DEFHJK |
| 1028 | Sclareol | 515-03-7 | DEFHJ |
| 1097 | Decahydro-2,6,6,7,8,8-hexamethyl-2h-indeno(4,5-b)furan | 338735-71-0 | DEFHJK |

TABLE 3

List of materials with at least one MORV from 0.5 to less than 1

| Number | Material Name | CAS Number | Comment Code |
|---|---|---|---|
| 12 | 1-ethoxy-4-(tert-pentyl)cyclohexane | 181258-89-9 | ADEFHJK |
| 19 | (3Z)-1-(2-buten-1-yloxy)-3-hexene | 888744-18-1 | ADEFHJKL |
| 20 | 4-(2-methoxypropan-2-yl)-1-methylcyclohex-1-ene | 14576-08-0 | ADHIJKL |
| 24 | O-Methyl linalool | 60763-44-2 | ADHIJKL |
| 26 | o-Methoxycinnamaldehyde | 1504-74-1 | ACHK |
| 27 | Octanal, 3,7-dimethyl- | 25795-46-4 | ADGIJKL |

TABLE 3-continued

List of materials with at least one MORV from 0.5 to less than 1

| Number | Material Name | CAS Number | Comment Code |
|---|---|---|---|
| 53 | 3,3-Dimethyl-5(2,2,3-Trimethyl-3-Cyclopenten-1yl)-4-Penten-2-ol | 329925-33-9 | CEFHJ |
| 54 | n-Hexyl salicylate | 6259-76-3 | DEFHJ |
| 55 | n-Hexyl 2-butenoate | 19089-92-0 | ADEFHJKL |
| 59 | Neryl Formate | 2142-94-1 | BCEFHJK |
| 72 | Methyl-beta-ionone | 127-43-5 | DHJK |
| 73 | Myroxide | 28977-57-3 | ADGIJKL |
| 81 | (E)-3,7-dimethylocta-4,6-dien-3-ol | 18479-54-4 | BCEFGIJK |
| 84 | (Z)-hex-3-en-1-yl cyclopropanecarboxylate | 188570-78-7 | BCEFHIKL |
| 96 | Methyl phenyl carbinyl propionate | 120-45-6 | BCHJK |
| 97 | Methyl phenylacetate | 101-41-7 | ACEFHIKL |
| 107 | 2-methyl-6-oxaspiro[4.5]decan-7-one | 91069-37-3 | BCEFGIKL |
| 111 | Methyl geraniate | 2349-14-6 | BCHJKL |
| 115 | 2-ethoxy-4-(methoxymethyl)phenol | 5595-79-9 | CFGK |
| 116 | Methyl cyclopentylideneacetate | 40203-73-4 | ACEFHIKL |
| 125 | Methoxymelonal | 62439-41-2 | ACGIJK |
| 133 | ((1s,4s)-4-isopropylcyclohexyl)methanol | 13828-37-0 | BDEFHIJK |
| 147 | Linalyl propionate | 144-39-8 | BDFHJK |
| 150 | Linalyl formate | 115-99-1 | ACFHJK |
| 151 | Linalyl butyrate | 78-36-4 | BDEFHJK |
| 154 | Linalyl acetate | 115-95-7 | BDHJK |
| 157 | Linalool | 78-70-6 | BCEFGIJK |
| 163 | (Z)-hex-3-en-1-yl methyl carbonate | 67633-96-9 | ACEFGKL |
| 166 | Lepidine | 491-35-0 | BCEFHIKL |
| 169 | L-Carvone | 6485-40-1 | ACGIJKL |
| 181 | Khusinil | 75490-39-0 | DHJK |
| 191 | Isoraldeine | 1335-46-2 | BDHIJK |
| 194 | Isopropylvinylcarbinol | 4798-45-2 | ACGIKL |
| 198 | Isopropyl 2-methylbutyrate | 66576-71-4 | ACEFGIJKL |
| 201 | Isopentyrate | 80118-06-5 | ADEFGIJKL |
| 204 | Isononyl acetate | 40379-24-6 | BDEFHJKL |
| 205 | Isononanol | 27458-94-2 | BDEFGIKL |
| 213 | Isoeugenyl acetate | 93-29-8 | CFHJK |
| 214 | Isoeugenol | 97-54-1 | CEFHIK |
| 232 | Isoborneol | 124-76-5 | ACEFHIJKL |
| 237 | Isoamyl octanoate | 2035-99-6 | DEFHJK |
| 239 | Isoamyl isobutyrate | 2050-01-3 | ACEFGIJKL |
| 255 | Hydrocinnamic acid | 501-52-0 | CEFHIK |
| 258 | Hydratopic alcohol | 1123-85-9 | BCEFHIK |
| 264 | Hexyl propanoate | 2445-76-3 | ADEFHIKL |
| 270 | Hexyl butyrate | 2639-63-6 | BDEFHJKL |
| 273 | Hexyl 2-methylbutanoate | 10032-15-2 | BDEFHJKL |
| 275 | Hexyl 2-furoate | 39251-86-0 | DEFHJK |
| 282 | Heptyl alcohol | 111-70-6 | ACEFGIKL |
| 283 | Heptyl acetate | 112-06-1 | ADEFHKL |
| 284 | Heptaldehyde | 111-71-7 | ACHIKL |
| 287 | Heliotropin | 120-57-0 | BCGIK |
| 302 | Geranyl nitrile | 5146-66-7 | BCEFHKL |
| 306 | Geranyl formate | 105-86-2 | BCEFHJK |
| 308 | Geranyl caprylate | 51532-26-4 | DEFHJ |
| 310 | Geranyl benzoate | 94-48-4 | DFHJ |
| 312 | Geranial | 141-27-5 | ACHIKL |
| 314 | N,2-dimethyl-N-phenylbutanamide | 84434-18-4 | BCEFHJK |
| 319 | gamma-Terpinene | 99-85-4 | ADEFGIJKL |
| 346 | 2-(sec-butyl)cyclohexan-1-one | 14765-30-1 | ADFHIKL |
| 354 | 3-(2-ethylphenyl)-2,2-dimethylpropanal | 67634-14-4 | BDHJK |
| 355 | 2-(tert-butyl)cyclohexyl ethyl carbonate | 67801-64-3 | BDFHJK |
| 365 | 2-(tert-butyl)cyclohexyl ethyl carbonate | 81925-81-7 | ACFHIKL |
| 366 | Fenchyl alcohol | 1632-73-1 | ACGIJKL |
| 376 | Eucalyptol | 470-82-6 | ADEFGIJKL |
| 379 | Ethyl vanillin acetate | 72207-94-4 | CHJ |
| 387 | Ethyl octanoate | 106-32-1 | BDEFHJKL |

TABLE 3-continued

| List of materials with at least one MORV from 0.5 to less than 1 | | | |
|---|---|---|---|
| Number | Material Name | CAS Number | Comment Code |
| 400 | Ethyl cinnamate | 103-36-6 | BCEFHK |
| 412 | Ethyl 2-(cyclohexyl)propionate | 2511-00-4 | BDFHIJKL |
| 419 | d-p-8(9)-Menthen-2-one | 5524-05-0 | ACGIJKL |
| 420 | 4-methyl-2-phenyltetrahydro-2H-pyran | 94201-73-7 | BDEFHJK |
| 437 | Dihydromyrcenol | 18479-58-8 | ADEFGIJK |
| 438 | Dihydrojasmone | 1128-08-1 | BCFHIJKL |
| 439 | Dihydroisophorone | 873-94-9 | ACEFGIJKL |
| 440 | Dihydroeugenol | 2785-87-7 | CEFHIJK |
| 442 | Dihydrocoumarin | 119-84-6 | BCGIKL |
| 443 | Dihydrocarvone | 7764-50-3 | ACGIJKL |
| 447 | Dihydro-alpha-terpinyl acetate | 80-25-1 | BDEFHIJKL |
| 448 | Dihydro-alpha-ionone | 31499-72-6 | BDHIJK |
| 454 | Dibenzyl ether | 103-50-4 | DEFHJK |
| 455 | Dibutyl o-phthalate | 84-74-2 | DEFHJ |
| 469 | 2-pentylcyclopentan-1-one | 4819-67-4 | BDFHIKL |
| 472 | Decyl anthranilate | 18189-07-6 | DEFHJ |
| 477 | Methyl (1s,4s)-1,4-dimethylcyclohexane-1-carboxylate | 23059-38-3 | ADEFHIJKL |
| 481 | Cyclohexylethyl acetate | 21722-83-8 | BDEFHJKL |
| 492 | Creosol | 93-51-6 | BCHIK |
| 495 | Cosmene | 460-01-5 | ADEFGIKL |
| 496 | 4-cyclohexyl-2-methylbutan-2-ol | 83926-73-2 | BDEFGIJK |
| 504 | 2-benzyl-2-methylbut-3-enenitrile | 97384-48-0 | BDHJK |
| 509 | Citronellyl nitrile | 51566-62-2 | BCEFGIKL |
| 510 | Citronellyl phenylacetate | 139-70-8 | DFHJ |
| 512 | Citronellyl formate | 105-85-1 | BCEFGJKL |
| 515 | Citronellyl benzoate | 10482-77-6 | DFHJ |
| 517 | Citronellol | 106-22-9 | BCHIJKL |
| 518 | Citronellal | 106-23-0 | ACHIJKL |
| 522 | Citral | 5392-40-5 | ACHIKL |
| 525 | cis-Pinane | 6876-13-7 | ADEFGIJKL |
| 526 | (Z)-3-methyl-2-(pent-2-en-1-yl)cyclopent-2-en-1-one | 488-10-8 | BCHIJKL |
| 528 | cis-iso-Eugenol | 5912-86-7 | CEFHIK |
| 535 | cis-3-Hexenyl valerate | 35852-46-1 | BDEFHJKL |
| 536 | cis-3-Hexenyl tiglate | 67883-79-8 | BDEFHJK |
| 538 | cis-3-Hexenyl propionate | 33467-74-2 | ACEFHIKL |
| 540 | cis-3-Hexenyl butyrate | 16491-36-4 | ADEFHJKL |
| 542 | cis-3-Hexen-1-ol | 928-96-1 | ACEFHIKL |
| 547 | cis-2-Hexenol | 928-94-9 | ACEFHIKL |
| 549 | Cinnamyl nitrile | 4360-47-8 | ACEFGIK |
| 554 | Cinnamic aldehyde | 104-55-2 | ACHIK |
| 556 | Cinnamyl nitrile | 1885-38-7 | ACEFGIK |
| 557 | Chloroxylenol | 88-04-0 | BCHIJK |
| 575 | Carvacrol | 499-75-2 | DHIJK |
| 576 | Carvone | 99-49-0 | ACGIJKL |
| 579 | Carbitol | 111-90-0 | BCEFGIK |
| 583 | Caproyl alcohol | 111-27-3 | ACEFGIKL |
| 585 | 2-(2,2,3-trimethylcyclopent-3-en-1-yl)acetonitrile | 15373-31-6 | ACGIJKL |
| 588 | Camphor | 76-22-2 | ACEFGIJKL |
| 602 | (E)-2-methyl-4-(2,6,6-trimethylcyclohex-1-en-1-yl)but-2-enal | 3155-71-3 | DHJK |
| 605 | Borneol | 507-70-0 | ACEFHIJKL |
| 617 | beta-Pinene epoxide | 6931-54-0 | ACEFGIJKL |
| 619 | beta-Phellandrene | 555-10-2 | ADEFGIJKL |
| 640 | Benzylacetone | 2550-26-7 | ACEFGIK |
| 641 | Benzyl salicylate | 118-58-1 | DFGJ |
| 645 | Benzyl isovalerate | 103-38-8 | BDEFHJK |
| 647 | Benzyl isobutyrate | 103-28-6 | BCHJK |
| 651 | Benzyl butyrate | 103-37-7 | BCEFHJK |
| 652 | Benzyl alcohol | 100-51-6 | ACEFGIKL |
| 662 | 1-(3,3-dimethylcyclohexyl)ethyl formate | 25225-08-5 | ADEFHIJKL |
| 664 | Anisyl acetate | 104-21-2 | BCEFGK |
| 665 | Anisyl formate | 122-91-8 | BCEFGK |
| 667 | Anethole | 104-46-1 | ACEFHK |
| 672 | Amyl benzoate | 2049-96-9 | DEFHJK |

TABLE 3-continued

| List of materials with at least one MORV from 0.5 to less than 1 | | | |
|---|---|---|---|
| Number | Material Name | CAS Number | Comment Code |
| 687 | alpha-Terpinyl acetate | 80-26-2 | BDHJK |
| 699 | alpha-methyl-cyclohexanepropanol | 10528-67-3 | BDEFHIK |
| 701 | alpha-methyl cinnamaldehyde | 101-39-3 | ACHIK |
| 703 | alpha-Isomethylionone | 127-51-5 | BDHIJK |
| 740 | 2,5-Dimethyl-4-methoxy-3(2H)-furanone | 4077-47-8 | ACEFGIJKL |
| 743 | Allyl phenoxyacetate | 7493-74-5 | BCGK |
| 744 | Allyl Phenethyl ether | 14289-65-7 | ACEFHK |
| 745 | Allyl heptanoate | 142-19-8 | ADEFHJKL |
| 755 | N-ethyl-N-(m-tolyl)propionamide | 179911-08-1 | CEFHJK |
| 760 | 3-hydroxybutan-2-one | 513-86-0 | ACEFGIKL |
| 761 | Acetoanisole | 100-06-1 | BCEFHIK |
| 777 | 6-Methylquinoline | 91-62-3 | BCEFHIKL |
| 779 | 6,8-Diethyl-2-nonanol | 70214-77-6 | BDEFGIJKL |
| 784 | 5-Methyl-3-heptanone | 541-85-5 | ACFGIKL |
| 789 | 4-Vinylphenol | 2628-17-3 | BCHIK |
| 796 | 4-hydroxy-3-methoxy-cinnamaldehyde | 458-36-6 | CH |
| 797 | 4-Ethylguaiacol | 2785-89-9 | CEFHIK |
| 799 | 4-Damascol | 4927-36-0 | BDFHJK |
| 808 | 3-methyl-4-phenylpyrazole | 13788-84-6 | CEFHK |
| 810 | 3-Methyl-1,2-cyclopentanedione | 765-70-8 | ACEFGIKL |
| 811 | 3-Methoxy-5-methylphenol | 3209-13-0 | BCHIK |
| 812 | 3-Methoxy-3-Methyl Butanol | 56539-66-3 | ACGIKL |
| 817 | 3-Hexenol | 544-12-7 | ACEFHIKL |
| 819 | 3,7-dimethyl-2-methylene-6-octenal | 22418-66-2 | ADFHIJK |
| 820 | 3,7-dimethyl-1-octanol | 106-21-8 | BDEFGIJKL |
| 832 | 2-Phenylethyl acetate | 103-45-7 | BCEFHK |
| 835 | 2-Phenethyl propionate | 122-70-3 | BCEFHJK |
| 836 | 2-Pentylcyclopentan-1-ol | 84560-00-9 | DEFHIKL |
| 838 | 2-nonanone propylene glycol acetal | 165191-91-3 | BDEFHJK |
| 845 | 2-Methoxy-3-(1-methylpropyl)pyrazine | 24168-70-5 | BCEFGIK |
| 846 | 2-isopropyl-N,2,3-trimethylbutyramide | 51115-67-4 | ACEFGIJK |
| 847 | 2-Isopropyl-5-methyl-2-hexenal | 35158-25-9 | ADFGIJKL |
| 848 | 2-Isopropyl-4-methylthiazole | 15679-13-7 | ACHIJKL |
| 851 | 2-Hexen-1-ol | 2305-21-7 | ACEFHIKL |
| 858 | 2-Butoxyethanol | 111-76-2 | ACEFGIKL |
| 875 | 1,4-Cineole | 470-67-7 | ADGIJKL |
| 880 | 1-(2,6,6-Trimethyl-2-cyclohexen-1-yl)-2-buten-1-one | 43052-87-5 | BDHIJK |
| 882 | (Z)-3-hepten-1-yl acetate | 1576-78-9 | ACEFHKL |
| 883 | (S)—(1R,5R)-4,6,6-trimethylbicyclo[3.1.1]hept-3-en-2-one | 1196-01-6 | ACEFGIJKL |
| 888 | (R)-(−)-Linalool | 126-91-0 | BCEFGIJK |
| 889 | (l)-Citronellal | 5949-05-3 | ACHIJKL |
| 891 | (d)-Citronellal | 2385-77-5 | ACHIJKL |
| 899 | (+)-Citronellol | 1117-61-9 | BCHIJKL |
| 900 | (−)-Citronellol | 7540-51-4 | BCHIJKL |
| 901 | (+)-alpha-Pinene | 7785-70-8 | ADEFGIJKL |
| 902 | (+)-Carvone | 2244-16-8 | ACGIJKL |
| 903 | (−)-alpha-Pinene | 7785-26-4 | ADEFGIJKL |
| 904 | Methyl 2-methylbutyrate | 868-57-5 | ACEFGIKL |
| 909 | Hexyl tiglate | 16930-96-4 | BDEFHJKL |
| 918 | Allyl 2-(cyclohexyloxy)acetate | 68901-15-5 | CHJK |
| 921 | 1,5-dimethylbicyclo[3.2.1]octan-8-one oxime | 75147-23-8 | CFHIJK |
| 931 | alpha-acetoxystyrene | 2206-94-2 | ACEFHIK |
| 940 | p-Cymene | 99-87-6 | ADGIJKL |
| 956 | Phenethyl formate | 104-62-1 | ACEFHK |
| 958 | Phenethyl isobutyrate | 103-48-0 | DHJK |
| 960 | Phenethyl tiglate | 55719-85-2 | DHJK |
| 971 | Phenylethyl methacrylate | 3683-12-3 | DHJK |
| 977 | p-Isopropylphenylacetaldehyde | 4395-92-0 | BDFHK |

TABLE 3-continued

| List of materials with at least one MORV from 0.5 to less than 1 | | | |
|---|---|---|---|
| Number | Material Name | CAS Number | Comment Code |
| 981 | 1,2-dimethyl-3-(prop-1-en-2-yl)cyclopentan-1-ol | 72402-00-7 | BCEFGIJKL |
| 983 | p-Methoxyphenylacetone | 122-84-9 | BCEFHK |
| 986 | (2Z,5Z)-5,6,7-trimethylocta-2,5-dien-4-one | 358331-95-0 | ADHIJKL |
| 987 | p-Propyl anisole | 104-45-0 | ADEFHKL |
| 994 | p-t-butyl phenyl acetaldehyde | 109347-45-7 | BDHJK |
| 995 | p-tert-Amyl cyclohexanol | 5349-51-9 | BDEFHIJK |
| 1001 | Racemic alpha-Pinene | 80-56-8 | ADEFGIJKL |
| 1002 | 4-(4-hydroxyphenyl)butan-2-one | 5471-51-2 | CEFGIK |
| 1004 | Rhodinol | 141-25-3 | BCHIJKL |
| 1005 | Ethyl (2,3,6-trimethylcyclohexyl)carbonate | 93981-50-1 | BDEFHJKL |
| 1011 | 1-(3,3-dimethylcyclohexyl)ethyl acetate | 25225-10-9 | ADHIJKL |
| 1017 | S)-(+)-Linalool | 126-90-9 | BCEFGIJK |
| 1018 | Sabinene | 3387-41-5 | ADEFGIJKL |
| 1019 | Sabinene hydrate | 546-79-2 | ADEFGIJKL |
| 1030 | Propyl (S)-2-(tert-pentyloxy)propanoate | 319002-92-1 | BDEFHJK |
| 1039 | Spirolide | 699-61-6 | BCGIKL |
| 1040 | (Z)-5-methylheptan-3-one oxime | 22457-23-4 | BCEFGIJKL |
| 1041 | 1-phenylethyl acetate | 93-92-5 | ACEFHIK |
| 1051 | Tetrahydrogeranial | 5988-91-0 | ADGIJKL |
| 1052 | Tetrahydroionol | 4361-23-3 | BDEFHIJK |
| 1054 | Tetrahydrolinalool | 78-69-3 | BDEFGIJKL |
| 1055 | Tetrahydrolinalyl acetate | 20780-48-7 | ADEFHJKL |
| 1058 | Ethyl (1R,6S)-2,2,6-trimethylcyclohexane-1-carboxylate | 22471-55-2 | ADEFHIJKL |
| 1061 | Thymol | 89-83-8 | BDHIJK |
| 1069 | trans-2-Hexenol | 928-95-0 | ACEFHIKL |
| 1071 | trans-2-tert-Butylcyclohexanol | 5448-22-6 | ACGIJKL |
| 1074 | trans-alpha-Damascone | 24720-09-0 | BDHIJK |
| 1076 | trans-Anethole | 4180-23-8 | ACEFHK |
| 1079 | trans-Cinnamic acid | 140-10-3 | CEFHK |
| 1081 | trans-Dihydrocarvone | 5948-04-9 | ACGIJKL |
| 1084 | trans-Isoeugenol | 5932-68-3 | CEFHIK |
| 1088 | Trichloromethyl phenyl carbinyl acetate | 90-17-5 | BDEFGJ |
| 1098 | 2-mercapto-2-methylpentan-1-ol | 258823-39-1 | ACEFHIJKL |
| 1110 | Vanillin acetate | 881-68-5 | CH |
| 1112 | Vanitrope | 94-86-0 | CEFHK |
| 1115 | 2,2,5-trimethyl-5-pentylcyclopentan-1-one | 65443-14-3 | BDFGIJKL |
| 1118 | Veratraldehyde | 120-14-9 | BCGIK |
| 1119 | (1R,5R)-4,6,6-trimethylbicyclo[3.1.1]hept-3-en-2-one | 18309-32-5 | ACEFGIJKL |
| 1122 | Verdol | 13491-79-7 | ACGIJKL |
| 1127 | 4-(tert-butyl)cyclohexyl acetate | 10411-92-4 | BDEFHJK |
| 1128 | 4-(tert-butyl)cyclohexyl acetate | 32210-23-4 | BDEFHJK |
| 1133 | Vethymine | 7193-87-5 | CEFGK |
| 1134 | 4-methyl-4-phenylpentan-2-yl acetate | 68083-58-9 | BDFHJK |
| 1141 | (Z)-1-((2-methylallyl)oxy)hex-3-ene | 292605-05-1 | ADEFHKL |

TABLE 4

| List of malodor reduction materials with ALL MORVs from 1 to 5 | | | |
|---|---|---|---|
| Number | Material Name | CAS Number | Comment Code |
| 7 | 3-methoxy-7,7-dimethyl-10-methylenebicyclo[4.3.1]decane | 216970-21-7 | BDEFHJK |

TABLE 4-continued

| List of malodor reduction materials with ALL MORVs from 1 to 5 | | | |
|---|---|---|---|
| Number | Material Name | CAS Number | Comment Code |
| 14 | Oxyoctaline formate | 65405-72-3 | DFHJK |
| 39 | 2,2,6,8-tetramethyl-1,2,3,4,4a,5,8,8a-octahydro-naphthalen-1-ol | 103614-86-4 | DEFHIJK |
| 48 | Nootkatone | 4674-50-4 | DHJK |
| 183 | Khusimol | 16223-63-5 | CEFHJK |
| 199 | Isopimpinellin | 482-27-9 | CFGJ |
| 206 | Iso3-methylcyclopentadecan-1-one | 3100-36-5 | DEFGJK |
| 212 | Isoeugenyl benzyl ether | 120-11-6 | DFHJ |
| 215 | 1-((2S,3S)-2,3,8,8-tetramethyl-1,2,3,4,5,6,7,8-octahydro-naphthalen-2-yl)ethan-1-one | 54464-57-2 | DHJK |
| 229 | Isobornyl isobutyrate | 85586-67-0 | BDEFHIJK |
| 260 | 2,3-dihydro-3,3-dimethyl-1H-indene-5-propanal | 173445-44-8 | DHJK |
| 261 | 3-(3,3-dimethyl-2,3-dihydro-1H-inden-5-yl)propanal | 173445-65-3 | DHJK |
| 281 | 3a,4,5,6,7,7a-hexahydro-1H-4,7-methanoinden-6-yl acetate | 5413-60-5 | CEFGJK |
| 329 | gamma-Eudesmol | 1209-71-8 | DFHJK |
| 335 | 4,6,6,7,8,8-hexamethyl-1,3,4,6,7,8-hexahydro-cyclopenta[g]isochromene | 1222-05-5 | DEFHJK |
| 353 | (Z)-6-ethylideneoctahydro-2H-5,8-methanochromen-2-one | 69486-14-2 | CEFGJK |
| 360 | 8,8-dimethyl-3a,4,5,6,7,7a-hexahydro-1H-4,7-methanoinden-6-yl acetate | 171102-41-3 | DEFHJK |
| 441 | Octahydro-1H-4,7-methanoinden-5-yl acetate | 64001-15-6 | DEFHJKL |
| 484 | 3a,4,5,6,7,7a-hexahydro-1H-4,7-methanoinden-6-yl butyrate | 113889-23-9 | DEFHJK |
| 487 | 3a,4,5,6,7,7a-hexahydro-1H-4,7-methanoinden-5-yl isobutyrate | 67634-20-2 | DEFHJK |
| 488 | Curzerene | 17910-09-7 | DHJK |
| 501 | (E)-cycloheptadec-9-en-1-one | 542-46-1 | DEFGJ |
| 566 | Cedryl formate | 39900-38-4 | BDEFHJK |
| 567 | Cedryl acetate | 77-54-3 | DEFHJK |
| 569 | Cedrol | 77-53-2 | DEFHJK |
| 570 | 5-methyl-1-(2,2,3-trimethylcyclopent-3-en-1-yl)-6-oxabicyclo[3.2.1]octane | 139539-66-5 | DEFHJK |
| 573 | Caryophyllene alcohol acetate | 32214-91-8 | DEFHJK |
| 574 | Caryolan-1-ol | 472-97-9 | DEFHJK |
| 603 | Bornyl isobutyrate | 24717-86-0 | BDEFHIJK |
| 616 | beta-Santalol | 77-42-9 | DEFHJK |
| 621 | beta-Patchoulline | 514-51-2 | BDEFGJKL |
| 624 | beta-Himachalene Oxide | 57819-73-5 | BDFHJK |
| 627 | (2,2-dimethoxyethyl)benzene | 101-48-4 | DHJK |
| 632 | beta-Cedrene | 546-28-1 | BDEFGJKL |
| 663 | Anisyl phenylacetate | 102-17-0 | DFHJ |
| 680 | 2,2,6,6,7,8,8-heptamethyldeca-hydro-2H-indeno[4,5-b]furan | 647828-16-8 | ADEFHJK |
| 684 | alpha-Vetivone | 15764-04-2 | DHJK |
| 694 | alpha-Santalol | 115-71-9 | DEFHJK |
| 696 | alpha-Patchoulene | 560-32-7 | ADEFHJKL |
| 708 | alpha-Gurjunene | 489-40-7 | BDEFHJKL |
| 712 | alpha-Eudesmol | 473-16-5 | DEFHJK |
| 714 | alpha-Cubebene | 17699-14-8 | ADEFHJKL |
| 726 | alpha-Agarofuran | 5956-12-7 | BDEFHJK |
| 750 | Allo-aromadendrene | 25246-27-9 | BDEFHJKL |
| 764 | Acetarolle | 744266-61-3 | DFHJK |
| 775 | 7-eip-alpha-Eudesmol | 123123-38-6 | DEFHJK |
| 776 | 7-Acetyl-1,1,3,4,4,6-hexamethyltetralin | 1506-02-1 | DEFHJ |
| 788 | 5-Cyclohexadecenone | 37609-25-9 | DEFGJK |
| 804 | 3-Thujopsanone | 25966-79-4 | BDEFHJK |
| 872 | 10-epi-gamma-Eudesmol | 15051-81-7 | DFHJK |
| 919 | 3a,4,5,6,7,7a-hexahydro-1H-4,7-methanoinden-6-yl propionate | 17511-60-3 | CEFHJK |
| 927 | 5-Acetyl-1,1,2,3,3,6-hexamethylindan | 15323-35-0 | DEFHJK |
| 933 | Patchouli alcohol | 5986-55-0 | DEFHIJK |
| 978 | 3a,4,5,6,7,7a-hexahydro-1H-4,7-methanoinden-6-yl pivalate | 68039-44-1 | DEFHJK |

TABLE 4-continued

List of malodor reduction materials with ALL MORVs from 1 to 5

| Number | Material Name | CAS Number | Comment Code |
|---|---|---|---|
| 1007 | (2R,4a'R,8a'R)-3,7'-dimethyl-3',4',4a',5',8',8a'-hexahydro-1'H-spiro[oxirane-2,2'-[1,4]methanonaphthalene] | 41816-03-9 | DEFHJK |
| 1022 | 2,2,7,9-tetramethylspiro(5.5)undec-8-en-1-one | 502847-01-0 | DHIJK |
| 1024 | (Z)-2-ethyl-4-(2,2,3-trimethylcyclopent-3-en-1-yl)but-2-en-1-ol | 28219-61-6 | DEFHJK |
| 1027 | 5-methoxyoctahydro-1H-4,7-methanoindene-2-carbaldehyde | 193425-86-4 | CHJK |
| 1029 | Sclareol oxide | 5153-92-4 | DEFHJK |
| 1035 | Spathulenol | 6750-60-3 | DEFHJK |
| 1038 | 1-(spiro[4.5]dec-7-en-7-yl)pent-4-en-1-one | 224031-70-3 | DGJK |
| 1060 | Thujopsene | 470-40-6 | BDEFGJKL |
| 1089 | Tricyclone | 68433-81-8 | DEFHJK |
| 1107 | Valerianol | 20489-45-6 | DEFHJK |
| 1129 | 1-((3R,3aR,7R,8aS)-3,6,8,8-tetramethyl-2,3,4,7,8,8a-hexahydro-1H-3a,7-methanoazulen-5-yl)ethan-1-one | 32388-55-9 | DHJK |
| 1131 | Methyl (Z)-2-(((2,4-dimethylcyclohex-3-en-1-yl)methylene)amino)benzoate | 68738-99-8 | DEFHJ |
| 1136 | Vetivert Acetate | 117-98-6 | DEFHJK |
| 1137 | Decahydro-3H-spiro[furan-2,5'-[4,7]methanoindene] | 68480-11-5 | DEFGJKL |
| 1140 | (1aR,4S,4aS,7R,7aS,7bS)-1,1,4,7-tetramethyldecahydro-1H-cyclopropa[e]azulen-4-ol | 552-02-3 | DEFHJK |
| 1142 | 3,5,5,6,7,8,8-heptamethyl-5,6,7,8-tetrahydronaphthalene-2-carbonitrile | 127459-79-4 | DHJ |
| 1143 | (1S,2S,3S,5R)-2,6,6-trimethylspiro[bicyclo[3.1.1]-heptane-3,1'-cyclohexan]-2'-en-4'-one | 133636-82-5 | DEFHJK |
| 1144 | 1',1',5',5'-tetramethylhexahydro-2'H,5'H-spiro[[1,3]dioxolane-2,8'-[2,4a]methanonaphthalene] | 154171-76-3 | DEFHJK |
| 1145 | 1',1',5',5'-tetramethylhexahydro-2'H,5'H-spiro[[1,3]dioxolane-2,8'-[2,4a]methanonaphthalene] K | 154171-77-4 | DEFHJK |
| 1148 | 4,5-epoxy-4,11,11-trimethyl-8-methylenebicyclo(7.2.0)undecane | 1139-30-6 | DEFHJK |
| 1149 | 1,3,4,6,7,8alpha-hexahydro-1,1,5,5-tetramethyl-2H-2,4alpha-methanophtalen-8(5H)-one | 23787-90-8 | DEFHIJK |

TABLE 5

List of malodor reduction materials with ALL MORVs greater than 5 to 10

| Number | Material Name | CAS Number | Comment Code |
|---|---|---|---|
| 248 | Hydroxymethyl isolongifolene | 59056-64-3 | BDEFHJK |

TABLE 6

List of malodor reduction materials with ALL MORVs from 0.5 to less than 1

| Number | Material Name | CAS Number | Comment Code |
|---|---|---|---|
| 472 | Decyl anthranilate | 18189-07-6 | DEFHJ |
| 526 | (Z)-3-methyl-2-(pent-2-en-1-yl)cyclopent-2-en-1-one | 488-10-8 | BCHIJKL |

The materials in Tables 1-6 can be supplied by one or more of the following:

Firmenich Inc. of Plainsboro N.J. USA; International Flavor and Fragrance Inc. New York, N.Y. USA; Takasago Corp. Teterboro, N.J. USA; Symrise Inc. Teterboro, N.J. USA; Sigma-Aldrich/SAFC Inc. Carlsbad, Calif. USA; and Bedoukian Research Inc. Danbury, Conn. USA.

Actual MORV values for each material listed in Tables 1-6 above are as follows:

| Material No. | MORV value for Equation a.) | MORV Value for Equation b.) | MORV Value for Equation c.) | MORV value for Equation d.) |
|---|---|---|---|---|
| 1 | 0.548223914 | 0.876283261 | 1.22018588 | −0.41901144 |
| 2 | 1.520311929 | 3.493450446 | 2.70657265 | 5.11342862 |
| 3 | 2.267801995 | −0.81712657 | 0.43218875 | 1.595983683 |
| 4 | −0.591063369 | −0.48283571 | 0.16199804 | 1.210497701 |
| 7 | 1.437444636 | 2.131822996 | 3.81633465 | 1.318339345 |
| 9 | 2.151445882 | −0.46189495 | 0.56090469 | 1.206360803 |
| 10 | 2.5733592 | −0.58780849 | 1.39751471 | 1.258361951 |
| 11 | 3.052627325 | 1.008519135 | −0.30475953 | 0.076323462 |
| 12 | 0.683776599 | −0.01157903 | 0.82853231 | 0.326169402 |
| 13 | 1.549643217 | 1.809183231 | 0.70864531 | 2.22799611 |
| 14 | 2.82111224 | 2.339505033 | 1.240818 | 2.502429355 |
| 16 | −0.31551128 | −0.06816599 | −0.04371934 | 2.76742389 |
| 17 | −1.334904153 | −0.5773313 | 1.75644798 | 1.898455724 |
| 18 | −1.34154226 | −2.63596666 | 0.06885109 | 1.001431671 |
| 19 | 0.15532384 | 0.09866097 | 0.64214585 | −0.33330779 |
| 20 | 0.640261783 | 0.693213268 | 0.54637273 | −0.97556029 |
| 21 | 0.936895364 | −0.01521118 | 1.1697513 | −0.63510809 |
| 22 | 1.158981042 | 1.115900089 | −0.25859776 | 1.318200884 |
| 23 | 3.702361074 | 1.399942641 | 5.23954766 | 7.089933671 |
| 24 | 0.773874141 | 0.146848137 | −1.05705847 | −0.36193173 |
| 25 | −1.016103969 | −1.18967936 | 0.78064625 | 2.944710012 |
| 25 | −1.016103969 | −1.18967936 | 0.78064625 | 2.944710012 |
| 26 | 0.615085491 | −0.00096877 | −0.35697252 | −0.18121401 |
| 27 | 0.70261974 | −0.22197386 | 0.19710806 | −2.37196477 |
| 28 | 1.366472597 | −0.42546942 | −0.59394241 | −0.01417395 |
| 29 | 1.096043453 | −1.02972898 | −1.42167356 | −0.63817943 |
| 30 | 1.143415203 | −0.85945441 | −0.41416913 | 2.499807942 |
| 31 | 1.138642907 | −0.19595476 | −0.54547769 | −0.98828898 |
| 32 | 1.914414495 | −0.64487788 | 0.63212987 | 1.166699371 |
| 33 | 0.314847366 | 1.848003955 | −1.3905032 | −0.62848261 |
| 34 | −0.113542761 | 0.981530917 | 0.32824239 | 1.126524277 |
| 35 | 0.472382903 | 1.494882467 | −0.07201236 | −0.64589543 |
| 36 | 3.158513795 | 1.084094934 | −0.00328981 | −0.17786385 |
| 37 | −1.055631982 | 2.240172964 | 0.92596118 | 2.105391988 |
| 38 | 3.158513795 | 0.592820874 | −0.49326241 | 0.212867212 |
| 39 | 1.083800659 | 2.069727985 | 2.48170879 | 3.205630609 |
| 42 | −0.103134861 | 0.267726008 | −0.65350189 | 1.125952363 |
| 43 | 0.323961628 | 1.469295081 | −0.52991193 | 0.797908251 |
| 47 | 1.703678841 | 1.348737095 | 2.00634162 | −0.16505407 |
| 48 | 2.370955056 | 2.783472865 | 2.68240273 | 1.221864405 |
| 49 | 1.670680003 | −0.41866107 | −0.9173849 | 1.181929544 |
| 50 | 1.670680003 | 0.076369374 | −0.49915943 | −0.85392575 |
| 52 | 0.464485039 | 0.057512869 | 1.31230219 | −0.11170276 |
| 53 | 0.626671823 | −0.46954947 | −0.33383736 | 0.277079201 |
| 54 | 0.666149043 | 0.009549925 | −0.36226343 | 0.197224432 |
| 55 | 0.723473579 | −1.50916383 | −0.3848989 | −0.71458778 |
| 57 | 0.381273227 | 1.192994109 | 1.65593321 | −1.65739236 |
| 59 | 0.561360663 | −0.17793966 | −1.63250554 | −0.7564969 |
| 61 | 0.146473611 | −0.01535544 | −0.16339658 | 1.738656146 |
| 62 | 1.20162032 | −0.3576095 | −0.10695443 | 1.322155191 |
| 63 | 1.084291915 | 2.258720158 | −1.01245416 | 1.688283974 |
| 64 | 0.744770665 | 0.155243763 | −1.8029919 | 1.023503542 |
| 65 | 0.972835178 | 2.797151284 | 1.53453579 | 0.857051645 |
| 67 | 2.069410561 | 0.021831924 | 0.37855159 | −0.67235457 |
| 68 | 0.527636614 | 0.590831983 | 1.02843762 | 2.208655795 |
| 69 | 2.133965691 | 2.088998449 | 2.05751412 | −0.9433713 |
| 70 | 0.327378959 | 0.996844599 | 1.23648533 | −1.25138371 |
| 71 | 1.40093669 | 0.778222691 | 0.70401172 | −0.24075444 |
| 72 | 0.617697349 | −0.29503359 | 0.52404847 | 0.816184656 |
| 73 | 0.617792473 | 0.888976061 | −0.45289639 | 0.615659244 |
| 74 | 1.437359024 | 1.548292147 | 0.10314807 | −0.48982286 |
| 75 | −1.970885622 | 3.398008325 | 4.08025266 | −0.89948156 |
| 76 | −1.32746934 | −2.65365233 | 0.10272816 | 1.001614125 |
| 77 | −2.541686116 | 3.295534192 | 3.75284227 | 0.404837808 |
| 78 | −2.110794 | 2.109874746 | 3.13350902 | −0.3880285 |

-continued

| Material No. | MORV value for Equation a.) | MORV Value for Equation b.) | MORV Value for Equation c.) | MORV value for Equation d.) |
|---|---|---|---|---|
| 79 | 1.641162056 | −0.28533994 | 1.53676145 | 0.652696023 |
| 80 | 1.594400214 | 0.283682865 | 2.23140233 | 1.111682021 |
| 81 | 0.176566806 | −2.0786518 | −2.13986952 | 0.981126964 |
| 82 | 0.980373758 | −0.28813159 | 0.19404501 | 1.252564677 |
| 83 | 0.941833098 | 0.317310013 | 1.17606727 | 0.72992237 |
| 84 | 0.774237336 | −0.27140727 | 0.72461427 | −1.56415746 |
| 85 | 2.092976965 | 0.810644229 | 0.82999192 | −0.62861806 |
| 91 | 2.061595915 | −0.79930338 | −0.18285395 | −0.66898499 |
| 92 | 2.068748434 | −0.24299896 | 0.07214682 | −1.11758276 |
| 93 | −0.08984279 | −1.06025959 | −0.05068694 | 1.560050105 |
| 96 | 0.927758203 | −0.44129515 | 0.89190422 | 0.744284978 |
| 97 | 0.658667572 | −0.68771072 | 0.46051026 | −0.53120883 |
| 98 | 0.853222693 | −0.2037738 | −0.21414441 | 1.119784962 |
| 100 | 1.654535066 | 0.995056228 | 2.35139085 | 0.543654824 |
| 101 | 2.173663649 | −0.11491477 | 1.48285148 | 1.698527571 |
| 102 | 2.066679492 | −0.16785146 | −0.84780149 | 0.12159477 |
| 103 | 2.335152618 | −0.02866585 | 0.16993375 | −0.98254522 |
| 104 | 2.760588276 | 0.459513599 | 1.35310241 | 0.000336976 |
| 105 | 1.654535066 | 3.654489674 | 3.13033965 | 0.544225478 |
| 106 | 1.750588169 | −0.55853348 | 0.50257773 | 1.630011313 |
| 107 | 0.896789863 | 0.73615897 | 0.53011623 | −0.54697747 |
| 108 | 0.532375207 | 0.826537134 | 1.21040312 | 0.690230716 |
| 109 | 2.407655187 | 0.742651426 | 1.80322099 | 0.271832856 |
| 110 | 0.54830833 | 2.916795026 | 1.40126098 | 0.690230716 |
| 111 | 0.939597126 | −0.3750368 | −1.23479972 | −0.89366351 |
| 112 | 1.398518854 | 1.265740274 | 4.19618377 | −0.12762692 |
| 113 | 1.415726941 | 0.086297006 | 3.43559555 | −0.12964168 |
| 115 | −1.557729423 | −0.44113526 | 0.86330536 | 0.590708892 |
| 116 | 0.193562268 | −1.58091165 | 0.83247813 | −0.70978039 |
| 117 | 1.353510875 | −0.59062398 | −0.31776345 | −0.3050158 |
| 119 | 0.830052725 | 2.28725579 | 0.38409695 | 0.219336109 |
| 120 | 1.261997955 | −0.22622961 | −1.04772194 | 2.028504137 |
| 122 | 1.505653628 | −1.14748206 | −0.19760084 | −0.81373045 |
| 123 | −0.658721962 | −0.21299878 | 1.01439841 | −0.76731016 |
| 125 | 0.749676998 | −1.0761601 | 0.99563924 | −1.15409002 |
| 126 | 0.931054384 | −0.35067079 | 1.06050832 | −1.62171794 |
| 128 | −1.344832644 | −0.09451199 | 1.19145467 | 1.621274257 |
| 130 | 1.153249538 | 1.605070708 | 2.38047907 | −0.93842293 |
| 133 | 0.840066046 | 0.2323025 | 0.19054023 | −0.26588341 |
| 134 | 0.522267541 | 0.824106618 | 1.83479545 | 0.364403434 |
| 135 | 2.142817887 | 2.142411243 | −0.93830995 | 0.696522652 |
| 137 | 3.052627325 | 3.606270166 | 0.50445208 | 0.076323462 |
| 140 | −0.153437637 | 0.246303216 | 0.76565758 | 1.800968868 |
| 141 | 2.067620311 | 1.424830396 | 2.33536931 | 7.644025075 |
| 142 | 0.98353103 | 1.950251373 | 2.50851828 | −0.24499521 |
| 143 | 1.736969725 | 0.991537809 | 2.5691601 | 1.227191656 |
| 145 | −0.211768579 | 1.46336231 | −0.93580247 | −1.48749449 |
| 146 | 1.912710035 | 0.926306508 | 1.81253333 | 0.494121361 |
| 147 | 0.675736703 | 0.99202385 | −0.66034472 | −0.66302669 |
| 148 | 0.757176542 | 1.83006252 | 0.16210659 | 0.243674851 |
| 149 | 0.438772371 | 1.091438092 | −0.1560319 | −0.61711642 |
| 150 | 0.84399938 | 0.675302022 | −1.69771411 | −0.73841711 |
| 151 | 0.633570539 | 0.988413715 | −0.54991825 | −0.43550324 |
| 152 | 0.911582356 | 1.974700218 | −0.92267786 | 0.628660087 |
| 153 | 0.319053885 | 2.531735341 | −0.39139184 | 0.734629224 |
| 154 | 0.714814512 | 0.690769753 | −2.06588692 | −0.73356628 |
| 155 | −0.161798388 | 0.032135767 | −0.13802086 | 1.734928461 |
| 156 | −0.571799976 | −1.32834264 | −1.65346017 | 1.856689553 |
| 157 | 0.131224024 | 0.21510779 | −1.70996346 | 0.964902175 |
| 158 | 1.201616145 | −0.21158932 | −0.8501176 | −0.33330779 |
| 159 | 0.811289908 | 1.606645397 | 0.25352447 | −1.83775117 |
| 159 | 0.811289908 | 1.606645397 | 0.25352447 | −1.83775117 |
| 161 | 0.475184006 | 1.99305646 | 1.90910177 | 3.288337059 |
| 162 | 0.833030517 | 0.487189028 | 1.76798642 | 0.104378164 |
| 163 | 0.58993703 | −0.46431772 | 0.74883588 | −0.81090824 |
| 166 | −0.121286831 | −0.84664528 | −0.32625341 | 0.778055656 |
| 167 | 0.846400186 | −0.25922232 | 0.69248774 | 1.183696217 |
| 168 | −0.310930833 | −0.81048493 | 0.08527131 | 1.61831109 |
| 169 | −0.2346025 | 0.890438419 | −0.13206526 | −0.83961838 |
| 170 | −0.169223695 | 1.172917966 | −0.11306441 | 0.099121666 |
| 174 | 2.863652137 | 0.236674094 | −0.69038707 | 1.610215283 |
| 175 | 1.789769228 | −0.31740428 | −0.89529921 | −0.09686469 |
| 176 | 2.625947334 | 0.083548191 | 0.30634559 | −0.35925728 |
| 177 | 1.674319352 | −0.22179044 | 0.42093738 | −0.23683577 |
| 178 | 2.863652137 | 0.727069168 | −0.26724686 | −0.44888613 |

-continued

| Material No. | MORV value for Equation a.) | MORV Value for Equation b.) | MORV Value for Equation c.) | MORV value for Equation d.) |
|---|---|---|---|---|
| 179 | 0.070511885 | 0.365852864 | 1.35327505 | −0.03748038 |
| 181 | 0.976254543 | 0.691638796 | 0.51371978 | −0.02503945 |
| 182 | −1.842503751 | −0.12688474 | 2.56277877 | 0.111744488 |
| 183 | 3.195758563 | 3.886545621 | 4.29482769 | 3.829845293 |
| 184 | 0.333889534 | −0.67236766 | 2.21605977 | 4.254612125 |
| 185 | 5.61162203 | 1.40458529 | 2.86231343 | 1.035135749 |
| 186 | 1.068190511 | −0.65969343 | −0.63104765 | −1.36962992 |
| 187 | 1.396358739 | 0.249705611 | 0.81449499 | −0.15353102 |
| 189 | 1.544466636 | −0.33742685 | 0.8096674 | −0.44483677 |
| 190 | −0.210918777 | −1.04086063 | 0.02614862 | 3.362615492 |
| 191 | 0.715897301 | 0.666316436 | −0.41719538 | 0.400723176 |
| 192 | 0.65612864 | 1.231196814 | 0.75462061 | 1.514581532 |
| 193 | −0.394884432 | 1.129269425 | −0.3157071 | −0.61478944 |
| 194 | −2.111794245 | −0.71010521 | 0.53077207 | 0.59302222 |
| 195 | 1.18880856 | 0.704463775 | 1.99312777 | 1.419709023 |
| 196 | 1.885714606 | 0.436434665 | 1.44657532 | 1.145809063 |
| 197 | 2.174580668 | 0.133070149 | 0.99814905 | 0.871658496 |
| 198 | −0.533922573 | −2.16213117 | 0.5812107 | −0.92280453 |
| 199 | 1.493919434 | 1.45125612 | 1.95141371 | 4.403441058 |
| 201 | −0.005520296 | −0.83362523 | 0.65480762 | −0.38894276 |
| 204 | 0.732981164 | −0.97494758 | −0.91192246 | −1.00034323 |
| 205 | 0.991838899 | −0.60053505 | −0.49983634 | 0.674468753 |
| 206 | 2.147983695 | 1.291351958 | 1.64553247 | 1.626455601 |
| 208 | −0.386224123 | −0.24799559 | 1.19406353 | −1.61243489 |
| 209 | 1.447075297 | 0.122626462 | 1.08021156 | 0.473154634 |
| 210 | −0.386224123 | −0.24799559 | 1.19406353 | −1.61243489 |
| 211 | 2.186118467 | 1.873949371 | 0.64852028 | −0.59205851 |
| 212 | 1.367811201 | 1.689658923 | 1.8017376 | 2.525531645 |
| 213 | 0.925016223 | 0.875610609 | 0.31462609 | 0.847028648 |
| 214 | −0.239873321 | 1.808823425 | −0.36105512 | −0.07650286 |
| 215 | 2.264275088 | 1.360001278 | 3.25759951 | 2.147928282 |
| 218 | −0.509585598 | −0.93428643 | 1.63030386 | −0.79436377 |
| 221 | 1.876297063 | 0.026873469 | 0.45442758 | 1.538486988 |
| 227 | 5.317676982 | 2.824566654 | 1.73360625 | 3.103310061 |
| 228 | 3.323728685 | 1.554268023 | 1.8883835 | 0.957527434 |
| 229 | 3.218950175 | 1.464118271 | 2.47512497 | 1.214429025 |
| 230 | 5.242356467 | 3.482206715 | 3.50441556 | 1.614847073 |
| 230 | 5.242356467 | 3.482206715 | 3.50441556 | 1.614847073 |
| 231 | 2.710087358 | 1.517756148 | 0.35088855 | 0.603171932 |
| 231 | 2.710087358 | 1.517756148 | 0.35088855 | 0.603171932 |
| 232 | 0.703604481 | 0.42129186 | 0.39567696 | 0.41729786 |
| 233 | 1.312921486 | 0.816597603 | 2.17066283 | 0.472801294 |
| 234 | 0.874145958 | 0.741410502 | 1.71105733 | −0.47289415 |
| 237 | 0.778921491 | −1.02119303 | 0.4612164 | −0.8881184 |
| 238 | 0.681403734 | −0.342052 | 1.27750286 | −0.3383341 |
| 239 | −0.870637933 | −2.58292907 | 0.79173772 | −1.27888846 |
| 242 | 0.910211214 | 0.374558101 | 1.01712685 | 1.001043471 |
| 243 | 1.670680003 | 0.104780951 | −0.6545574 | −0.46985154 |
| 244 | 1.140332181 | 0.116513028 | 1.61110902 | 3.713305291 |
| 246 | −0.634992987 | 0.548746912 | 4.62542427 | 7.660969857 |
| 247 | −1.739729444 | −0.91508372 | 1.18693162 | 3.108631198 |
| 248 | 5.81821686 | 6.320330665 | 6.14379552 | 5.214046447 |
| 249 | 0.348188924 | −0.95333461 | −0.08432225 | 1.866717393 |
| 252 | 2.456287983 | −0.02516176 | 0.76814124 | 1.756087132 |
| 253 | 1.76915226 | 0.226389981 | −0.18115009 | −0.62385199 |
| 254 | 0.658956861 | −0.39322197 | −0.67153044 | 1.416053304 |
| 255 | 0.892122738 | −0.46985097 | 0.42813903 | −0.46752753 |
| 256 | 0.625043963 | −0.65111806 | 1.4319541 | 2.110656697 |
| 258 | −0.187789327 | −0.85870492 | −0.21766971 | 0.931521178 |
| 259 | −1.261365139 | −2.33099427 | 1.33595129 | 0.43644676 |
| 260 | 2.4020693 | 2.669351733 | 2.36395771 | 1.910609499 |
| 261 | 1.978618006 | 2.732613301 | 2.19594212 | 1.683156477 |
| 263 | 1.350274014 | −0.59210334 | 0.14780643 | −0.13113746 |
| 264 | 0.526085484 | −1.54983116 | −0.17497208 | −0.8204696 |
| 267 | 1.175997006 | −1.03507906 | −0.11004734 | −0.50564806 |
| 269 | 2.367197222 | 0.457286256 | 0.02211231 | 0.497925297 |
| 270 | 0.711734628 | −1.45058685 | −0.17018094 | −0.71795736 |
| 271 | 1.073564668 | −0.47951936 | −0.80269361 | 0.136837431 |
| 273 | 0.663835001 | −1.5674675 | 0.28509522 | −1.12959038 |
| 274 | 1.628173498 | −0.58892922 | −0.3892777 | −0.66728139 |
| 275 | 0.935336765 | −0.9522644 | −0.87000279 | −0.29365972 |
| 276 | −5.989155804 | 1.722071272 | 3.31094703 | 1.273171428 |
| 277 | 0.904631703 | −1.02628534 | 0.49274649 | 1.000655271 |
| 278 | 0.293923493 | −0.82335619 | 0.13147975 | 2.730914048 |
| 280 | −0.284822555 | 0.322094188 | 3.2184015 | 0.383213731 |

-continued

| Material No. | MORV value for Equation a.) | MORV Value for Equation b.) | MORV Value for Equation c.) | MORV value for Equation d.) |
|---|---|---|---|---|
| 281 | 2.201373139 | 2.228820089 | 2.03455575 | 1.720697243 |
| 282 | 0.505189899 | −1.01844885 | −0.98499144 | 0.912195522 |
| 283 | 0.775002479 | −1.29876341 | −1.52162214 | −0.77292581 |
| 284 | 0.505189899 | −0.57830662 | −0.55673047 | −1.09870665 |
| 285 | −0.987611415 | 0.908212704 | 2.59089199 | 1.311154128 |
| 286 | −2.635687733 | −1.53554173 | 0.68132558 | 4.350511118 |
| 287 | −1.890800496 | −0.9175912 | −0.84177071 | 0.615422874 |
| 288 | −0.417807714 | −0.27643667 | 1.06515025 | 0.958812195 |
| 289 | 1.078763544 | 0.263281029 | 1.00763749 | 0.866949263 |
| 290 | 0.733561298 | −0.47493387 | 0.17088582 | 1.536463653 |
| 292 | 1.2252731 | 0.720498276 | 4.33362953 | 2.202084022 |
| 293 | 0.947860369 | 0.93449449 | 1.85056304 | 0.355024738 |
| 294 | −1.051634009 | 0.136579632 | 2.17918871 | −0.01949057 |
| 295 | 1.039790111 | 0.81471915 | −0.94326824 | 0.887662055 |
| 296 | 1.009509413 | 1.364418947 | 1.42805339 | 0.429992055 |
| 300 | 0.246930208 | 1.113809101 | 0.25540773 | 0.528760053 |
| 301 | 0.246930208 | 1.113809101 | 0.25540773 | 0.528760053 |
| 302 | 0.697198045 | −0.41500676 | −2.35076003 | −0.60639529 |
| 303 | 0.10667178 | 3.580489288 | 0.25893587 | 2.329367856 |
| 306 | 0.561360663 | −0.17793966 | −1.63250554 | −0.7564969 |
| 307 | 1.583243229 | 1.398558046 | 0.152423 | −0.13988304 |
| 308 | −0.067380931 | 0.74278658 | 0.29217479 | 0.180866298 |
| 310 | 0.238202662 | 0.926241567 | −0.66649303 | 0.508184193 |
| 312 | 0.714965519 | −0.45511207 | −2.34849436 | −0.9953911 |
| 314 | 0.736369931 | −0.52068396 | 0.53882253 | −0.7059813 |
| 316 | 2.314558863 | −0.25458611 | 0.22080129 | −0.04142716 |
| 317 | 1.095005005 | 0.057439852 | −1.20728654 | 0.035895107 |
| 318 | −0.111714595 | −0.61079351 | −1.16010053 | 1.102488007 |
| 319 | −0.264829849 | 0.540388888 | 0.10729709 | −0.57215449 |
| 321 | 1.243861203 | −0.75229123 | 0.05515858 | −0.34659253 |
| 322 | 0.956379568 | 2.838565742 | 2.7997689 | 0.805938034 |
| 323 | 1.884902746 | 0.813499245 | 0.86344403 | −0.1241887 |
| 324 | 0.189037208 | 1.105600415 | 0.48460989 | 0.285938173 |
| 325 | 0.791400443 | 2.454239197 | 1.54315324 | 1.416449646 |
| 328 | 1.22836182 | 2.190068443 | 2.48751772 | 0.126982574 |
| 329 | 1.800767509 | 1.372656013 | 2.09551175 | 2.849728342 |
| 330 | 2.688999059 | 0.017422444 | 0.34929031 | 0.108155361 |
| 331 | −0.223648429 | 0.873635097 | 1.78683863 | 0.126324441 |
| 332 | 1.884902746 | −0.46695445 | 0.1761545 | −0.11026722 |
| 333 | 0.956379568 | 2.838565742 | 2.7997689 | 0.805938034 |
| 334 | 0.569368001 | 2.811464091 | 1.88866785 | −0.16122533 |
| 335 | 1.931053264 | 2.306571877 | 4.45651797 | 4.474221307 |
| 336 | 1.355107839 | −0.49142588 | 0.83879083 | 0.18350392 |
| 338 | 1.025467157 | −0.99345477 | 0.57780149 | −0.19101275 |
| 339 | 1.216559787 | −0.68632827 | 0.71921804 | 0.140021721 |
| 342 | 2.073599715 | −0.19777074 | −0.44964804 | −0.71885866 |
| 343 | 3.375840967 | 3.294907583 | 5.0378352 | 4.14804591 |
| 344 | 0.926453735 | 1.336260845 | 2.20088072 | 0.226359561 |
| 346 | −0.133453942 | −0.27276578 | 0.95852923 | −0.88404805 |
| 347 | −0.414858428 | −0.94736055 | 1.9452074 | −1.32753709 |
| 349 | 0.011110326 | 0.415952358 | 1.08076289 | 2.638925816 |
| 350 | −1.366284701 | −1.3912958 | −0.0683659 | 1.205395618 |
| 352 | 2.592229701 | 2.014162407 | −0.56599991 | −0.19676404 |
| 353 | 2.347680291 | 1.432589328 | 3.81650185 | 2.28664738 |
| 354 | −0.094599823 | 0.704257624 | 0.8494127 | −0.05632553 |
| 355 | −0.534528735 | −0.26820008 | 0.69328667 | 0.63557685 |
| 356 | 0.71431796 | 0.568464069 | 1.14931631 | 0.32594963 |
| 358 | 1.637857828 | 1.932629993 | 0.68535871 | −1.06298922 |
| 359 | 3.169264285 | 2.326146291 | 5.44251947 | 3.621423972 |
| 360 | 2.824830639 | 3.29829616 | 3.43870859 | 3.771256974 |
| 361 | 0.772183137 | 0.62924397 | 1.14549597 | 0.743423792 |
| 362 | 2.158106604 | −0.08901432 | 0.85035629 | −0.37323677 |
| 363 | 1.485114303 | −0.85819594 | 0.70929196 | 4.132013298 |
| 364 | −0.661168364 | −0.30270875 | 2.49237859 | −0.7675819 |
| 365 | −0.518303431 | −2.08665423 | 0.5658944 | −1.10451499 |
| 366 | −0.501301831 | 0.561788544 | 0.14113617 | 0.610082057 |
| 368 | −0.106125097 | 1.092782715 | −0.89571841 | −0.08594454 |
| 369 | 1.43532227 | 1.656262941 | −1.09448841 | 1.674272267 |
| 370 | 1.064083705 | −1.08482967 | 0.35640283 | 0.866246621 |
| 371 | 1.933819902 | 0.975863726 | 1.62799441 | 1.492919426 |
| 372 | 1.933819902 | 0.975863726 | 1.62799441 | 1.492919426 |
| 373 | 0.274120553 | 2.246646022 | 2.93946992 | 2.617412085 |
| 374 | 0.940949346 | 2.935858163 | 0.52084392 | 0.847114052 |
| 375 | 0.177236108 | 2.745061961 | 0.76268843 | 0.373809692 |
| 376 | −0.999571921 | 0.579320229 | −0.06019938 | −0.94280945 |

-continued

| Material No. | MORV value for Equation a.) | MORV Value for Equation b.) | MORV Value for Equation c.) | MORV value for Equation d.) |
|---|---|---|---|---|
| 377 | 0.521811983 | −0.8476641 | 0.7732327 | 1.729406547 |
| 378 | −0.532701772 | −2.17823188 | 1.26760147 | 0.815211357 |
| 379 | −0.684994963 | 0.018353057 | −0.8170018 | 0.582030709 |
| 381 | 1.592237677 | 1.373054134 | 0.60184939 | −0.30300485 |
| 385 | 0.967501839 | 0.136172137 | 1.3645564 | 0.374341215 |
| 385 | 0.967501839 | 0.136172137 | 1.3645564 | 0.374341215 |
| 386 | 1.247138794 | −0.97883463 | 0.03688288 | −0.57321578 |
| 387 | 0.785485559 | −1.23629818 | −0.07759084 | −0.71795736 |
| 388 | 1.503632155 | −0.13455265 | 0.86630165 | 0.102845335 |
| 388 | 1.503632155 | −0.13455265 | 0.86630165 | 0.102845335 |
| 390 | 0.811363694 | 0.872605919 | −0.17445198 | 1.358866557 |
| 391 | 1.653006495 | −0.44095837 | 0.46475017 | −0.16817306 |
| 394 | 1.043989895 | −0.82625074 | 0.40893134 | −0.10417542 |
| 397 | 1.430046723 | −0.79407262 | 0.15684862 | −0.4384694 |
| 398 | −1.401723491 | 0.271079592 | 1.35530191 | −0.63550333 |
| 400 | 0.762211626 | −1.06778628 | −0.93642574 | −0.13193338 |
| 407 | 0.591198428 | −0.8943503 | 1.41392426 | 2.694863328 |
| 412 | −0.067309295 | −0.21963004 | 0.57788677 | −1.22740398 |
| 413 | 0.630456164 | 1.538096427 | 2.10994563 | 2.45668637 |
| 414 | 0.460631327 | 3.678501689 | 1.18326431 | 1.28320952 |
| 415 | 0.060485009 | −1.37776759 | −0.22689728 | 2.328813337 |
| 416 | 1.864088631 | 0.2451067 | 1.63260125 | 1.855346924 |
| 417 | −0.747017264 | −2.60335412 | 0.85092701 | 3.525229717 |
| 418 | 3.678359573 | 3.437930194 | 4.42449746 | 0.716864637 |
| 419 | −0.131519393 | 0.731836014 | 0.81604919 | −1.29993979 |
| 420 | 0.11276779 | −0.13029453 | 0.19422843 | 0.853490939 |
| 421 | 2.819997124 | 0.193567405 | 1.15903162 | 1.748390255 |
| 424 | −0.211768579 | 1.46336231 | −0.93580247 | −1.48749449 |
| 425 | −1.467980751 | −2.41196874 | −0.34454968 | 2.161517022 |
| 426 | 2.176374648 | 2.131594325 | 1.99252316 | 0.002774099 |
| 428 | 2.10568799 | 0.336366154 | −1.41176883 | 0.827982605 |
| 429 | 2.179080731 | 0.811454228 | −0.58304782 | 0.827982605 |
| 432 | 0.814675557 | −0.13076033 | 1.07380397 | −0.01560954 |
| 436 | 0.003614069 | −0.4704298 | 1.6004974 | −1.27605297 |
| 437 | −0.070955783 | −0.17246926 | 0.32599434 | 0.682083059 |
| 438 | 0.71141055 | −0.62729405 | 0.6220964 | 0.498836975 |
| 439 | −2.152188932 | −1.81662702 | 0.66042162 | −1.57001886 |
| 440 | 0.194444196 | 0.880854446 | 0.80016905 | 0.373809692 |
| 441 | 2.349282571 | 1.734747324 | 1.71148239 | 1.274963632 |
| 442 | 0.243841724 | 0.036287037 | 0.51243015 | 0.361825534 |
| 443 | −0.131519393 | 0.731836014 | 0.81604919 | −1.29993979 |
| 444 | 0.607958335 | 1.910541857 | −0.42710132 | −0.46909656 |
| 445 | −0.047486491 | 1.045012945 | −0.25220201 | −0.31982826 |
| 447 | 0.611981677 | 0.559261438 | −0.31210071 | −2.20421695 |
| 448 | 0.45491409 | 0.804084437 | 0.03088748 | −0.17549737 |
| 449 | 0.323968221 | −1.00428076 | −1.65151616 | 1.031096548 |
| 450 | 1.433196296 | −0.12277841 | 3.46809784 | −0.14760118 |
| 453 | 1.138642907 | 0.238344138 | −0.56453732 | −0.60639529 |
| 454 | 0.689556954 | −0.32116049 | 0.17614165 | 0.99165159 |
| 455 | −0.978653338 | −0.96381951 | 0.37950282 | 0.793341469 |
| 457 | 2.740852074 | 1.146976436 | 0.01429902 | 0.909817098 |
| 459 | 2.034203389 | −0.06483391 | 0.25864307 | 0.096715771 |
| 461 | 0.405441454 | 3.029508918 | 1.66201629 | 0.621375526 |
| 462 | 1.348588872 | 2.252065606 | 1.98535615 | 0.126982574 |
| 463 | 2.402548765 | 0.141297665 | 0.32401564 | 0.165555831 |
| 464 | 1.396358739 | −0.35292634 | 0.11760582 | −0.13960954 |
| 465 | 0.940569103 | 1.267891616 | 1.68420132 | 1.263608034 |
| 466 | −0.191220659 | 0.067062979 | 2.24237992 | 0.125280183 |
| 467 | 0.940569103 | 1.267891616 | 1.68420132 | 1.263608034 |
| 468 | 0.123370943 | 1.164309475 | 0.17099727 | −0.95446701 |
| 469 | 0.925252053 | −0.57178441 | 0.69807561 | −0.59133195 |
| 470 | 2.237616041 | 1.810156128 | −0.58140154 | 1.320304914 |
| 471 | 1.714516544 | −0.62135116 | 0.23636624 | −0.2706853 |
| 472 | 0.605628283 | 0.938001104 | 0.50028363 | 0.743911872 |
| 473 | 0.093847515 | −1.1973016 | −0.26960381 | 1.829684619 |
| 474 | 0.696773849 | 1.065592689 | 0.37607733 | −0.19214193 |
| 475 | 1.405352842 | 0.379589036 | 0.27781476 | 0.041425889 |
| 477 | 0.237582954 | 0.629327199 | 0.45159895 | −1.59912382 |
| 478 | 1.360648836 | 0.598053217 | 2.00883441 | −0.0827715 |
| 479 | 2.214928637 | −0.24358938 | −0.3486103 | 0.9190125 |
| 480 | 1.933819902 | −0.3826187 | 0.97439148 | 1.491603428 |
| 480 | 1.933819902 | −0.3826187 | 0.97439148 | 1.491603428 |
| 481 | 0.612364301 | −0.26364231 | −1.3201026 | −1.62884377 |
| 482 | 1.604448424 | 1.286308964 | −0.34289284 | 0.887781648 |
| 482 | 1.604448424 | 1.286308964 | −0.34289284 | 0.887781648 |

-continued

| Material No. | MORV value for Equation a.) | MORV Value for Equation b.) | MORV Value for Equation c.) | MORV value for Equation d.) |
|---|---|---|---|---|
| 484 | 3.269313083 | 2.336715633 | 3.65534824 | 2.158890088 |
| 486 | 1.530484593 | 1.052491466 | 3.11297562 | 0.430146348 |
| 487 | 2.889323404 | 2.226094104 | 4.12877599 | 2.184426542 |
| 488 | 1.062548487 | 4.75312035 | 2.78435853 | 2.01925207 |
| 491 | 0.397432667 | −0.20071274 | 0.842202 | 1.944142408 |
| 493 | 0.270731661 | −0.7406408 | −1.17192239 | 1.401933582 |
| 495 | 0.298981649 | 0.854414067 | −2.2714622 | −0.62848261 |
| 496 | 0.565278409 | 0.659352661 | −0.00159534 | 0.384991859 |
| 497 | 2.972647554 | 1.210988046 | 0.08629653 | 0.991649406 |
| 498 | 2.863652137 | 0.229707592 | −0.75515466 | −0.06022029 |
| 502 | 0.478208715 | 1.827989577 | 0.67676345 | −0.88328385 |
| 503 | 0.845706083 | 1.117392544 | −0.21773539 | 0.272770415 |
| 504 | 0.837488879 | 0.874463134 | −0.08311625 | 0.149327397 |
| 505 | 1.749446006 | 0.076054765 | −0.59137073 | 0.291488011 |
| 509 | 0.716903285 | −0.22917288 | −1.93027881 | −1.52173529 |
| 510 | 0.241638743 | 0.769444787 | −0.07283731 | −0.38771737 |
| 512 | 0.556069536 | −0.47514685 | −1.88388474 | −1.67297277 |
| 515 | 0.23291131 | 0.598998195 | −0.99553291 | −0.40829542 |
| 517 | 0.784181146 | −0.20530019 | −1.89414748 | 0.152726109 |
| 518 | 0.742030255 | 0.281479436 | −1.4156326 | −1.91369695 |
| 519 | 0.367442761 | −0.50911405 | −0.77651804 | 3.081125259 |
| 520 | 1.28335174 | −0.16976166 | 0.19676128 | 1.493753388 |
| 521 | −1.105672292 | −1.29204085 | −0.95149628 | 1.817322011 |
| 522 | 0.714965519 | −0.45511207 | −2.34849436 | −0.9953911 |
| 524 | 0.325255266 | 1.131242708 | −2.79377204 | −0.62848261 |
| 525 | −0.210625832 | 0.979060885 | 0.37926876 | −2.08002977 |
| 526 | 0.698504484 | 0.548193178 | 0.92265651 | 0.500152973 |
| 527 | 0.420012766 | 1.731459464 | −0.23341719 | 0.139565409 |
| 528 | 0.161304111 | 0.66712144 | 0.58401752 | 0.373809692 |
| 529 | 0.911890585 | 0.353572744 | 1.04706167 | 1.001090055 |
| 530 | 1.670680003 | 0.86138741 | −0.27652639 | 1.174059185 |
| 531 | −0.169223695 | 1.172917966 | −0.11306441 | 0.099121666 |
| 532 | 2.237616041 | 1.438074134 | 0.31117554 | −0.71786492 |
| 534 | 1.205873658 | 1.32208026 | 1.21816392 | −0.5027271 |
| 535 | 0.999469738 | 0.056406435 | 0.72382479 | −0.61170287 |
| 536 | 0.63876931 | −0.39111525 | 0.08747854 | −0.66833729 |
| 537 | 0.689953348 | 1.206425159 | 0.58870271 | 0.198159994 |
| 538 | 0.54988634 | −0.32842011 | 0.69258273 | −0.81953404 |
| 540 | 0.735538933 | −0.20826876 | 0.6955468 | −0.7170218 |
| 541 | 1.097368973 | 0.740159871 | 0.12012053 | 0.137772993 |
| 542 | −0.24632881 | −0.09354384 | −0.13580399 | 0.599029186 |
| 544 | 0.687639306 | −0.30861817 | 1.14537443 | −1.12865481 |
| 546 | 1.670680003 | 1.94609957 | 0.19633838 | 1.14825764 |
| 547 | −0.24632881 | −0.23975349 | −0.01449288 | 0.574861147 |
| 548 | 1.349418105 | −0.29885837 | 0.42849141 | 0.008671721 |
| 549 | 0.623933699 | −0.62776258 | −1.2835205 | −0.23131507 |
| 550 | 1.091300413 | −0.33969057 | 0.91994098 | 0.043900994 |
| 550 | 1.091300413 | −0.33969057 | 0.91994098 | 0.043900994 |
| 551 | 1.172668936 | −0.39476924 | −0.61394794 | −0.16425167 |
| 552 | 1.434150355 | 1.041294025 | 0.32000606 | 1.24279868 |
| 553 | 1.040907688 | −0.38050079 | −0.95306497 | −0.03036668 |
| 554 | 0.623933699 | −0.65991007 | −1.27562979 | −0.61529805 |
| 555 | 0.623933699 | −0.09654208 | −0.6432411 | 1.36608372 |
| 556 | 0.623933699 | −0.62776258 | −1.2835205 | −0.23131507 |
| 557 | −1.043779684 | 0.358151507 | 0.96578333 | −0.7498558 |
| 558 | 3.113548387 | 0.901949497 | −0.07402944 | 2.171129217 |
| 559 | 1.433732801 | 2.854621121 | 1.81079379 | 0.893806123 |
| 560 | 0.793851811 | 0.195900744 | 1.13222828 | −0.38432626 |
| 561 | 1.874725149 | 0.921395625 | 3.05642524 | 2.616508159 |
| 562 | −1.30410643 | −2.63450231 | 0.12574616 | 1.001870337 |
| 563 | −0.153585698 | 2.733591064 | 2.12854196 | 3.424603045 |
| 565 | 3.655479783 | 3.751479035 | 5.51820797 | 3.282822615 |
| 566 | 4.034374094 | 3.755759834 | 4.82506006 | 3.190861648 |
| 567 | 4.203811008 | 3.627632534 | 4.68751919 | 3.372829008 |
| 568 | 1.643514525 | 0.827299302 | 0.70706274 | 2.545428997 |
| 569 | 2.692371513 | 3.589810155 | 4.40390088 | 4.506937878 |
| 570 | 1.707556133 | 2.400065573 | 1.78745169 | 2.655458557 |
| 571 | 1.862893827 | 2.803280605 | 0.98209954 | 3.188564781 |
| 572 | 1.203581368 | 0.798608763 | 2.67898788 | 1.659633314 |
| 573 | 2.459623568 | 2.656773866 | 3.54771795 | 2.085649266 |
| 574 | 2.878405284 | 1.770500246 | 4.00464111 | 4.859737959 |
| 575 | −0.395731956 | 0.325594009 | 0.98982713 | −0.25791379 |
| 576 | −0.2346025 | 0.890438549 | −0.13206526 | −0.83961838 |
| 577 | 0.484934913 | 2.001798597 | −0.11430063 | −0.05230593 |
| 578 | 1.138642907 | −0.72228381 | −1.0321 | −0.60639529 |

-continued

| Material No. | MORV value for Equation a.) | MORV Value for Equation b.) | MORV Value for Equation c.) | MORV value for Equation d.) |
|---|---|---|---|---|
| 579 | −2.722013313 | −3.79238321 | −1.13572295 | 0.953543134 |
| 580 | 1.138642907 | −0.66601616 | −0.95089973 | 1.036450105 |
| 581 | 1.105119249 | −0.82090309 | −0.06184517 | −0.90904158 |
| 582 | 2.092976965 | −0.31228784 | 0.08755137 | −0.62955362 |
| 583 | −0.24632881 | −1.33540368 | −0.96483147 | 0.624830731 |
| 584 | 2.237616041 | 0.30800753 | −0.44296441 | −0.71918014 |
| 585 | 0.634021669 | −0.28724544 | −0.74527157 | −1.361765 |
| 586 | 1.313957377 | 0.449601 | 1.50810166 | −0.30998322 |
| 587 | 0.304876136 | −0.43283205 | 1.23096012 | 0.398961811 |
| 588 | 0.449793066 | 0.007950225 | 0.8004147 | −0.63434071 |
| 589 | −0.681766404 | 1.08547116 | 0.54331319 | −2.16710754 |
| 591 | −0.34676031 | −0.77573166 | 1.85884084 | 0.312272735 |
| 592 | −1.573190219 | 2.29028194 | 1.86285367 | 0.687279186 |
| 594 | −1.45374647 | 0.452156392 | 2.48970747 | 0.858468114 |
| 595 | 0.058003677 | −1.91126878 | 1.52586392 | −0.07528071 |
| 599 | 1.485777974 | 1.54384772 | 0.79002365 | −0.09069773 |
| 600 | 1.914093549 | 0.841364523 | 0.15173954 | 0.255445859 |
| 601 | 1.203870517 | 1.17864533 | 1.22686262 | 0.453935114 |
| 602 | 0.771984982 | 0.66859171 | −0.37427136 | 0.07599515 |
| 603 | 3.218950175 | 1.464118271 | 2.47512497 | 1.214429025 |
| 604 | 2.710087358 | 1.517756148 | 0.35088855 | 0.603171932 |
| 605 | 0.703615734 | 0.42129186 | 0.39567696 | 0.41729786 |
| 606 | 0.055463315 | 1.972687323 | 3.42898264 | 1.395457482 |
| 607 | −0.146397553 | −2.05649732 | 0.17598641 | 1.900931587 |
| 608 | 1.473771668 | 2.08260463 | −1.09319437 | 0.44289209 |
| 609 | −0.466215117 | 0.845009196 | 1.89800228 | 0.840292062 |
| 610 | 2.14236439 | 1.079695535 | 0.29060257 | 1.329215628 |
| 611 | 1.078583502 | 1.707732184 | −0.73721672 | −0.87923138 |
| 612 | −0.128136098 | 1.038320983 | −0.63703066 | 0.184527669 |
| 613 | 1.599427115 | 3.615521066 | 0.43343413 | −0.1515479 |
| 614 | 1.489603514 | 2.706865637 | −0.06242639 | −0.47244791 |
| 615 | 1.960664614 | 4.490550162 | 2.26962278 | 0.346542121 |
| 616 | 2.689328335 | 3.692579375 | 2.01499213 | 1.348800283 |
| 617 | −0.845027889 | 0.504788036 | 0.4957383 | −0.65628324 |
| 618 | −0.461016335 | 1.612995126 | 1.09551709 | −1.62235977 |
| 619 | −0.222804396 | 0.361727974 | 0.62743416 | −1.02982449 |
| 620 | 0.745610019 | −0.76737462 | −0.67364137 | 1.696394301 |
| 621 | 3.671429366 | 1.708460032 | 4.57083156 | 1.955988764 |
| 624 | 2.139270802 | 2.093130621 | 2.5533383 | 3.30383102 |
| 625 | 0.665423108 | 1.356936283 | 1.5515704 | 1.874119646 |
| 626 | 1.292942787 | 0.621140137 | 2.28513785 | 1.042322574 |
| 627 | 1.14724223 | −0.51104438 | 1.01088446 | 1.51232276 |
| 628 | 1.44418619 | 3.825155203 | −0.84341678 | −0.02251455 |
| 631 | 2.622138509 | 5.106659136 | 4.48303003 | 2.115425367 |
| 632 | 2.450328692 | 4.670297017 | 4.54579766 | 2.15781135 |
| 633 | 1.560465308 | 2.636096631 | 2.45546606 | 0.920962489 |
| 635 | 1.510161132 | 2.388971583 | −0.63579931 | 1.939575919 |
| 636 | 1.433842763 | 0.529693203 | −0.23195491 | 1.22356734 |
| 638 | 1.921725015 | 0.758255259 | 0.81570609 | 3.615611357 |
| 639 | 0.422001837 | −0.14885323 | −0.00660617 | 1.726576493 |
| 640 | 0.865825265 | −0.28827025 | −0.54129473 | 0.283616979 |
| 641 | 0.813978315 | 0.509726232 | 0.37457254 | 0.842075065 |
| 644 | 0.85173251 | 0.664325682 | 1.88299246 | 0.951603698 |
| 645 | 0.417907652 | −1.00347186 | 0.9667556 | −0.47157656 |
| 647 | 0.221569324 | −1.2239438 | 0.91464498 | −0.19166679 |
| 649 | −0.560315649 | −0.67419393 | −0.02482011 | 1.492767049 |
| 650 | 1.640396187 | 0.328871961 | 0.04729888 | 0.912259803 |
| 651 | 0.672555558 | −0.9987845 | 0.48545476 | −0.13530683 |
| 652 | −0.995969271 | −1.38653208 | −0.49268035 | 0.944524468 |
| 653 | 1.203949791 | 0.0153333 | −0.10401424 | 0.73323846 |
| 655 | 1.334772083 | 0.418728831 | −0.92221842 | 1.317365259 |
| 658 | 0.414934548 | 0.314990682 | 2.78051829 | 2.656854539 |
| 659 | 3.996948911 | 1.915319951 | 3.03990612 | 5.764113617 |
| 660 | 2.175041013 | 1.882945358 | 0.07779745 | −0.18323732 |
| 661 | −0.316755016 | 1.64607349 | 2.76327471 | 2.024910676 |
| 662 | 0.258228842 | 0.844792644 | 0.1924797 | 0.098776211 |
| 663 | 1.521826905 | 1.097809988 | 2.13583044 | 1.30609234 |
| 664 | 0.708920214 | −0.27795513 | 0.15395433 | 0.014791904 |
| 665 | 0.630772742 | −0.34278374 | 0.49097281 | −0.0565644 |
| 667 | 0.812238101 | 0.195908668 | 0.21564664 | 0.219336109 |
| 668 | 1.529097453 | 2.246515706 | 1.4678099 | −0.81836944 |
| 671 | 1.453855457 | −0.51177209 | −0.78608937 | 0.361715513 |
| 672 | 0.771613806 | −0.81209599 | −0.85297613 | 0.084880782 |
| 673 | 1.874725149 | 0.921395625 | 3.05642524 | 2.616508159 |
| 674 | 5.912391366 | 3.468705262 | 6.81994671 | 7.217631788 |

-continued

| Material No. | MORV value for Equation a.) | MORV Value for Equation b.) | MORV Value for Equation c.) | MORV value for Equation d.) |
|---|---|---|---|---|
| 675 | 0.525794155 | 0.473286101 | 2.51749677 | 2.935001452 |
| 676 | 0.623704257 | 1.523736626 | 2.50208859 | 2.474137331 |
| 677 | −0.548848405 | 0.058004962 | 1.07849806 | 2.361730638 |
| 678 | 4.818555677 | 1.506257638 | 4.96635528 | 5.508133385 |
| 679 | 4.332202737 | 2.699343437 | 5.65576391 | 5.021298111 |
| 680 | 4.042984412 | 4.75506829 | 4.65903898 | 4.913020939 |
| 681 | 0.5959536 | 2.091803965 | −0.14697928 | −0.71889234 |
| 683 | 0.87899671 | 0.043210589 | 1.37554648 | −0.60198897 |
| 684 | 2.349844428 | 1.181400632 | 2.15359469 | 2.136987013 |
| 686 | 1.024635336 | 1.040500794 | 0.9820242 | −1.16405004 |
| 687 | 0.551495677 | 0.66297128 | −0.45433071 | −1.28827912 |
| 691 | 1.609835015 | 2.898881191 | −0.99203246 | −0.15162554 |
| 692 | 2.002379485 | 3.95875961 | 1.1705779 | 0.346542121 |
| 693 | 4.264631423 | 4.375626605 | 0.93418004 | 0.114988571 |
| 693 | 4.264631423 | 4.375626605 | 0.93418004 | 0.114988571 |
| 694 | 4.858313721 | 4.772826468 | 3.58732214 | 2.558402204 |
| 696 | 2.99409154 | 3.843066736 | 2.50597637 | 1.205022789 |
| 697 | 0.407534444 | 2.829113684 | 2.16548165 | 0.756766079 |
| 698 | 0.983060431 | 2.328872529 | 1.67788951 | 0.805938034 |
| 699 | 0.996500165 | 0.60129571 | −0.27496491 | −0.22179967 |
| 700 | 0.698400489 | 0.514637899 | 1.14265307 | 0.816064314 |
| 701 | 0.592372435 | −0.67812322 | −1.75051912 | −0.51109618 |
| 702 | −0.211768579 | 1.46336231 | −0.93580247 | −1.48749449 |
| 703 | 0.372029303 | 0.866016277 | −0.91679974 | 0.347054507 |
| 704 | 1.187861135 | 0.858978871 | 0.1265005 | 0.217668671 |
| 706 | 0.193569186 | 1.623921627 | 0.08867618 | 0.808617424 |
| 707 | 0.819562098 | 3.57840156 | 3.38080377 | 1.26599216 |
| 708 | 2.391828225 | 1.877690145 | 3.85935427 | 1.647356195 |
| 709 | 1.280902077 | 2.17019575 | 3.40315777 | 0.126982574 |
| 710 | 1.454593977 | 3.128186882 | −2.26368122 | −0.02251455 |
| 711 | −0.783387499 | 1.465620573 | 1.22912535 | −1.41213701 |
| 712 | 1.936489942 | 2.528373237 | 2.13424487 | 2.393940425 |
| 713 | 1.303999908 | 2.146563611 | −0.26420591 | −0.01477791 |
| 714 | 2.3584433 | 3.778880151 | 3.4396901 | 1.593719007 |
| 715 | 4.023918591 | 3.403899942 | 5.07447567 | 4.880181625 |
| 716 | 0.981194248 | 1.73892162 | 2.21166953 | 2.738129365 |
| 717 | 0.983060431 | 2.328872529 | 1.67788951 | 0.805938034 |
| 718 | 1.241840746 | 3.430871861 | 0.55000978 | 1.073616332 |
| 719 | 1.483275952 | 3.037398628 | −1.55547275 | −0.47244791 |
| 720 | 2.372311412 | 3.403234423 | −0.21191089 | −0.08519829 |
| 721 | 2.128185431 | 0.274654772 | 0.47626043 | 2.465333527 |
| 722 | 0.616377169 | −0.58753328 | 0.48821573 | 1.063402884 |
| 723 | −1.273274319 | −1.12897478 | 1.71118519 | 4.067480158 |
| 724 | 2.103515193 | 0.165377929 | −0.18223896 | 0.288303217 |
| 725 | 0.983060431 | 2.328872529 | 1.67788951 | 0.805938034 |
| 726 | 2.887615733 | 3.282342953 | 1.95034945 | 2.462290186 |
| 727 | 2.241052707 | 2.13951389 | 0.36814978 | 0.371689426 |
| 730 | 1.121105724 | −0.20397307 | −0.15741334 | 0.897609916 |
| 731 | 1.437838545 | −0.09620743 | 0.02756967 | 1.949139525 |
| 733 | −0.46922259 | 1.067777032 | 1.61226345 | 0.185415155 |
| 735 | −0.081273581 | 1.192925027 | 1.67970188 | 0.33874614 |
| 736 | −0.13000788 | 1.099012031 | 1.64139691 | 0.248287146 |
| 738 | 1.670680003 | −0.20756775 | −0.73755051 | −0.84924056 |
| 740 | −1.532691904 | −2.55214711 | 0.57438104 | 0.555698696 |
| 741 | 1.407504561 | 0.048284736 | 1.01405149 | −2.2579901 |
| 742 | 0.644803847 | 0.644647752 | 1.35192052 | −0.62780087 |
| 743 | 0.174679072 | 0.169515693 | 0.62350977 | −0.08144308 |
| 744 | 0.02068385 | 0.648730454 | −0.04946215 | 0.214634634 |
| 745 | 0.741424752 | 0.523647641 | 0.52863925 | −0.65426285 |
| 746 | 1.285306965 | 1.929408375 | 0.85560877 | −1.4619958 |
| 748 | −1.513804897 | −1.10823383 | 1.09397284 | −0.88975989 |
| 750 | 2.554017714 | 3.544542579 | 4.42317523 | 1.647356195 |
| 752 | 2.592229701 | 1.158945916 | 0.24149847 | −0.58379051 |
| 754 | 1.649506181 | 1.31981993 | 2.36997533 | 0.406081966 |
| 755 | −0.028552173 | 0.253838465 | 0.95694896 | −0.16565786 |
| 757 | 1.446915042 | 0.673406021 | −0.6641103 | −1.80002119 |
| 758 | 5.933043009 | 5.716461604 | 6.67410554 | 4.433272782 |
| 760 | −3.195604514 | −2.60998376 | −0.11222221 | 0.792186468 |
| 761 | 0.286783044 | −0.52414055 | −0.57593161 | 0.628896611 |
| 763 | 1.405567948 | −0.84372738 | −1.32379279 | −0.50314577 |
| 766 | 0.279442569 | −1.00722191 | −0.18524031 | 2.487147765 |
| 767 | −1.32777782 | −2.36136561 | −0.79602501 | 1.247063893 |
| 768 | −0.692560954 | −1.92177717 | 0.46687554 | 2.400762497 |
| 769 | 1.889999468 | 1.112266205 | 0.82815523 | 0.525271623 |
| 770 | 2.237616041 | 2.282141767 | −0.149966 | −0.71866539 |

-continued

| Material No. | MORV value for Equation a.) | MORV Value for Equation b.) | MORV Value for Equation c.) | MORV value for Equation d.) |
|---|---|---|---|---|
| 771 | 0.909356011 | 0.368597887 | 1.03689838 | 1.001198751 |
| 772 | 1.328601831 | 0.715296776 | 0.20358825 | 1.147403521 |
| 774 | 2.002379485 | 3.95875961 | 1.1705779 | 0.346542121 |
| 775 | 1.936489942 | 2.528373237 | 2.13424487 | 2.393940425 |
| 776 | 1.495019673 | 4.35984375 | 2.59969954 | 2.95313487 |
| 777 | 0.206892499 | −0.57813502 | −0.32983 | 0.781221286 |
| 778 | 1.340232187 | −0.11034804 | 0.35759778 | 1.690582999 |
| 779 | 0.595257521 | −0.85639987 | 0.19436224 | −0.73333902 |
| 781 | 2.187955186 | 2.571774369 | 2.74817529 | −0.52827851 |
| 782 | 0.893855657 | 0.63313304 | 1.19104388 | −1.61620514 |
| 784 | −0.275919571 | −1.64491584 | 0.60429762 | −1.5580623 |
| 786 | −0.043537347 | 1.337721065 | −0.56551398 | −0.02167052 |
| 788 | 2.147983695 | 1.250042565 | 1.72576392 | 1.626956379 |
| 789 | −0.624451013 | 0.76248127 | −0.79219481 | −0.73513092 |
| 791 | 0.227060873 | −0.04783658 | −0.16862915 | 1.166609659 |
| 792 | 0.90746622 | 1.643598677 | 0.26467094 | 0.396081003 |
| 796 | 0.811374104 | 0.766579899 | 0.10161642 | 0.135186519 |
| 797 | −0.185638022 | 0.53853264 | 0.65441562 | −0.25681926 |
| 799 | 0.657769581 | 0.095543194 | 0.89522656 | 0.558428618 |
| 800 | 0.227060873 | −0.04783658 | −0.16862915 | 1.166609659 |
| 802 | −0.660595577 | 1.597474466 | 1.49106895 | −0.20429128 |
| 803 | 1.706162052 | 0.623892414 | 0.59662073 | 0.7745661 |
| 804 | 3.478490379 | 2.348697011 | 3.96279011 | 2.456963386 |
| 805 | 0.377241729 | 0.83329773 | 0.1712741 | 1.057125999 |
| 806 | 2.863652137 | 0.771287371 | −0.4183972 | −0.44551461 |
| 807 | 1.794279084 | 0.711717977 | 0.35187068 | −1.0208486 |
| 808 | 0.408210632 | 0.633556897 | −0.37022584 | 0.717270748 |
| 810 | −2.506277966 | −2.61703099 | 0.87880054 | −0.72832121 |
| 811 | −0.789075789 | −0.15346024 | 0.64720487 | −0.48507671 |
| 812 | −1.395132583 | −2.59063834 | 0.14973761 | 0.623759794 |
| 814 | 0.414608216 | −0.23108581 | 1.15081653 | −1.10351559 |
| 817 | −0.24632881 | −0.09354384 | −0.13580399 | 0.599029186 |
| 819 | 0.805916178 | 0.96701754 | −0.8811308 | −1.23858491 |
| 820 | 0.744770665 | −0.73855596 | −0.2249849 | −0.2981968 |
| 821 | 1.099377934 | −0.55297074 | −0.58846144 | −1.64325365 |
| 824 | −0.183625049 | 1.183962609 | 1.63494269 | 0.25504959 |
| 826 | 1.678825829 | 1.234136613 | 1.45948258 | 0.224375571 |
| 827 | 2.592229701 | 0.621958527 | −0.52522117 | −0.19676404 |
| 828 | 2.592229701 | 0.57915141 | −0.51767373 | −0.58077497 |
| 829 | 1.670680003 | 1.284791367 | 0.14864516 | −0.84985664 |
| 831 | 1.116827432 | −0.75462162 | 0.39137278 | −0.04171761 |
| 832 | 0.516805788 | −0.98195801 | −1.03806082 | −0.25383454 |
| 833 | 1.490368312 | 0.080687244 | −0.97130296 | 0.833722265 |
| 834 | −0.369014518 | −1.35841128 | −1.27372214 | 1.351157886 |
| 835 | 0.914072736 | −0.8695664 | 0.36889122 | −0.08606658 |
| 836 | 0.998848923 | −0.42464651 | −0.23731009 | 0.395895785 |
| 837 | 1.670680003 | 0.070165381 | −0.64700996 | −0.85055617 |
| 838 | 0.810918992 | −0.75696962 | −0.21854084 | 0.836677293 |
| 839 | 1.066219316 | −0.66764691 | −0.49983634 | 0.669914 |
| 840 | 1.078821776 | −0.72511699 | −1.00012288 | −0.15789319 |
| 845 | −0.163950017 | −0.21616766 | 0.65276069 | −0.52575739 |
| 846 | 0.665621985 | −3.16625248 | 0.34329102 | −1.44312939 |
| 847 | −0.233400992 | −1.15488444 | 0.83051343 | −1.85751897 |
| 848 | −0.631135606 | 0.037691556 | 0.57903451 | −0.9926 |
| 849 | 1.707541313 | 0.010345383 | 0.48581606 | 1.513341091 |
| 850 | 1.447075297 | 0.022864201 | 0.99130501 | 0.473154634 |
| 851 | −0.24632881 | −0.23975349 | −0.01449288 | 0.574861147 |
| 852 | 1.176028423 | −0.85747031 | −0.72464089 | 0.30542841 |
| 856 | 2.237616041 | 0.345329597 | −0.60597063 | −0.71581056 |
| 858 | −1.47960224 | −2.5770536 | −1.03619781 | 0.847300104 |
| 864 | 1.670680003 | 1.284791101 | 0.14864516 | −0.84985664 |
| 865 | 1.670680003 | 1.916382859 | 0.6998144 | 1.124089601 |
| 866 | 1.024819853 | −0.7521596 | 0.35073152 | −2.14193241 |
| 868 | 2.237616041 | −0.17986241 | −0.86317199 | 1.325805381 |
| 869 | 1.747776963 | −0.25802105 | −1.11614995 | −0.77093434 |
| 870 | 2.592229701 | 2.030913569 | −0.50618719 | 1.463926567 |
| 871 | 2.592229701 | 2.510587108 | −0.07540594 | −0.58371481 |
| 872 | 1.800767509 | 1.372656013 | 2.09551175 | 2.849728342 |
| 873 | 1.849432484 | 4.556065495 | −0.39732139 | −0.67726477 |
| 875 | 0.201768224 | 0.618509503 | −0.39732139 | −0.67726477 |
| 876 | 2.237616041 | 1.553468488 | −0.72864242 | −0.33330779 |
| 877 | 0.323968221 | −1.00428076 | −1.65151616 | 1.031096548 |
| 878 | 0.783570663 | 2.023288951 | −0.03975252 | 0.474038265 |
| 879 | 1.187592149 | 1.464239711 | 0.67009263 | 1.103774764 |
| 880 | −0.192632911 | 0.142411101 | 0.79310676 | 0.125548041 |

-continued

| Material No. | MORV value for Equation a.) | MORV Value for Equation b.) | MORV Value for Equation c.) | MORV value for Equation d.) |
|---|---|---|---|---|
| 881 | 1.071875228 | 0.911734331 | −1.50008456 | 0.185176261 |
| 882 | 0.798806784 | −0.1516478 | −0.64900063 | −0.77199025 |
| 883 | −0.671908804 | −0.65984824 | 0.5238174 | −0.85314111 |
| 884 | 2.863652137 | 1.896850773 | 0.06443558 | −0.44689505 |
| 885 | 2.314558863 | −0.25458637 | 0.22080129 | −0.04142716 |
| 886 | 2.314558863 | −0.25458637 | 0.22080129 | −0.04142716 |
| 888 | 0.131224024 | 0.21510779 | −1.70996346 | 0.964902175 |
| 889 | 0.742030255 | 0.281479436 | −1.4156326 | −1.91369695 |
| 890 | 1.071875228 | 0.911734331 | −1.50008456 | 0.185176261 |
| 891 | 0.742030255 | 0.281479436 | −1.4156326 | −1.91369695 |
| 892 | 1.749446006 | 0.076054765 | −0.59137073 | 0.291488011 |
| 893 | 0.869958847 | 0.843158237 | 0.61532515 | 3.158279932 |
| 894 | 1.749446006 | 0.076054765 | −0.59137073 | 0.291488011 |
| 897 | −0.047486491 | 1.045012945 | −0.25220201 | −0.31982826 |
| 899 | 0.784181146 | −0.20530019 | −1.89414748 | 0.152726109 |
| 900 | 0.784181146 | −0.20530019 | −1.89414748 | 0.152726109 |
| 901 | −0.440378333 | 0.918089245 | 0.03050609 | −1.62235977 |
| 902 | −0.2346025 | 0.890438419 | −0.13206526 | −0.83961838 |
| 903 | −0.440378333 | 0.918089245 | 0.03050609 | −1.62235977 |
| 904 | −1.320466583 | −2.49763118 | 0.9787365 | −1.85867969 |
| 905 | −0.386224123 | −0.24799559 | 1.19406353 | −1.61243489 |
| 908 | 1.878331515 | 1.287303121 | 0.11530502 | 1.132065786 |
| 909 | 0.614968453 | −1.61827184 | −0.80789799 | −0.66927285 |
| 912 | 0.530707518 | 0.774109528 | 3.0396125 | 4.394775258 |
| 913 | 0.337020095 | 1.531840025 | 0.10544973 | 0.347450471 |
| 914 | 0.774589061 | 1.224705331 | 1.87994281 | −0.11684579 |
| 916 | −0.363201351 | 0.35600238 | −1.20673542 | 2.056973054 |
| 918 | 0.153047955 | 0.702054562 | 0.76757802 | 0.096096862 |
| 919 | 2.891894151 | 2.295157633 | 3.54101626 | 1.984030826 |
| 920 | 1.292959895 | 0.808281618 | 2.92956952 | 2.204248324 |
| 921 | −0.465333775 | 0.862817284 | 0.85365652 | 0.64701735 |
| 922 | 1.54265003 | 0.291977233 | 0.79089158 | 0.801314068 |
| 923 | 1.340862559 | 0.503169303 | 0.53213093 | 3.164832031 |
| 924 | 0.158497146 | 1.507280765 | 2.25315926 | 1.173977914 |
| 925 | 1.23162703 | 1.671882685 | 3.1838372 | −0.22917041 |
| 926 | 2.608734063 | 3.080604939 | −0.69726361 | −0.36219702 |
| 927 | 1.879182741 | 3.409153142 | 2.48473663 | 3.409954437 |
| 928 | −0.093106169 | 0.019939108 | 0.15932154 | 1.229749745 |
| 929 | 1.670680003 | 1.94609957 | 0.19633838 | 1.14825764 |
| 930 | 3.052627325 | 0.956834107 | −0.29721209 | −0.31007607 |
| 931 | 0.367631287 | 0.501274945 | −1.31074554 | −0.39331005 |
| 933 | 3.702965303 | 3.03402795 | 4.33630831 | 4.238503729 |
| 937 | 0.570011387 | 0.097928934 | 1.03350455 | −0.13392581 |
| 939 | 1.801474588 | 0.770314085 | 0.70188154 | 0.22333959 |
| 940 | −0.412950838 | −0.1781887 | 0.50649275 | −0.57215449 |
| 941 | 1.691004766 | −0.42331992 | 0.66279648 | 0.0318465 |
| 942 | 1.451782586 | −0.565439 | −0.32447381 | −0.43378383 |
| 943 | 1.188491672 | 0.120632811 | 0.20106994 | 3.078484746 |
| 945 | 1.214814941 | 0.806987609 | 0.47605587 | 1.372949466 |
| 946 | 0.561732094 | 1.21448402 | 0.35542793 | −1.03704442 |
| 947 | 0.956565856 | 1.505997176 | 0.88115653 | −0.60583691 |
| 948 | 0.592575441 | 1.383482681 | 0.93567635 | 1.058669028 |
| 950 | 0.343657562 | −0.85471906 | −0.21125904 | 1.184648122 |
| 951 | 1.236659334 | 3.828926809 | 1.57729777 | −0.31942874 |
| 953 | 1.836389049 | 0.755753735 | −0.36014522 | 1.262853393 |
| 953 | 1.836389049 | 0.755753735 | −0.36014522 | 1.262853393 |
| 954 | 1.001653875 | −0.85635082 | 0.89224781 | −0.39245818 |
| 955 | −0.122918652 | −0.846489 | −0.63367729 | 1.182912962 |
| 956 | 0.589766639 | −0.9783487 | −0.67638264 | −0.38772225 |
| 958 | 0.715082397 | −0.90020686 | 0.86817768 | 0.030652004 |
| 959 | 1.609198886 | 0.500797943 | 0.795571 | 0.908389449 |
| 960 | 0.952787327 | −0.90555475 | −0.17381408 | 0.06786323 |
| 962 | 1.836429446 | 0.208275147 | −0.14300625 | 1.067462181 |
| 965 | 1.9158432 | 0.35211823 | −1.02174589 | 0.625657932 |
| 967 | 1.383869627 | 0.274520494 | −0.11659267 | 0.840327437 |
| 969 | −0.445579934 | −1.68867059 | −0.5241276 | 2.233793943 |
| 971 | 0.736419048 | 0.409875189 | −0.63140848 | 0.034514594 |
| 973 | 1.073465817 | 2.18418874 | 2.01361447 | −0.93754437 |
| 974 | 0.130904221 | 1.882440008 | 1.85101055 | 0.112524893 |
| 976 | −0.236681385 | −0.09745533 | 0.1779313 | 2.08923366 |
| 977 | 0.904402612 | 0.936956925 | 0.87731788 | 0.102346515 |
| 978 | 2.201759817 | 2.123549573 | 3.7881607 | 2.358768953 |
| 980 | 1.784266982 | 1.845281076 | 3.42873622 | −0.31098233 |
| 981 | −0.225023329 | 0.087962898 | −0.29053012 | 0.514272787 |
| 982 | −0.231175318 | −0.0159671 | 1.27391892 | 1.090487158 |

-continued

| Material No. | MORV value for Equation a.) | MORV Value for Equation b.) | MORV Value for Equation c.) | MORV value for Equation d.) |
|---|---|---|---|---|
| 983 | 0.889215441 | 0.24321159 | 0.06877629 | 0.816247177 |
| 985 | 1.864634345 | 0.133647536 | 1.29803755 | 1.951226654 |
| 986 | 0.511450274 | −2.33512445 | −0.56246315 | −0.42184152 |
| 987 | 0.847260813 | 0.368638185 | 0.4114346 | 0.219336109 |
| 988 | 1.596170102 | 1.592158381 | 0.30052357 | 0.283467897 |
| 993 | −3.549941097 | −2.6847861 | −0.17502622 | 1.41034664 |
| 994 | 0.445802042 | 0.899738574 | 0.61059602 | 0.323194673 |
| 995 | 0.949498724 | 0.357111159 | 0.28371155 | −0.14156488 |
| 998 | 2.197271885 | 1.578871826 | 0.90563334 | 1.056619658 |
| 998 | 2.197271885 | 1.578871826 | 0.90563334 | 1.056619658 |
| 1000 | 1.456120673 | 0.626173572 | 0.07683183 | −0.43324035 |
| 1001 | −0.440378333 | 0.918089245 | 0.03050609 | −1.62235977 |
| 1002 | 0.819929066 | 0.459101825 | −0.09227583 | 0.324342063 |
| 1003 | 1.64412453 | −0.09343399 | 0.70197344 | 3.710273595 |
| 1004 | 0.796928207 | 0.459954079 | −0.88538616 | 0.152000937 |
| 1005 | 0.044923203 | −0.19994963 | 0.60082875 | 0.258347835 |
| 1006 | −0.320452673 | −0.33232662 | −0.52315783 | 1.406273663 |
| 1007 | 4.040291133 | 3.474551355 | 3.57146797 | 3.565985043 |
| 1008 | 0.764519082 | 0.917635102 | 2.88258762 | 2.319622474 |
| 1009 | −0.071112206 | 0.539362906 | 2.98048732 | 0.580423329 |
| 1010 | −0.689737481 | 0.547928768 | 1.98805626 | −0.76653376 |
| 1011 | 0.343668917 | 0.931501008 | −0.05483722 | 0.395369857 |
| 1012 | 1.926713131 | 0.124849138 | −0.09654906 | 1.126499382 |
| 1016 | 0.124247716 | 0.193102712 | 0.39003599 | 1.737670628 |
| 1017 | 0.131224136 | 0.21510779 | −1.70996346 | 0.964902175 |
| 1018 | 0.499624069 | 0.962843507 | 0.77617619 | −1.15296947 |
| 1019 | 0.813491983 | 0.322635656 | 0.02800396 | 0.599500927 |
| 1020 | 0.715468114 | 1.015469049 | 1.45994989 | 0.352548581 |
| 1021 | −1.176339404 | 1.539767848 | −0.14427147 | 1.389902738 |
| 1022 | 1.364966718 | 1.690570939 | 2.05914194 | 2.364375484 |
| 1023 | 2.154641091 | 0.800066339 | 0.85365652 | 0.965810338 |
| 1024 | 2.302280068 | 1.252164308 | 1.73414439 | 1.549538352 |
| 1025 | 1.878331515 | 1.287303121 | 0.11530502 | 1.132065786 |
| 1026 | 2.97722987 | 2.096441965 | 3.87172868 | 0.550274831 |
| 1027 | 2.474381478 | 1.950326182 | 3.81861867 | 1.366897355 |
| 1028 | 1.778414353 | 3.114931059 | 4.47690731 | 6.054314034 |
| 1029 | 3.672910795 | 2.760483725 | 3.26915034 | 3.042677588 |
| 1030 | −0.604959715 | −2.13584086 | 0.8687855 | 0.024144016 |
| 1031 | 2.012732245 | 2.293857161 | 0.54405555 | 1.261882121 |
| 1032 | −1.086688867 | 0.953083194 | 2.92177054 | 0.876865185 |
| 1033 | 1.617520676 | 1.008017006 | 2.21183536 | −0.1288484 |
| 1035 | 2.506372295 | 3.419954592 | 4.58206882 | 4.134341651 |
| 1036 | −0.675805062 | −0.15357004 | 0.94597719 | 3.966016669 |
| 1037 | −0.275092569 | −0.67687665 | −0.52763797 | 1.489972106 |
| 1038 | 2.753559643 | 3.81185814 | 2.71344734 | 2.243351472 |
| 1039 | 0.65087433 | 0.026885305 | −0.0153558 | 0.011870127 |
| 1040 | 0.141526548 | −1.65455278 | 0.50170705 | −1.90794 |
| 1041 | 0.458680435 | −0.69730218 | −0.48806249 | 0.586073092 |
| 1042 | −0.513264812 | −0.22001961 | 0.36339519 | 1.03208599 |
| 1043 | −1.497887014 | −1.76116109 | −0.76634926 | 1.137002742 |
| 1045 | 2.863652137 | 1.96790869 | 0.43661485 | −0.44756897 |
| 1046 | 0.981194248 | 1.73892162 | 2.21166953 | 2.738129365 |
| 1047 | 0.981194248 | 1.73892162 | 2.21166953 | 2.738129365 |
| 1051 | 0.70261974 | −0.22197386 | 0.19710806 | −2.37196477 |
| 1052 | 0.662126832 | 0.741436531 | 0.61672724 | 0.289359903 |
| 1053 | 0.87463644 | −0.19717783 | 1.2664131 | −0.4187507 |
| 1054 | 0.284558077 | −1.46754925 | −0.03124571 | 0.587227244 |
| 1055 | 0.885837831 | −0.91907796 | −0.45817355 | −1.1936897 |
| 1057 | 0.790964847 | 1.387925398 | −0.18370692 | 1.302393792 |
| 1058 | −1.052897931 | −0.85226912 | 0.90324527 | −1.09684959 |
| 1059 | −0.871565421 | −0.17856476 | 1.51267137 | −1.52734367 |
| 1060 | 3.311161199 | 3.074783921 | 2.10199297 | 1.822541682 |
| 1061 | −0.655128061 | 0.497032417 | 0.92381279 | −0.56348341 |
| 1062 | −0.443129049 | 0.96200606 | 1.51641349 | −0.22974864 |
| 1063 | 1.385675542 | 0.738759296 | 1.1677069 | 0.501211562 |
| 1064 | 1.670680003 | −0.20756775 | −0.73755051 | −0.84924056 |
| 1065 | 1.43532227 | 1.656262941 | −1.09448841 | 1.674272267 |
| 1066 | 1.670680003 | 1.284791101 | 0.14864516 | −0.84985664 |
| 1067 | 2.237616041 | 0.345329863 | −0.60597063 | −0.71581056 |
| 1069 | −0.24632881 | −0.23975349 | −0.01449288 | 0.574861147 |
| 1070 | 1.670680003 | 0.070165381 | −0.64700996 | −0.85055617 |
| 1071 | −1.02687397 | −0.36244273 | 0.13010074 | 0.535909448 |
| 1072 | 1.670680003 | 1.94609957 | 0.19633838 | 1.14825764 |
| 1073 | 2.237616041 | 1.438074134 | 0.31117554 | −0.71786492 |
| 1074 | −0.192632911 | 0.142411101 | 0.79310676 | 0.125548041 |

-continued

| Material No. | MORV value for Equation a.) | MORV Value for Equation b.) | MORV Value for Equation c.) | MORV value for Equation d.) |
|---|---|---|---|---|
| 1075 | 0.909356011 | 0.368597887 | 1.03689838 | 1.001198751 |
| 1076 | 0.812238101 | 0.195908668 | 0.21564664 | 0.219336109 |
| 1077 | 0.325255266 | 1.131242708 | −2.79377204 | −0.62848261 |
| 1078 | 0.325255266 | 1.131242708 | −2.79377204 | −0.62848261 |
| 1079 | 0.85330799 | −0.6855194 | −0.90046979 | −0.46415796 |
| 1081 | −0.131519393 | 0.731836014 | 0.81604919 | −1.29993979 |
| 1082 | 0.744770665 | 0.155243763 | −1.8029919 | 1.023503542 |
| 1083 | 1.415726941 | 0.086297223 | 3.43559555 | −0.12964168 |
| 1084 | 0.161304111 | 0.66712144 | 0.58401752 | 0.373809692 |
| 1085 | −0.72863532 | −0.2873027 | 2.21251376 | 3.003873022 |
| 1088 | −1.1773616 | −0.23258175 | 0.40529195 | 0.994988969 |
| 1089 | 2.769817302 | 1.661618789 | 3.97585272 | 1.059236597 |
| 1090 | 3.052627325 | 0.420821685 | −0.57080756 | 1.751222205 |
| 1091 | −3.379896722 | −3.71174986 | 2.53586709 | 0.644702886 |
| 1093 | 0.72304265 | 1.667011476 | 2.53982093 | 2.7903213 |
| 1095 | 0.744219765 | 1.372184572 | 0.15852396 | 1.126053442 |
| 1097 | 4.407270402 | 2.670641491 | 5.02636153 | 5.361271976 |
| 1098 | −1.85804837 | −2.59071226 | −0.46522239 | 0.655734646 |
| 1099 | 0.745797788 | −0.20547378 | 4.27836342 | 4.646390386 |
| 1102 | 2.068748434 | −0.24299896 | 0.07214682 | −1.11758276 |
| 1104 | 1.018876287 | 0.025163067 | −0.1106021 | 0.838914654 |
| 1105 | 2.387326861 | 3.865456674 | 2.2251199 | 0.728667998 |
| 1107 | 2.352582059 | 2.595496601 | 3.20492728 | 2.844590737 |
| 1110 | 0.302703712 | 0.599942142 | −0.25637571 | −0.03195517 |
| 1111 | 0.750930333 | 0.656784751 | 1.68326413 | 0.329846578 |
| 1112 | −0.205527848 | 0.287622624 | −0.00340777 | 0.59203719 |
| 1115 | 0.999825037 | 0.662221152 | 0.43571192 | 0.342558518 |
| 1116 | 0.873381263 | 1.544324176 | 0.13703728 | −0.38172701 |
| 1117 | −0.682983903 | 1.798204302 | 2.42110319 | −0.39173951 |
| 1118 | 0.069769623 | 0.496895599 | 0.67857133 | −0.14954441 |
| 1119 | −0.671908804 | −0.65984824 | 0.5238174 | −0.85314111 |
| 1120 | 0.953790113 | 1.106552668 | 3.00006904 | 1.585038764 |
| 1121 | −1.184630973 | 2.476138312 | 4.80971952 | 2.450646806 |
| 1122 | −1.02687397 | −0.36244273 | 0.13010074 | 0.535909448 |
| 1125 | 0.387315524 | −0.36101406 | 1.14153708 | −0.75303953 |
| 1126 | 1.021783831 | −0.0070257 | −0.14327539 | 3.954381426 |
| 1127 | 0.990592079 | 0.305612583 | 0.14155512 | −0.29526854 |
| 1128 | 0.990592079 | 0.305612583 | 0.14155512 | −0.29526854 |
| 1129 | 3.18966648 | 3.284362987 | 4.49398568 | 3.950809104 |
| 1131 | 1.650621055 | 1.545704806 | 2.37535081 | 1.259373143 |
| 1133 | −1.519747805 | −0.60804324 | 0.02746106 | 0.590708892 |
| 1134 | 0.815942067 | −0.16126019 | −0.54117238 | 0.613093526 |
| 1135 | 0.626973385 | 1.998305877 | 2.61706075 | 1.570404253 |
| 1136 | 2.812199484 | 1.353198146 | 2.05618426 | 1.869204406 |
| 1137 | 2.208307057 | 1.387136198 | 3.21521374 | 2.069795393 |
| 1138 | 1.670680003 | 1.316442078 | 0.14822999 | −0.46985154 |
| 1139 | 1.408517438 | 0.890457374 | 1.24524408 | 0.685687797 |
| 1140 | 2.765860952 | 2.525539595 | 4.12464228 | 3.833744077 |
| 1141 | −0.484394663 | 0.677713073 | −0.22783646 | −0.37267608 |
| 1142 | 2.54335679 | 4.298105601 | 3.36234238 | 2.684404542 |
| 1143 | 4.204367611 | 3.062126931 | 3.4234313 | 2.072899554 |
| 1144 | 2.479165229 | 3.226545885 | 4.65897152 | 4.952127235 |
| 1145 | 2.479158921 | 3.226545885 | 4.65897152 | 4.952127235 |
| 1146 | 0.774334025 | 1.075800774 | 1.06893156 | 1.011113116 |
| 1147 | 0.844648531 | 1.21935371 | 2.59138595 | 0.805938034 |
| 1148 | 2.906236436 | 1.550674121 | 3.56959167 | 2.832126896 |
| 1149 | 2.837627443 | 3.707154326 | 4.53384262 | 2.625871865 |

Particles

The malodor reduction materials can be practical for inclusion in particles. The particles can comprise about 30% to about 95% by weight of a carrier. The particles can comprise about 0.1% to about 30% by weight of a perfume. The particles can comprise about 0.00025% to about 30% by weight of a malodor agent. The particles can comprise about 0.001% to about 30% by weight of a malodor agent. The malodor agent can comprise one or more reduction materials having a Blocker Index of less than 3 or a Blocker Index average of 3 to about 0.001. The particles can have a mass between about 0.1 mg to about 5 g.

The malodor reduction materials can have a Fragrance Fidelity Index of from about Fragrance Fidelity Index of less than 3, more preferable less than about 2.5 even more preferably less than about 2 and still more preferably less than about 1and most preferably 0 or a Fragrance Fidelity Index average of 3 to about 0.001.

The particles can comprise a weight ratio of parts of malodor agent to perfume of from about 1:20,000 to about 3000:1, optionally from about 1:10,000 to about 1,000:1, optionally 5,000:1 to about 500:1, optionally from about 1:15 to about 1:1.

The particles can comprise one or more malodor reduction materials having a log P greater than 3, preferably greater than 3 but less than 8, preferably said one or more malodor reduction materials are selected from the group consisting of Table 1 materials 1; 2; 3; 7; 9; 10; 11; 13; 14; 18; 21; 22; 23; 25; 28; 29; 30; 31; 32; 33; 35; 36; 38; 39; 47; 48; 49; 50; 52; 57; 62; 63; 64; 67; 68; 69; 71; 74; 75; 76; 77; 78; 79; 80; 83; 85; 91; 92; 93; 100; 101; 102; 103; 104; 105; 109; 114; 119; 120; 122; 123; 128; 134; 135; 137; 140; 142; 145; 148; 149; 152; 153; 158; 159; 161; 162; 174; 175; 176; 177; 178; 182; 183; 184; 185; 186; 189; 192; 195; 196; 197; 206; 208; 209; 210; 211; 212; 215; 221; 227; 228; 229; 230; 231; 233; 234; 238; 242; 243; 244; 246; 252; 253; 260; 261; 263; 267; 269; 271; 274; 276; 277; 280; 285; 289; 290; 292; 293; 294; 295; 296; 300; 301; 303; 307; 316; 317; 318; 322; 324; 325; 328; 329; 330; 331; 333; 334; 335; 336; 338; 339; 342; 343; 344; 349; 352; 356; 358; 359; 360; 361; 362; 363; 364; 368; 369; 370; 371; 372; 378; 381; 385; 386; 388; 390; 391; 397; 398; 413; 414; 416; 418; 421; 424; 426; 428; 429; 432; 441; 444; 449; 453; 457; 459; 461; 462; 463; 465; 466; 467; 468; 470; 471; 473; 475; 478; 479; 480; 482; 484; 486; 487; 488; 497; 498; 501; 502; 503; 505; 519; 520; 521; 524; 529; 532; 534; 537; 541; 544; 548; 550; 552; 558; 559; 560; 561; 562; 563; 565; 566; 567; 568; 569; 570; 571; 572; 573; 574; 577; 578; 582; 584; 589; 591; 592; 594; 599; 600; 601; 603; 604; 606; 607; 608; 609; 610; 611; 613; 614; 615; 616; 618; 620; 621; 624; 625; 626; 628; 631; 632; 633; 635; 644; 650; 653; 659; 660; 661; 663; 671; 673; 674; 675; 676; 677; 678; 679; 680; 681; 684; 686; 691; 692; 693; 694; 696; 697; 698; 700; 702; 704; 706; 707; 708; 709; 710; 711; 712; 713; 714; 715; 716; 717; 718; 719; 720; 721; 722; 723; 724; 725; 726; 727; 731; 741; 746; 750; 752; 754; 757; 758; 763; 766; 769; 770; 771; 774; 775; 776; 778; 781; 782; 788; 791; 800; 802; 804; 806; 814; 821; 826; 827; 828; 831; 837; 839; 840; 849; 850; 852; 856; 866; 868; 869; 870; 871; 872; 873; 876; 877; 878; 879; 881; 884; 885; 886; 890; 892; 893; 894; 905; 908; 912; 913; 914; 916; 919; 920; 922; 925; 926; 927; 930; 933; 939; 941; 942; 943; 945; 947; 948; 950; 951; 953; 954; 959; 965; 967; 973; 978; 985; 988; 998; 1000; 1003; 1006; 1007; 1008; 1009; 1010; 1016; 1022; 1023; 1024; 1025; 1028; 1029; 1031; 1032; 1033; 1035; 1038; 1045; 1046; 1047; 1053; 1057; 1060; 1062; 1063; 1065; 1067; 1070; 1073; 1075; 1077; 1078; 1082; 1089; 1090; 1093; 1095; 1097; 1099; 1102; 1104; 1105; 1107; 1116; 1120; 1121; 1126; 1129; 1131; 1135; 1136; 1137; 1138; 1140; 1142; 1143; 1144; 1145; 1147; 1148; 1149; Table 2 materials 2; 23; 185; 227; 230; 246; 248; 343; 359; 565; 631; 659; 674; 678; 679; 715; 758; 1028; 1097; Table 3 materials 1; 9; 12; 13; 19; 20; 21; 24; 25; 27; 32; 38; 54; 55; 59; 64; 68; 71; 72; 79; 81; 83; 85; 100; 105; 109; 111; 114; 119; 133; 134; 135; 137; 140; 142; 147; 148; 150; 151; 152; 153; 154; 157; 159; 162; 178; 181; 189; 191; 192; 195; 197; 204; 211; 228; 231; 233; 234; 237; 238; 242; 246; 252; 264; 270; 273; 275; 277; 283; 285; 289; 290; 292; 293; 295; 300; 301; 302; 306; 308; 310; 312; 319; 322; 325; 331; 333; 334; 336; 338; 339; 344; 346; 354; 355; 356; 358; 361; 362; 363; 370; 371; 372; 378; 381; 385; 387; 388; 390; 412; 413; 418; 420; 428; 429; 432; 437; 438; 444; 447; 448; 454; 455; 457; 461; 465; 467; 472; 477;

478; 479; 480; 481; 482; 495; 496; 497; 502; 503; 504; 509; 510; 512; 515; 517; 518; 522; 525; 529; 535; 536; 537; 540; 541; 544; 550; 557; 558; 559; 560; 561; 568; 571; 572; 575; 589; 592; 594; 599; 600; 602; 604; 609; 619; 620; 625; 626; 633; 641; 644; 645; 650; 653; 662; 667; 672; 673; 675; 676; 681; 686; 687; 693; 697; 698; 700; 703; 704; 706; 707; 716; 717; 718; 722; 725; 744; 745; 746; 757; 769; 771; 779; 782; 799; 806; 819; 820; 827; 828; 836; 838; 839; 847; 850; 875; 878; 879; 880; 881; 888; 889; 890; 891; 893; 899; 900; 901; 903; 909; 912; 914; 920; 922; 930; 939; 940; 941; 945; 947; 948; 953; 954; 958; 959; 960; 965; 967; 971; 986; 987; 994; 995; 998; 1000; 1001; 1003; 1005; 1008; 1009; 1010; 1011; 1017; 1018; 1023; 1031; 1032; 1046; 1047; 1051; 1052; 1053; 1054; 1055; 1057; 1058; 1061; 1062; 1063; 1074; 1075; 1076; 1082; 1088; 1093; 1095; 1099; 1102; 1104; 1105; 1115; 1116; 1120; 1127; 1128; 1134; 1135; 1141; 1147;1148, 1149, and mixtures thereof; optionally the malodor reduction materials are selected from the group consisting of Table 1 materials 1; 2; 3; 7; 9; 10; 11; 13; 14; 18; 21; 22; 23; 25; 28; 29; 30; 31; 32; 33; 35; 36; 38; 39; 47; 48; 49; 50; 52; 57; 62; 63; 64; 67; 68; 69; 71; 74; 75; 76; 77; 78; 79; 80; 83; 85; 91; 92; 93; 100; 101; 102; 103; 104; 105; 109; 114; 119; 120; 122; 123; 128; 134; 135; 137; 140; 142; 145; 148; 149; 152; 153; 158; 159; 161; 162; 174; 175; 176; 177; 178; 182; 183; 184; 185; 186; 189; 192; 195; 196; 197; 206; 208; 209; 210; 211; 212; 215; 221; 227; 228; 229; 230; 231; 233; 234; 238; 242; 243; 244; 246; 252; 253; 260; 261; 263; 267; 269; 271; 274; 276; 277; 280; 285; 289; 290; 292; 293; 294; 295; 296; 300; 301; 303; 307; 316; 317; 318; 322; 324; 325; 328; 329; 330; 331; 333; 334; 335; 336; 338; 339; 342; 343; 344; 349; 352; 356; 358; 359; 360; 361; 362; 363; 364; 368; 369; 370; 371; 372; 378; 381; 385; 386; 388; 390; 391; 397; 398; 413; 414; 416; 418; 421; 424; 426; 428; 429; 432; 441; 444; 449; 453; 457; 459; 461; 462; 463; 465; 466; 467; 468; 470; 471; 473; 475; 478; 479; 480; 482; 484; 486; 487; 488; 497; 498; 501; 502; 503; 505; 519; 520; 521; 524; 529; 532; 534; 537; 541; 544; 548; 550; 552; 558; 559; 560; 561; 562; 563; 565; 566; 567; 568; 569; 570; 571; 572; 573; 574; 577; 578; 582; 584; 589; 591; 592; 594; 599; 600; 601; 603; 604; 606; 607; 608; 609; 610; 611; 613; 614; 615; 616; 618; 620; 621; 624; 625; 626; 628; 631; 632; 633; 635; 644; 650; 653; 659; 660; 661; 663; 671; 673; 674; 675; 676; 677; 678; 679; 680; 681; 684; 686; 691; 692; 693; 694; 696; 697; 698; 700; 702; 704; 706; 707; 708; 709; 710; 711; 712; 713; 714; 715; 716; 717; 718; 719; 720; 721; 722; 723; 724; 725; 726; 727; 731; 741; 746; 750; 752; 754; 757; 758; 763; 766; 769; 770; 771; 774; 775; 776; 778; 781; 782; 788; 791; 800; 802; 804; 806; 814; 821; 826; 827; 828; 831; 837; 839; 840; 849; 850; 852; 856; 866; 868; 869; 870; 871; 872; 873; 876; 877; 878; 879; 881; 884; 885; 886; 890; 892; 893; 894; 905; 908; 912; 913; 914; 916; 919; 920; 922; 925; 926; 927; 930; 933; 939; 941; 942; 943; 945; 947; 948; 950; 951; 953; 954; 959; 965; 967; 973; 978; 985; 988; 998; 1000; 1003; 1006; 1007; 1008; 1009; 1010; 1016; 1022; 1023; 1024; 1025; 1028; 1029; 1031; 1032; 1033; 1035; 1038; 1045; 1046; 1047; 1053; 1057; 1060; 1062; 1063; 1065; 1067; 1070; 1073; 1075; 1077; 1078; 1082; 1089; 1090; 1093; 1095; 1097; 1099; 1102; 1104; 1105; 1107; 1116; 1120; 1121; 1126; 1129; 1131; 1135; 1136; 1137; 1138; 1140; 1142; 1143; 1144; 1145; 1147; 1148; 1149; Table 2 materials 2; 23; 185; 227; 230; 246; 248; 343; 359; 565; 631; 659; 674; 678; 679; 715; 758; 1028; 1097and mixtures thereof; optionally the malodor reduction materials are selected from the group consisting of Table 4 materials 7; 14; 39; 48; 183; 206; 212; 215; 229; 260; 261; 329; 335; 360; 441; 484; 487; 488; 501; 566; 567; 569; 570; 573; 574; 603; 616; 621; 624; 632; 663; 680; 684; 694; 696; 708; 712; 714; 726; 750; 775; 776; 788; 804; 872; 919; 927; 933; 978; 1007; 1022; 1024; 1029; 1035; 1038; 1060; 1089; 1107; 1129; 1131; 1136; 1137; 1140; 1142; 1143; 1144; 1145; 1148, 1149 Table 5 material 248 and mixtures thereof, optionally the malodor reduction materials are selected from the group consisting of Table 4 materials 261; 680; 788;1129, 1148, 1149 and mixtures thereof. All of the aforementioned odor reduction materials have a log P that is equal to or greater than 3, thus they deposit through the wash especially well. The more selective lists of malodor materials above can be practical for counteracting all of the key malodors.

In one aspect of said product, said malodor reduction materials are not selected from the group consisting of Table 1-3 malodor reduction materials 302; 288; 50; 157; 1017; 888; 64; 1054; 832; 375; 390; 745; 504; 505; 140; 1012; 498; 362; 103; 356; 1074; 908; 1127; 475; 918; 687; 611; 317; 9; 141; 550; 602; 913; 1005; 521; 10; 215; 370; 335; 378; 1121; 360; 565; 1136; 1129; 655; 369; 1065; 914; 757; 601; 478; 889; 891; 358; 973; 162; 554; 522; 312; 125; 26; 418; 92; 586; 1026; 218; 31; 828; 871; 829; 1066; 287; 269; 769; 701; 1118; 70; 946; 142; 109; 108 or mixtures thereof.

The malodor reduction materials can be unencapsulated. The malodor reduction materials can be encapsulated. The malodor agent can comprise one or more encapsulated malodor reduction materials and one or more unencapsulated malodor reduction materials. One or more of the malodor reduction materials can be provided in a delivery system. The delivery system can include a delivery system selected from the group consisting of polymer-assisted delivery, molecular assisted deliver, cyclodextrin deliver, starch encapsulated delivery, zeolite delivery, inorganic delivery, and combinations thereof.

The carrier can be or comprise a material selected from the group consisting of water soluble inorganic alkali metal salt, water-soluble alkaline earth metal salt, water-soluble organic alkali metal salt, water-soluble organic alkaline earth metal salt, water soluble carbohydrate, water-soluble silicate, water soluble urea, and any combination thereof. Alkali metal salts can be, for example, selected from the group consisting of salts of lithium, salts of sodium, and salts of potassium, and any combination thereof. Useful alkali metal salts can be, for example, selected from the group consisting of alkali metal fluorides, alkali metal chlorides, alkali metal bromides, alkali metal iodides, alkali metal sulfates, alkali metal bisulfates, alkali metal phosphates, alkali metal monohydrogen phosphates, alkali metal dihydrogen phosphates, alkali metal carbonates, alkali metal monohydrogen carbonates, alkali metal acetates, alkali metal citrates, alkali metal lactates, alkali metal pyruvates, alkali metal silicates, alkali metal ascorbates, and combinations thereof.

Alkali metal salts can be selected from the group consisting of, sodium fluoride, sodium chloride, sodium bromide, sodium iodide, sodium sulfate, sodium bisulfate, sodium phosphate, sodium monohydrogen phosphate, sodium dihydrogen phosphate, sodium carbonate, sodium hydrogen carbonate, sodium acetate, sodium citrate, sodium lactate, sodium tartrate, sodium silicate, sodium ascorbate, potassium fluoride, potassium chloride, potassium bromide, potassium iodide, potassium sulfate, potassium bisulfate, potassium phosphate, potassium monohydrogen phosphate, potassium dihydrogen phosphate, potassium carbonate, potassium monohydrogen carbonate, potassium acetate, potassium citrate, potassium lactate, potassium tartrate, potassium silicate, potassium, ascorbate, and combinations thereof. Alkaline earth metal salts can be selected from the group consisting of salts of magnesium, salts of calcium, and the like, and combinations thereof. Alkaline earth metal salts can be selected from the group consisting of alkaline metal fluorides, alkaline metal chlorides, alkaline metal bromides, alkaline metal iodides, alkaline metal sulfates, alkaline metal bisulfates, alkaline metal phosphates, alkaline metal monohydrogen phosphates, alkaline metal dihydrogen phosphates, alkaline metal carbonates, alkaline metal monohydrogen carbonates, alkaline metal acetates, alkaline metal citrates, alkaline metal lactates, alkaline metal pyruvates, alkaline metal silicates, alkaline metal ascorbates, and combinations thereof. Alkaline earth metal salts can be selected from the group consisting of magnesium fluoride, magnesium chloride, magnesium bromide, magnesium iodide, magnesium sulfate, magnesium phosphate, magnesium monohydrogen phosphate, magnesium dihydrogen phosphate, magnesium carbonate, magnesium monohydrogen carbonate, magnesium acetate, magnesium citrate, magnesium lactate, magnesium tartrate, magnesium silicate, magnesium ascorbate, calcium fluoride, calcium chloride, calcium bromide, calcium iodide, calcium sulfate, calcium phosphate, calcium monohydrogen phosphate, calcium dihydrogen phosphate, calcium carbonate, calcium monohydrogen carbonate, calcium acetate, calcium citrate, calcium lactate, calcium tartrate, calcium silicate, calcium ascorbate, and combinations thereof. Inorganic salts, such as inorganic alkali metal salts and inorganic alkaline earth metal salts, do not contain carbon. Organic salts, such as organic alkali metal salts and organic alkaline earth metal salts, contain carbon. The organic salt can be an alkali metal salt or an alkaline earth metal salt of sorbic acid (i.e., asorbate). Sorbates can be selected from the group consisting of sodium sorbate, potassium sorbate, magnesium sorbate, calcium sorbate, and combinations thereof.

The carrier can be or comprise a material selected from the group consisting of a water-soluble inorganic alkali metal salt, a water-soluble organic alkali metal salt, a water-soluble inorganic alkaline earth metal salt, a water-soluble organic alkaline earth metal salt, a water-soluble carbohydrate, a water-soluble silicate, a water-soluble urea, and combinations thereof.

The carrier or water soluble-soluble carrier can be selected from the group consisting of sodium chloride, potassium chloride, calcium chloride, magnesium chloride, sodium sulfate, potassium sulfate, magnesium sulfate, sodium carbonate, potassium carbonate, sodium hydrogen carbonate, potassium hydrogen carbonate, sodium acetate, potassium acetate, sodium citrate, potassium citrate, sodium tartrate, potassium tartrate, potassium sodium tartrate, calcium lactate, water glass, sodium silicate, potassium silicate, dextrose, fructose, galactose, isoglucose, glucose, sucrose, raffinose, isomalt, xylitol, candy sugar, coarse sugar, and combinations thereof. In one embodiment, the carrier or water-soluble carrier can be sodium chloride. In one embodiment, the carrier or water-soluble carrier can be table salt.

The carrier can be or comprise a material selected from the group consisting of sodium bicarbonate, sodium sulfate, sodium carbonate, sodium formate, calcium formate, sodium chloride, sucrose, maltodextrin, corn syrup solids, corn starch, wheat starch, rice starch, potato starch, tapioca starch, clay, silicate, citric acid carboxymethyl cellulose, fatty acid, fatty alcohol, glyceryl diester of hydrogenated tallow, glycerol, and combinations thereof.

The carrier can be selected from the group consisting of water soluble organic alkali metal salt, water soluble inorganic alkaline earth metal salt, water soluble organic alkaline earth metal salt, water soluble carbohydrate, water soluble silicate, water soluble urea, starch, clay, water insoluble silicate, citric acid carboxymethyl cellulose, fatty acid, fatty alcohol, glyceryl diester of hydrogenated tallow, glycerol, polyethylene glycol, and combinations thereof.

The carrier can be selected from the group consisting of polyvinyl alcohol, modified polyvinyl alcohol, polyvinyl pyrrolidone, polyvinyl alcohol/polyvinyl pyrrolidone, polyvinyl alcohol/polyvinyl amine, partially hydrolyzed polyvinyl acetate, polyalkylene oxide, polyethylene glycol, acrylamide, acrylic acid, cellulose, alkyl cellulosics, methyl cellulose, ethyl cellulose, propyl cellulose, cellulose ethers, cellulose esters, cellulose amides, polyvinyl acetates, polycarboxylic acids and salts, polyaminoacids or peptides, polyamides, polyacrylamide, copolymers of maleic/acrylic acids, polysaccharides, starch, modified starch, gelatin, alginates, xyloglucans, hemicellulosic polysaccharides, xylan, glucuronoxylan, arabinoxylan, mannan, glucomannan, galactoglucomannan, natural gums, pectin, xanthan, carrageenan, locus bean, arabic, tragacanth, polyacrylates, sulfonated polyacrylates, water-soluble acrylate copolymers, alkylhydroxy cellulosics, methylcellulose, carboxymethylcellulose sodium, modified carboxy-methylcellulose, dextrin, ethylcellulose, propylcellulose, hydroxyethyl cellulose, hydroxypropyl methylcellulose, maltodextrin, polymethacrylates, polyvinyl alcohol copolymers, hydroxypropyl methyl cellulose, and mixtures thereof. A water soluble carrier can be practical.

The particles can comprise from about 40% by weight to about 99% by weight of the particles of the carrier. The carrier can be polyethylene glycol.

The precursor material can comprise more than about 40% by weight polyethylene glycol having a weight average molecular weight from about 2000 to about 13000. Polyethylene glycol (PEG) has a relatively low cost, may be formed into many different shapes and sizes, minimizes unencapsulated perfume diffusion, and dissolves well in water. PEG comes in various weight average molecular weights. A suitable weight average molecular weight range of PEG includes from about 2,000 to about 13,000, from about 4,000 to about 12,000, alternatively from about 5,000 to about 11,000, alternatively from about 6,000 to about 10,000, alternatively from about 7,000 to about 9,000, alternatively combinations thereof. PEG is available from BASF, for example PLURIOL E 8000.

The particles can comprise more than about 40% by weight of the particles of PEG. The particles can comprise more than about 50% by weight of the particles of PEG. The particles can comprise more than about 60% by weight of the particles of PEG. The particles may comprise from about 65% to about 99% by weight of the composition of PEG. The particles may comprise from about 40% to about 99% by weight of the composition of PEG.

Alternatively, the particles can comprise from about 40% to less than about 90%, alternatively from about 45% to about 75%, alternatively from about 50% to about 70%, alternatively combinations thereof and any whole percentages or ranges of whole percentages within any of the aforementioned ranges, of PEG by weight of the particles.

Depending on the application, the particles can comprise from about 0.5% to about 5% by weight of the particles of a balancing agent selected from the group consisting of glycerin, polypropylene glycol, isopropyl myristate, dipropylene glycol, 1,2-propanediol, and PEG having a weight average molecular weight less than 2,000, and mixtures thereof.

The particles can comprise an antioxidant. The antioxidant can help to promote stability of the color and or odor of the particles over time between production and use. The particles can comprise between about 0.01% to about 1% by weight antioxidant. The particles can comprise between about 0.001% to about 2% by weight antioxidant. The particles can comprise between about 0.01% to about 0.1% by weight antioxidant. The antioxidant can be butylated hydroxytoluene.

In addition to the PEG in the particles, the particles can comprise perfume. The perfume can be unencapsulated perfume, encapsulated perfume, or a combination of encapsulated perfume and unencapsulated perfume.

The particles can comprise 0.1% to about 30% by weight perfume, or optionally 0.1% to about 20% by weight perfume. The perfume can be unencapsulated perfume, encapsulated perfume, perfume provided by a perfume delivery technology, or a perfume provided in some other manner Perfumes are generally described in U.S. Pat. No. 7,186,680 at column 10, line 56, to column 25, line 22. The particles can comprise unencapsulated perfume and are essentially free of perfume carriers, such as perfume microcapsules. The particles can comprise perfume carrier materials (and perfume contained therein). Examples of perfume carrier materials are described in U.S. Pat. No. 7,186,680, column 25, line 23, to column 31, line 7. Specific examples of perfume carrier materials may include cyclodextrin and zeolites.

The particles can comprise about 0.1% to about 20%, alternatively about 1% to about 15%, alternatively 2% to about 10%, alternatively combinations thereof and any whole percentages within any of the aforementioned ranges, of perfume by weight of the particles. The particles can comprise from about 0.1% by weight to about 6% by weight of the particles of perfume. The perfume can be unencapsulated perfume and or encapsulated perfume.

The perfume can comprise a perfume raw material having a saturation vapor pressure greater than about 0.01 torr. Such a vapor pressure can be practical for having the perfume be sufficiently volatile to reach the consumers nose when the particles are in use. The composition can comprise a perfume raw material having a logP greater than about 3. Such a logP for the perfume can be practical for having acceptable deposition onto a laundry article, article of clothing. The perfume can comprise a perfume raw material having a saturation vapor pressure greater than about 0.01 torr and a logP greater than about 3. Such a perfume can be practical for providing sufficient volatility for the perfume to reach the consumers nose and sufficient deposition on to a laundry article, article of clothing, textile, or the like.

The particles can be free or substantially free of a perfume carrier. The particles may comprise about 0.1% to about 20%, alternatively about 1% to about 15%, alternatively 2% to about 10%, alternatively combinations thereof and any whole percentages within any of the aforementioned ranges, of unencapsulated perfume by weight of the particles.

The particles can comprise unencapsulated perfume and perfume microcapsules. The particles may comprise about 0.1% to about 20%, alternatively about 1% to about 15%, alternatively from about 2% to about 10%, alternatively combinations thereof and any whole percentages or ranges of whole percentages within any of the aforementioned ranges, of the unencapsulated perfume by weight of the particles. Such levels of unencapsulated perfume can be appropriate for any of the particles disclosed herein that have unencapsulated perfume.

The particles can comprise unencapsulated perfume and a perfume microcapsule but be free or essentially free of other perfume carriers. The particles can comprise unencapsulated perfume and perfume microcapsules and be free of other perfume carriers.

The particles can comprise encapsulated perfume. Encapsulated perfume can be provided as a plurality of perfume microcapsules. A perfume microcapsule is perfume oil enclosed within a shell. The shell can have an average shell thickness less than the maximum dimension of the perfume core. The perfume microcapsules can be friable perfume microcapsules. The perfume microcapsules can be moisture activated perfume microcapsules.

The perfume microcapsules can comprise a melamine/formaldehyde shell. Perfume microcapsules may be obtained from Appleton, Quest International, or International Flavor & Fragrances, or other suitable source. The perfume microcapsule shell can be coated with polymer to enhance the ability of the perfume microcapsule to adhere to fabric. This can be desirable if the particles are designed to be a fabric treatment composition. The perfume microcapsules can be those described in U.S. Patent Pub. 2008/0305982.

The particles can comprise about 0.1% to about 20%, alternatively about 1% to about 15%, alternatively 2% to about 10%, alternatively combinations thereof and any whole percentages within any of the aforementioned ranges, of encapsulated perfume by weight of the particles.

The particles can comprise perfume microcapsules but be free of or essentially free of unencapsulated perfume. The particles may comprise about 0.1% to about 20%, alternatively about 1% to about 15%, alternatively about 2% to about 10%, alternatively combinations thereof and any whole percentages within any of the aforementioned ranges, of encapsulated perfume by weight of the particles.

The particles may comprise dye. The particles may comprise less than about 0.1%, alternatively about 0.001% to about 0.1%, alternatively about 0.01% to about 0.02%, alternatively combinations thereof and any hundredths of percent or ranges of hundredths of percent within any of the aforementioned ranges, of dye by weight of the particles. Examples of suitable dyes include, but are not limited to, LIQUITINT PINK AM, AQUA AS CYAN 15, and VIOLET FL, available from Milliken Chemical.

The particles may have a variety of shapes. The particles may be formed into different shapes include tablets, pills, spheres, and the like. A particle can have a shape selected from the group consisting of spherical, hemispherical, compressed hemispherical, lentil shaped, and oblong. Lentil shaped refers to the shape of a lentil bean. Compressed hemispherical refers to a shape corresponding to a hemisphere that is at least partially flattened such that the curvature of the curved surface is less, on average, than the curvature of a hemisphere having the same radius. A compressed hemispherical particle 10 can have a ratio of height (H) to maximum base dimension B of from about 0.01 to about 0.45, as shown in FIG. 1, alternatively from about 0.1 to about 0.45, alternatively from about 0.1 to about 0.4, alternatively from about 0.2 to about 0.3, the base being the substantially flat surface of the compressed hemispherical particle. Oblong shaped refers to a shape having a maximum dimension and a maximum secondary dimension orthogonal to the maximum dimension, wherein the ratio of maximum dimension to the maximum secondary dimension is greater than about 1.2. An oblong shape can have a ratio of maximum base dimension to maximum minor base dimension greater than about 1.5. An oblong shape can have a ratio of maximum base dimension to maximum minor base dimension greater than about 2. Oblong shaped particles 10 can have a maximum base dimension from about 2 mm to about 6 mm, a maximum minor base dimension of from about 2 mm to about 6 mm Individual particles 10 can have a mass from about 0.1 mg to about 5 g, alternatively from about 10 mg to about 1 g, alternatively from about 10 mg to about 500 mg, alternatively from about 10 mg to about 250 mg, alternatively from about 0.95 mg to about 125 mg, alternatively combinations thereof and any whole numbers or ranges of whole numbers of mg within any of the aforementioned ranges. In a plurality of particles 10, individual particles 10 can have a shape selected from the group consisting of spherical, hemispherical, compressed hemispherical, lentil shaped, and oblong.

An individual particle may have a volume from about 0.003 $cm^3$ to about 0.15 $cm^3$. A number of particles 10 may collectively comprise a dose for dosing to a laundry washing machine or laundry wash basin. A single dose of the particles 10 may comprise from about 1 g to about 27 g. A single dose of the particles 10 may comprise from about 5 g to about 27 g, alternatively from about 13 g to about 27 g, alternatively from about 14 g to about 20 g, alternatively from about 15 g to about 19 g, alternatively from about 18 g to about 19 g, alternatively combinations thereof and any whole numbers of grams or ranges of whole numbers of grams within any of the aforementioned ranges. The individual particles 10 forming the dose of particles 10 that can make up the dose can have a mass from about 0.95 mg to about 2 g. The plurality of particles 10 can be made up of particles 10 having different size, shape, and/or mass. The particles 10 in a dose can have a maximum dimension less than about 1 centimeter.

Particles 10 that have occlusions of gas can be practical for possibly multiple reasons. Such particles 10 can float in a liquid. Particles 10 that have gas entrained therein are comprised of gas inclusions and solid and or liquid materials. Since the particles 10 have gas entrained therein, the particles 10 have a density that is less than the density of the constitutive solid and or liquid materials forming the particle. For instance if the particle is formed of a constitutive material having a density of 1 $g/cm^3$, and the particle is 10% by volume air, the density of the particle is 0.90 $g/cm^3$.

For particles 10 that are used as a laundry scent additive, it can be practical that the particles 10 float in the wash solution of a laundry washing machine. Providing particles 10 that float in a the wash solution of a washing machine can provide the benefit of enhanced perfume bloom during the washing cycle as compared to particles 10 that sink and remain submerged during the washing cycle. As the particles 10 dissolve in the wash, encapsulated perfume and or unencapsulated perfume can be released from the particles 10. Perfume bloom during the washing cycle can be important to the consumer in that it can promote a more pleasant experience to the person doing the laundry and can provide a pleasant scent in the portion of the household in which laundering is conducted.

Further, providing particles 10 that float and comprise malodor reduction materials can help release the malodor reduction materials. The malodor reduction materials can reduce the perceived malodor existing in the laundry room from soiled laundry articles that may have been positioned in the laundry room for a long period of time and have developed malodors.

The particles 10 can be packaged together as a packaged composition comprising a plurality of particles 10. The particles 10 can comprise a carrier, perfume, malodor agent, and occlusions of gas. Without being bound by theory, occlusions of gas are thought to provide for improved strength of the particles 10 as compared to particles 10 having occlusions of gas having other shapes. Spherical occlusions of gas might provide for improved strength over non-spherical occlusions of gas.

Each of the particles 10 can have a density less than 1 $g/cm^3$. Each of the particles 10 can have a density less than about 0.95 $g/cm^3$. Since the density of a typical washing solution is about 1 $g/cm^3$, it can be desirable to provide particles 10 that have a density less than 1 $g/cm^3$ or even less than about 0.95 $g/cm^3$. By having the density less than 1 $g/cm^3$ or even less than about 0.95 $g/cm^3$, it is thought that with the typical manufacturing variability for particle making processes, that nearly all of the particles 10 produced will have a density less than about 1 $g/cm^3$. Having nearly all of the particles 10 have a density less than about 1 $g/cm^3$ can be desirable for providing for particles 10 that float in a wash liquor. The perfume bloom and release of malodor reduction materials that can occur from a wash liquor may be greater for particles 10 that float as compared to particles 10 that sink.

Each of the particles 10 can have a mass between about 0.1 mg to about 5 g. The particles 10 can have a maximum dimension of less than about 20 mm The particles 10 can have a maximum dimension of less than about 10 mm The particles 10 having such a mass and maximum dimension are thought to be readily dissolvable in solutions such a wash solutions used in laundering clothing.

Each of the particles 10 can have a volume and the occlusions of gas within the particles 10 can comprise between about 0.5% to about 50% by volume of the particle, or even between about 1% to about 20% by volume of the particle, or even between about 2% to about 15% by volume of the particle, or event between about 4% to about 12% by volume of the particle. Without being bound by theory, it is thought that if the volume of the occlusions of gas is too great, the particles 10 may not be sufficiently strong to be packaged, shipped, stored, and used without breaking apart in an undesirable manner.

The occlusions of gas can have an effective diameter between about 1 micron to about 2000 microns, or even between about 5 microns to about 1000 microns, or even between about 5 microns to about 200 microns, or even between about 25 to about 50 microns. In general, it is thought that smaller occlusions of gas are more desirable than larger occlusions of gas. If the effective diameter of the occlusions of gas are too large, it is thought that the particles 10 might not be sufficiently strong to be to be packaged, shipped, stored, and used without breaking apart in an undesirable manner. The effective diameter is diameter of a sphere having the same volume as the occlusion of gas. The occlusions of gas can be spherical occlusions of gas.

The particles 10 can be formed into water soluble particles 10 that carry the perfume and the malodor reduction materials. The particles 10 can be formed by a rotoforming process. The particles 10 can be formed on a SANDVIK ROTOFORM 3000 having a 750 mm wide 10 m long belt. The rotoforming cylinder can have 2 mm diameter apertures set at 10 mm pitch in the cross machine direction and 9.35 mm pitch in the machine direction. The rotoforming cylinder be set at about 3 mm above the belt. The belt speed and rotational speed of the rotoforming cylinder can be set at 10 m/min A melt of the precursor material for the particles 10 can be pumped to the rotoforming cylinder at a rate of about 3.1 kg/min from a mixer. A plate and frame heat exchanger can be set to control the temperature to be about 50 degrees Celsius. Upstream of the stator of the rotoformer, a gas feed line and mill can be provided to provide for particles 10 having occlusions of gas if desired. The mill can be a rotor-stator type mill. The mill can be a Quadro Z1 in-line mixer with a single stage of medium rotor stators, operated at about 400 RPM. The mill and gas feed line can be combined in a single unit. An Oakes Foamer (E. T. Oakes Corporation, 686 Old Willets Path, Hauppauge, N.Y. 11788) 2MT1A continuous foamer) can be used to provide the gas feed line, flow regulator, and mill in a single unit.

A precursor material comprising the composition of the particles 10 can be prepared by providing molten carrier into a mixer, which can optionally be a batch mixer. The mixer can be heated so as to help prepare the precursor material at the desired temperature. Perfume can added to the molten carrier, optionally in the mixer. Dye, if present, can be added to the mixer. Other adjunct materials can be added to the precursor material if desired. The precursor material can optionally be prepared by in-line mixing or other known approaches for mixing materials.

Method of Use

Figure 2:
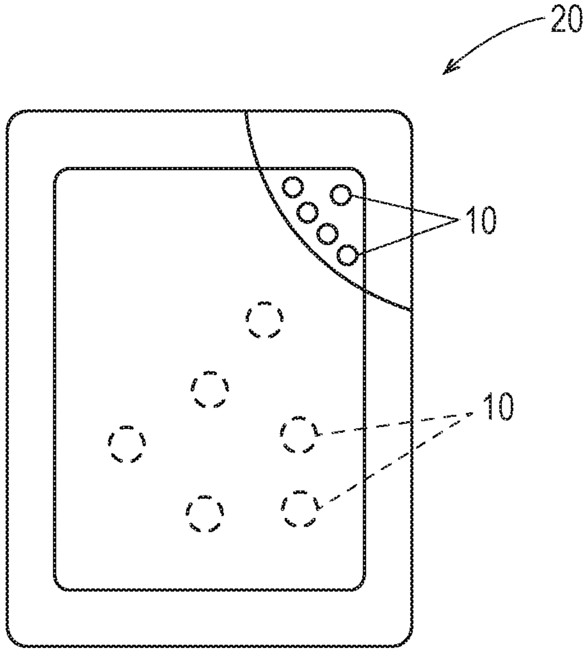
FIG. 2 is a package containing particles.
Figure 3:
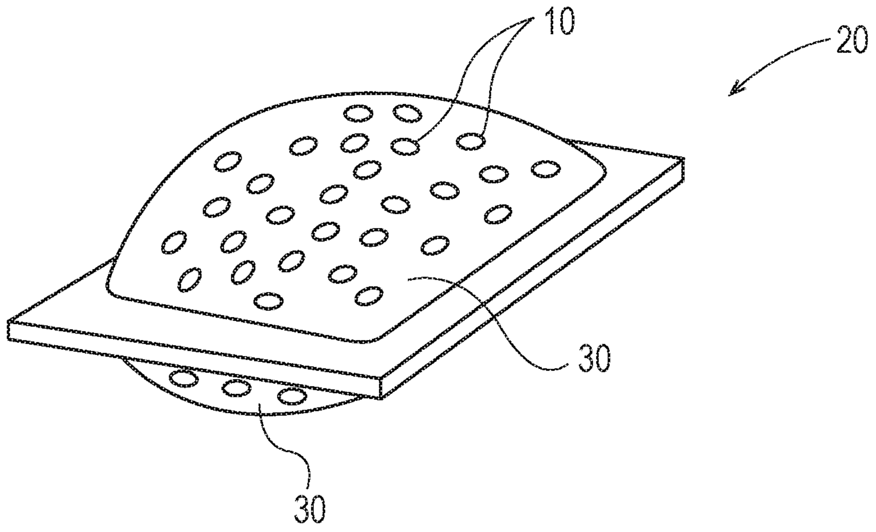
FIG. 3 is a package containing particles.

Any of the particles 10 disclosed herein may be used in any conventional manner. For example, the particles 10 can be used to treat a laundry article. For instance, about 1 g to about 100 g of the particles 10 can be provided in a washing machine or laundry wash basin. The laundry article can be washed in a wash liquor into which the particles 10 are dissolved. The perfume and or malodor reduction materials can form part of the wash liquor. For instance all or a portion of the perfume or perfumes and or malodor reduction material or materials can be dispersed within the wash liquor, dissolved in the wash liquor, exist as a separate phase, or otherwise exist in or be part of the wash liquor. During the wash cycle, all or a portion of the perfume or perfumes and or malodor reduction material or materials can be deposited on the laundry article being washed. All or a portion of the perfume or perfumes and or malodor reduction material may be transported from the wash liquor into the head space above the wash liquor and can be further dispersed into the surroundings of the washing machine or wash basin. The bloom of the malodor reduction materials can help to reduce the impact of malodor present in the room in which the laundry article is washed. The particles 10 can be provided in a fluid pervious package 20, as shown in FIG. 2. The particles 10 can be provided in a water soluble package. The water soluble package 20 can comprise a water soluble film 30, as shown in FIG. 3. The water soluble film can be a polyvinyl alcohol film. The fluid pervious package 20 or water soluble package 20 can contain from about 1 mg to about 100 g of the particles 10.

The laundry article can be treated with a quantity of particles 10 that deliver at least 0.001 mg of malodor agent/kg of laundry article, preferably from about 0.001 mg of malodor agent/kg of laundry article to about 30 mg of malodor agent/kg of laundry article, more preferably from about 0.1 mg of malodor agent/kg of laundry article to about 20 mg of malodor agent/kg of laundry article, most preferably from about 0.2 of malodor agent/kg of laundry article to about 10 mg of malodor agent/kg of laundry article.

The particles 10 can also be used to reduce malodor from a laundry article by providing about 1 g to about 100 g of any of the particles 10 disclosed herein in a fluid pervious package. The fluid pervious package can be a pouch, as shown in FIG. 2. The package can be placed proximal to the laundry article or the package can be contacted with the laundry article. By placing the package proximal to the laundry article or contacting the laundry article with the package one or more of the perfume and the malodor agent can be transferred from the particles 10, through the package, and to the laundry article or the air-space around the laundry article. The mass transfer can occur via diffusion, dispersion, transport of portions of the particles 10 through the package to the laundry article by contact.

Perfumes

The dispersed phase may comprise a perfume that may include materials selected from the group consisting of perfumes such as 3-(4-t-butylphenyl)-2-methyl propanal, 3-(4-t-butylphenyl)-propanal, 3-(4-isopropylphenyl)-2-methylpropanal, 3-(3,4-methylenedioxyphenyl)-2-methylpropanal, and 2,6-dimethyl-5-heptenal, alpha-damascone, beta-damascone, delta-damascone, beta-damascenone, 6,7-dihydro-1,1,2,3,3-pentamethyl-4(5H)-indanone, methyl-7,3-dihydro-2H-1,5-benzodioxepine-3-one, 2-[2-(4-methyl-3-cyclohexenyl-1-yl)propyl]cyclopentan-2-one, 2-sec-butylcyclohexanone, and beta-dihydro ionone, linalool, ethyllinalool, tetrahydrolinalool, and dihydromyrcenol.

Perfume Delivery Technologies

The compositions of the present invention may comprise one or more perfume delivery technologies that stabilize and enhance the deposition and release of perfume ingredients from treated substrate. Such perfume delivery technologies canalso be used to increase the longevity of perfume release from the treated substrate. Perfume delivery technologies, methods of making certain perfume delivery technologies and the uses of such perfume delivery technologies are disclosed in US 2007/0275866 A1.

In one aspect, the compositions of the present invention may comprise from about 0.001% to about 20%, or from about 0.01% to about 10%, or from about 0.05% to about 5%, or even from about 0.1% to about 0.5% by weight of the perfume delivery technology. In one aspect, said perfume delivery technologies may be selected from the group consisting of: perfume microcapsules, pro-perfumes, polymer particles, functionalized silicones, polymer assisted delivery, molecule assisted delivery, fiber assisted delivery, amine assisted delivery, cyclodextrins, starch encapsulated accord, zeolite and inorganic carrier, and mixtures thereof:

In one aspect, said perfume delivery technology may comprise perfume microcapsules formed by at least partially surrounding a benefit agent with a wall material. Said benefit agent may include materials selected from the group consisting of perfumes such as 33-(4-t-butylphenyl)-2-methyl propanal, 3-(4-t-butylphenyl)-propanal, 3-(4-isopropylphenyl)-2-methylpropanal, 3-(3,4-methylenedioxyphenyl)-2-methylpropanal, and 2,6-dimethyl-5-heptenal, alpha-damascone, beta-damascone, delta-damascone, beta-damascenone, 6,7-dihydro-1,1,2,3,3-pentamethyl-4(5H)-indanone, methyl-7,3-dihydro-2H-1,5-benzodioxepine-3-one, 2-[2-(4-methyl-3-cyclohexenyl-1-yl)propyl]cyclopentan-2-one, 2-sec-butylcyclohexanone, and beta-dihydro ionone, linalool, ethyllinalool, tetrahydrolinalool, and dihydromyrcenol. Suitable perfume materials can be obtained from Givaudan Corp. of Mount Olive, N.J., USA, International Flavors & Fragrances Corp. of South Brunswick, N.J., USA, or Quest Corp. of Naarden, Netherlands. In one aspect, the microcapsule wall material may comprise: melamine, polyacrylamide, silicones, silica, polystyrene, polyurea, polyurethanes, polyacrylate based materials, gelatin, styrene malic anhydride, polyamides, and mixtures thereof. In one aspect, said melamine wall material may comprise melamine crosslinked with formaldehyde, melamine-dimethoxyethanol crosslinked with formaldehyde, and mixtures thereof. In one aspect, said polystyrene wall material may comprise polyestyrene cross-linked with divinylbenzene. In one aspect, said polyurea wall material may comprise urea crosslinked with formaldehyde, urea crosslinked with gluteraldehyde, and mixtures thereof. In one aspect, said polyacrylate based materials may comprise polyacrylate formed from methylmethacrylate/dimethylaminomethyl methacrylate, polyacrylate formed from amine acrylate and/or methacrylate and strong acid, polyacrylate formed from carboxylic acid acrylate and/or methacrylate monomer and strong base, polyacrylate formed from an amine acrylate and/or methacrylate monomer and a carboxylic acid acrylate and/or carboxylic acid methacrylate monomer, and mixtures thereof. In one aspect, the perfume microcapsule may be coated with a deposition aid, a cationic polymer, a non-ionic polymer, an anionic polymer, or mixtures thereof. Suitable polymers may be selected from the group consisting of: polyvinylformaldehyde, partially hydroxylated polyvinylformaldehyde, polyvinylamine, polyethyleneimine, ethoxylated polyethyleneimine, polyvinylalcohol, polyacrylates, and combinations thereof. In one aspect, the microcapsule may be a perfume microcapsule. In one aspect, one or more types of microcapsules, for example two microcapsules types having different benefit agents may be used.

In one aspect, said perfume delivery technology may comprise an amine reaction product (ARP) or a thio reaction product. One may also use "reactive" polymeric amines and or polymeric thiols in which the amine and/or thiol functionality is pre-reacted with one or more PRMs to form a reaction product. Typically the reactive amines are primary and/or secondary amines, and may be part of a polymer or a monomer (non-polymer). Such ARPs may also be mixed with additional PRMs to provide benefits of polymer-assisted delivery and/or amine-assisted delivery. Nonlimiting examples of polymeric amines include polymers based on polyalkylimines, such as polyethyleneimine (PEI), or polyvinylamine (PVAm). Nonlimiting examples of monomeric (non-polymeric) amines include hydroxyl amines, such as 2-aminoethanol and its alkyl substituted derivatives, and aromatic amines such as anthranilates. The ARPs may be premixed with perfume or added separately in leave-on or rinse-off applications. In another aspect, a material that contains a heteroatom other than nitrogen and/or sulfur, for example oxygen, phosphorus or selenium, may be used as an alternative to amine compounds. In yet another aspect, the aforementioned alternative compounds can be used in combination with amine compounds. In yet another aspect, a single molecule may comprise an amine moiety and one or more of the alternative heteroatom moieties, for example, thiols, phosphines and selenols. The benefit may include improved delivery of perfume as well as controlled perfume release. Suitable ARPs as well as methods of making same can be found in USPA 2005/0003980 A1and USP 6,413,920 B1.

Test Methods

Malodor reduction materials may be separated from mixtures and indentified by analytical methods that include GC-MS and/or NMR.

Test Method for Determining Saturation Vapor Pressure (VP)

The saturation Vapor Pressure (VP) values are computed for each PRM in the perfume mixture being tested. The VP of an individual PRM is calculated using the VP Computational Model, version 14.02 (Linux) available from Advanced Chemistry Development Inc. (ACD/Labs) (Toronto, Canada) to provide the VP value at 25° C. expressed in units of torr. The ACD/Labs' Vapor Pressure model is part of the ACD/Labs model suite.

Test Method for Determining the Logarithm of the Octanol/Water Partition Coefficient (logP)

The value of the log of the Octanol/Water Partition Coefficient (logP) is computed for each PRM in the perfume mixture being tested. The logP of an individual PRM is calculated using the Consensus logP Computational Model, version 14.02 (Linux) available from Advanced Chemistry Development Inc. (ACD/Labs) (Toronto, Canada) to provide the unitless logP value. The ACD/Labs' Consensus logP Computational Model is part of the ACD/Labs model suite.

Test Method for the Generation of Molecular Descriptors

In order to conduct the calculations involved in the computed-value test methods described herein, the starting information required includes the identity, weight percent, and molar percent of each PRM in the perfume being tested, as a proportion of that perfume, wherein all PRMs in the perfume composition are included in the calculations. Additionally for each of those PRMs, the molecular structure, and the values of various computationally-derived molecular descriptors are also required, as determined in accordance with the Test Method for the Generation of Molecular Descriptors described herein.

For each PRM in a perfume mixture or composition, its molecular structure is used to compute various molecular descriptors. The molecular structure is determined by the graphic molecular structure representations provided by the Chemical Abstract Service ("CAS"), a division of the American Chemical Society, Columbus, Ohio, U.S.A. These molecular structures may be obtained from the CAS Chemical Registry System database by looking up the index name or CAS number of each PRM. For PRMs, which at the time of their testing are not yet listed in the CAS Chemical Registry System database, other databases or information sources may be used to determine their structures. For a PRM which has potentially more than one isomer present, the molecular descriptor computations are conducted using the molecular structure of only one of the isomers, which is selected to represent that PRM. The selection of isomer is determined by the relative amount of extension in the molecular structures of the isomers. Of all the isomers of a given PRM, it is the isomer whose molecular structure that is the most prevalent which is the one that is selected to represent that PRM. The structures for other potential isomers of that PRM are excluded from the computations. The molecular structure of the isomer that is the most prevalent is paired with the concentration of that PRM, where the concentration reflects the presence of all the isomers of that PRM that are present.

A molecule editor or molecular sketching software program, such as ChemDraw (CambridgeSoft/PerkinElmer Inc., Waltham, Mass., U.S.A.), is used to duplicate the 2-dimensional molecular structure representing each PRM. Molecular structures should be represented as neutral species (quaternary nitrogen atoms are allowed) with no disconnected fragments (e.g., single structures with no counter ions). The winMolconn program described below can convert any deprotonated functional groups to the neutral form by adding the appropriate number of hydrogen atoms and will discard the counter ion.

For each PRM, the molecular sketching software is used to generate a file which describes the molecular structure of the PRM. The file(s) describing the molecular structures of the PRMs is subsequently submitted to the computer software program winMolconn, version 1.0.1.3 (Hall Associates Consulting, Quincy, Mass., U.S.A., www.molconn.com), in order to derive various molecular descriptors for each PRM.

As such, it is the winMolconn software program which dictates the structure notations and file formats that are acceptable options. These options include either a MACCS SDF formatted file (i.e., a Structure-Data File); or a Simplified Molecular Input Line Entry Specification (i.e., a SMILES string structure line notation) which is commonly used within a simple text file, often with a ".smi" or ".txt" file name extension. The SDF file represents each molecular structure in the format of a multi-line record, while the syntax for a SMILES structure is a single line of text with no white space. A structure name or identifier can be added to the SMILES string by including it on the same line following the SMILES string and separated by a space, e.g.: C1=CC=CC=C1 benzene.

The winMolconn software program is used to generate numerous molecular descriptors for each PRM, which are then output in a table format. Specific molecular descriptors derived by winMolconn are subsequently used as inputs (i.e., as variable terms in mathematical equations) for a variety of computer model test methods in order to calculate values such as: saturation Vapor Pressure (VP); Boiling Point (BP); logarithm of the Octanol/Water Partition Coefficient (logP); Odor Detection Threshold (ODT); Malodor Reduction Value (MORV); and/or Universal Malodor Reduction Value (Universal MORV) for each PRM. The molecular descriptor labels used in the models' test method computations are the same labels reported by the winMolconn program, and their descriptions and definitions can be found listed in the winMolconn documentation. The following is a generic description of how to execute the winMolconn software program and generate the required molecular structure descriptors for each PRM in a composition.

Computing Molecular Structure Descriptors using winMolconn:

1) Assemble the molecular structure for one or more perfume ingredients in the form of a MACCS Structure-Data File, also called an SDF file, or as a SMILES file.
2) Using version 1.0.1.3 of the winMolconn program, running on an appropriate computer, compute the full complement of molecular descriptors that are available from the program, using the SDF or SMILES file described above as input.
   a. The output of winMolconn is in the form of an ASCII text file, typically space delimited, containing the structure identifiers in the first column and respective molecular descriptors in the remaining columns for each structure in the input file.
3) Parse the text file into columns using a spreadsheet software program or some other appropriate technique. The molecular descriptor labels are found on the first row of the resulting table.
4) Find and extract the descriptor columns, identified by the molecular descriptor label, corresponding to the inputs required for each model.
   a. Note that the winMolconn molecular descriptor labels are case-sensitive.

MORV and Universal MORV calculation

1.) Input Molecular Descriptor values as determined via the method above into the following four equations:

$$\text{MORV}=-8.5096+2.8597\times(\mathit{dxp9})+1.1253\times(\mathit{knotpv})-0.34484\times(\mathit{e}\text{1C2O2})-0.00046231\times(\mathit{idw})+3.3509\times(\mathit{idcbar})+0.11158\times(\mathit{n}\text{2pag22}) \qquad \text{a)}$$

$$\text{MORV}=-5.2917+2.1741\times(\mathit{dxvp5})-2.6595\times(\mathit{dxvp8})+0.45297\times(\mathit{e}\text{1C2C2d})-0.6202\times(\text{c1C2C2})+1.3542\times(\text{CdCH2})+0.68105\times(\text{CaasC})+1.7129\times(\mathit{idcbar}) \qquad \text{b)}$$

$$\text{MORV}=-0.0035+0.8028\times(\text{SHC}\mathit{satu})+2.1673\times(\mathit{xvp7})-1.3507\times(\text{c1C1C3}\mathit{d})+0.61496\times(\mathit{c}\text{1C1O2})+0.00403\times(\mathit{idc})-0.23286\times(\mathit{nd2}). \qquad \text{c)}$$

$$\text{MORV}=-0.9926-0.03882\times(\text{S}\mathit{d}\text{O})+0.1869\times(\text{S}\mathit{sp}\text{3OH})+2.1847\times(\mathit{xp7})+0.34344\times(\text{e1C3O2})-0.45767\times(\mathit{c}\text{1C2C3})+0.7684\times(\text{CKetone}) \qquad \text{d)}$$

Equation a) relates a material's effectiveness in reducing the malodor trans-3-methyl-2-hexenoic acid (carboxylic acid based malodors)

Equation b) relates a material's effectiveness in reducing the malodor trimethylamine (amine based malodors)

Equation c) relates a material's effectiveness in reducing the malodor 3-mercapto-3-methylhexan-1-ol (thiol based malodors)

Equation d) relates a material's effectiveness in reducing the malodor skatole (indole based malodors)

2.) For purpose of the present application, a material's MORV is the highest MORV value from equations 1.)a) through 1.)d).

3.) If all MORVvalues from equations 1.)a) through 1.)d) above are greater than 0.5, the subject material has a Universal MORV.

Method for Assigning Fragrance Fidelity Index (FFI) and the Blocker Index (BI) for a Malodor Reduction Material Blocker materials suitable for use in particles 10 of the present invention are chosen for their ability to decrease malodor, while not interfering with perception of a fragrance. Material selection is done by assigning two indices to a test sample material from two reference scales in order to rank odor strengths. The two reference scales are the Fragrance Fidelity Index (FFI) scale and the Blocker Index (BI) scale. The FFI ranks the ability of the test sample material to impart a perceivable odor which could cause interference when combined with another fragrance and the BI ranks the ability of the test sample material to reduce malodor perception. The two methods for assigning the indices to a test sample on the FFI and the BI reference scales are given below.

Method for Assigning the FFI to Test Samples

The first step in the method for assigning an FFI to the test samples on the FFI reference scale is to create the FFI reference swatches. The swatches for the scale are created by treating clean fabrics swatches with a known amount of a known concentration of an ethyl vanillin solution. Fabric swatches for this test are white knit polycotton (4 inch×4 inch) swatches from EMC ordered as PC 50/50. The supplier is instructed to strip the swatches first, stripping involves washing twice with a fragrance-free detergent and rinsing three times.

Making the FFI Reference Swatches

Make three solutions of ethyl vanillin using a 50%/50% EtOH/water as the diluent at the following concentrations: 25 ppm, 120 ppm and 1000 ppm. Pipette 13 μL of each of the three solutions into the middle of a clean swatch resulting in about a 1 cm diameter of the solution in the middle of the swatch. This will create a sensory scale of three swatches with three different odor levels based on the concentration of the solution pipetted onto the swatch. After drying for 30 minutes in a vented hood, the swatches are wrapped in aluminum foil to prevent odor contamination to the treated swatch. A clean untreated swatch is also included as the lowest anchor point of reference for odor strength on the FFI scale. The FFI reference scale swatches should be used within 0.5 to 12 hours and discarded after 12 hours. The swatches are used as scale anchor points when graders evaluate a test sample(s) and are assigned a Fragrance Fidelity Index (FFI) as show in Table 7.

At least four perfumers/expert graders are used to rank the ethyl vanillin swatches in the FFI scale. The perfumer/expert grader needs to demonstrate adequate discrimination on the scale. The perfumer/expert panel is asked to rank order swatches according to a scale between 0 and 3. The panel must demonstrate statistical differences between the swatches as seen in Table 7.

TABLE 7

Results FFI of reference swatches from six perfumers/expert graders.

| FFI | Swatch | Expert Grader 1 | 2 | 3 | 4 | 5 | 6 | Ave | Std Dev. |
|---|---|---|---|---|---|---|---|---|---|
| 0 | Control: stripped swatch NIL ethyl vanillin | 0 | 0 | 0.5 | 0 | 0 | 0 | 0.08 | 0.2 |
| 1 | Stripped swatch with 13 µL 25 ppm ethyl vanillin | 0.5 | 0.5 | 0.5 | 1.5 | 0.5 | 1.0 | 0.75 | 0.4 |
| 2 | Stripped swatch with 13 µL 120 ppm ethyl vanillin | 2.0 | 1.5 | 1.5 | 2.0 | 2.0 | 2.0 | 1.8 | 0.2 |
| 3 | Stripped swatch with 13 µL 1000 ppm ethyl vanillin | 3.0 | 2.0 | 3.0 | 3.0 | 3.0 | 3.0 | 2.8 | 0.4 |

The expert graders must demonstrate a full range of 2.5 over the 4 swatches to be acceptably discriminating. Grader 2 in table 1 has a range of only 2 and is eliminated from the panel. The panel of expert graders must also demonstrated the ability to statistically discriminate between swatches in the scale.

TABLE 8

This table demonstrates acceptable expert graders with an acceptable range and the panel meets the requirement for discriminating statistics.

| FFI | Swatch | Expert Grader 1 | 3 | 4 | 5 | 6 | Ave | Std Dev. |
|---|---|---|---|---|---|---|---|---|
| 0 | Control: stripped swatch NIL ethyl vanillin | 0 | 0.5 | 0 | 0 | 0 | 0.08 | 0.2 |
| 1 | Stripped swatch with 13 µL 25 ppm ethyl vanillin | 0.5 | 0.5 | 1.5 | 0.5 | 1.0 | 0.80 | 0.4 |
| 2 | Stripped swatch with 13 µL 120 ppm ethyl vanillin | 2.0 | 1.5 | 2.0 | 2.0 | 2.0 | 1.9 | 0.2 |
| 3 | Stripped swatch with 13 µL 1000 ppm ethyl vanillin | 3.0 | 3.0 | 3.0 | 3.0 | 3.0 | 3.0 | 0.0 |

The reference swatches represent the 0, 1, 2, and 3 FFIs on the FFI reference scale, Table 9. The expert grader should familiarize them self with the strength of the odor on the FFI reference swatches by sniffing each one starting at 0 (the lowest odor strength) and ending at 3 (the highest odor strength). This should be done prior to evaluating the test sample material treated swatch.

TABLE 9

Swatch treatments comprising the Fragrance Fidelity Index (FFI) reference scale

| Swatch treatment | Conc. of ethyl vanillin | FFI |
|---|---|---|
| Clean fabric swatch w/ 13 µL ethyl vanillin | 1000 ppm ethyl vanillin | 3 |
| Clean fabric swatch w/ 13 µL ethyl vanillin | 120 ppm ethyl vanillin | 2 |
| Clean fabric swatch w/ 13 µL ethyl vanillin | 25 ppm ethyl vanillin | 1 |
| Clean fabric swatch NIL ethyl vanillin | NIL ethyl vanillin | 0 |

Making Swatches Treated with the Test Material

A clean swatch is treated with 13 µLt of a known concentration of a test sample material resulting in an about 1 cm of the solution on the clean swatch. Just like the reference swatches, the test sample material swatch is dried in a vented hood for 30 minutes and then wrapped in aluminum foil to prevent contamination. The test material swatches and the FFI reference swatches should be made within 2 hours of each other. The test material swatch must be used within 0.5 to 12 hours and discarded after 12 hours.

Assigning the FFI to the test material

At least two perfumers/expert graders are used to assign an FFI grade to a test sample. The perfumer/expert grader smells the test sample swatch by holding that swatch 1 inch from their nose with their nose centered over the area where the test sample was pipetted on to the fabric and then assigns the test sample an FFI grade using the FFI reference scale anchor swatches as references. The test sample swatch is assigned an FFI grade at or between numbers on the FFI scale shown in Table 9. In cases where the test sample material is graded greater than 3, the test material is not a blocker material or the concentration of the material needs to be lowered and reevaluated to determine if a lower level has a malodor blocker functionality.

Method for Assigning the BI to Test Sample

The first step in the method for assigning a BI to a test sample material on the BI reference scale is to create the BI reference swatches. The swatches for the scale are created by treating clean fabrics swatches with a known amount of a known volume of isovaleric acid solution at a known concentration. Fabric swatches for this test are white knit polycotton (4 inch×4 inch) swatches from EMC ordered as PC 50/50. The supplier is instructed to strip the swatches first, stripping involves washing twice with a fragrance-free detergent and rinsing three times.

Making the BI Reference Swatches

Make one solution of 0.08% isovaleric acid using 50%/50% EtOH/water as the diluent. The BI scale contains one clean swatch with no malodor applied. Three other swatches each have a different volume of the 0.08% isovaleric acid applied. Pipette 2 µL of the 0.08% isovaleric acid solution to one clean swatch, 5 µL of the 0.08% isovaleric acid solution to the next swatch and 20 µL of isovaleric acid to the final clean swatch. These solutions are pipetted to the middle of the swatches. This will create a sensory scale of three swatches with three different odor levels based on the volume of the 0.08% isovaleric acid solution pipetted onto the swatch. After drying for 30 minutes in a vented hood, the swatches are wrapped in aluminum foil to prevent odor contamination to the treated swatch. A clean untreated swatch is also included as the lowest anchor point of reference for malodor strength on the BI scale. The BI reference scale swatches should be used within 0.5 to 12 hours and discarded after 12 hours. The swatches are used as scale anchor points when graders evaluate a test sample(s) and are assigned a Blocker Index (BI) as show in Table 12.

At least four perfumers/expert graders are used to rank the isovaleric acid swatches in the BI scale. The perfumer/expert grader needs to demonstrate adequate discrimination on the scale. The perfumer/expert grader is asked to rank order swatches according to a scale between 0 and 3. The panel of graders must demonstrate statistical differences between the swatches as seen in Table 10.

TABLE 10

Results from six perfumers/expert graders to create the BI scale.

| BI | Swatch | Expert Grader 1 | 2 | 3 | 4 | 5 | Ave | Std Dev. |
|---|---|---|---|---|---|---|---|---|
| 0 | Control: stripped swatch NIL isovaleric acid | 0 | 0 | 0 | 0 | 0 | 0 | 0 |
| 1 | Stripped swatch with 2 μL 0.08% isovaleric acid | 0.5 | 2.0 | 1.0 | 1.0 | 0.5 | 1.0 | 0.5 |
| 2 | Stripped swatch with 5 μL 0.08% isovaleric acid | 2.0 | 2.5 | 2.0 | 2.0 | 2.0 | 2.1 | 0.2 |
| 3 | Stripped swatch with 20 μL 0.08% isovaleric acid | 3.0 | 3.0 | 3.0 | 3.0 | 2.5 | 2.8 | 0.2 |

The expert graders must demonstrate a full range of 2.5 over the 4 swatches to be acceptably discriminating. The panel of expert graders must also demonstrated the ability to statistically discriminate between swatches in the scale. Expert grader #2 did not demonstrate the ability to discriminate between the swatches and is eliminated from the panel, see Table 11.

TABLE 11

This table demonstrates acceptable expert graders with an acceptable range and the panel meets the requirement for discriminating statistics.

| BI | Swatch | Expert Grader 1 | 3 | 4 | 5 | Ave | Std Dev. |
|---|---|---|---|---|---|---|---|
| 0 | Control: stripped swatch NIL isovaleric acid | 0 | 0 | 0 | 0 | 0 | 0 |
| 1 | Stripped swatch with 2 μL 0.08% isovaleric acid | 0.5 | 1.0 | 1.0 | 0.5 | 0.8 | 0.3 |
| 2 | Stripped swatch with 5 μL 0.08% isovaleric acid | 2.0 | 2.0 | 2.0 | 2.0 | 2.0 | 0 |
| 3 | Stripped swatch with 20 μL 0.08% isovaleric acid | 3.0 | 3.0 | 3.0 | 2.5 | 2.9 | 0.2 |

The reference swatches represent the 0, 1, 2, and 3 BIs on the BI reference scale, Table 12. The expert grader should familiarizes him/herself with the strength of the odor on the BI reference swatches by sniffing each one starting at 0 (the lowest odor strength) and ending at 3 (the highest odor strength). This should be done prior to evaluating the swatch treated with the test material.

TABLE 12

Swatch treatments comprising the Blocker Index (BI) reference scale.

| Swatch/treatment | Wt of isovaleric acid | BI |
|---|---|---|
| Clean fabric swatch w/ 20 μL 0.08% isovaleric acid | 16 mg isovaleric acid | 3 |
| Clean fabric swatch w/ 5 μL 0.08% isovaleric acid | 4 mg isovaleric acid | 2 |
| Clean fabric swatch w/ 2 μL 0.08% isovaleric acid | 1.6 mg isovaleric acid | 1 |
| Clean fabric swatch NIL isovaleric acid | NIL isovaleric acid | 0 |

Making the Malodorous Swatch and Treating it with a Test Material

To evaluate the BI, the test material is applied to a malodorous swatch to determine how well the test material blocks the malodor. The malodorous swatch is made by treating a clean swatch with 20 μL of a 0.08% solution of isovaleric acid. Dry the malodorous swatch treated with isovaleric acid in a vented hood for 30 minutes. After drying the malodorous swatch a known concentration of test material solution, between 1 ppm and 100 ppm is pipetted onto the malodorous swatch. Apply the test material solution right on top of the spot where the isovaleric acid solution was applied making an about 1 cm diameter spot. Just like the BI reference swatches, the isovaleric acid +test material swatch is dried in a vented hood for 30 minutes and then wrapped in aluminum foil to prevent contamination. The isovaleric acid +test material swatches and the BI reference swatches should be made within 2 hrs of each other. The isovaleric acid+test material swatch must be used between 1-12 hours just like the reference swatches. It is sometimes necessary to evaluate several levels of the test material between about 1and about 100 ppm to determine the BI.

Assigning the BI to the Test Material

At least two perfumers/expert graders are used to assign the BI to the test sample. The expert grader smells the isovaleric acid +test material swatch by holding that swatch one inch from their nose with their nose centered over the area where the test sample was pipetted on to the fabric and then assigns the isovaleric acid +test material swatch a BI based on ranking its odor strength against the odor strength of the swatches in the BI reference scale. The test sample swatch is assigned a BI at or between numbers on the BI in table. In cases where the isovaleric acid+test material swatch odor is greater than 3 on the BI reference scale, this indicates the material is not a blocker or the concentration of the test material needs to be lowered to achieve its blocker functionality.

Malodor Reduction Materials with FFI and BI Grades Based on the Aforementioned

| Table Ref # | CAS# | log P | Name | Conc | FFI | BI |
|---|---|---|---|---|---|---|
| 281 | 54830-99-8 | 3.11 | 3a,4,5,6,7,7a-hexahydro-4,7-methano-1H-indenyl acetate | 10 ppm | 0 | 2.0 |
| | | | | 50 ppm | 0.5 | 2.0 |
| 677 | 139504-68-0 | 3.75 | 1-((2-(tert-butyl)cyclohexyl)oxy)butan-2-ol | 10 ppm | 0 | 2.3 |
| | | | | 50 ppm | 1.8 | 2.0 |
| 962 | 55066-48-3 | 3.17 | 3-methyl-5-phenylpentan-1-ol | 10 ppm | 0 | 2.3 |
| | | | | 50 ppm | 0.5 | 1.7 |
| 261 | 173445-65-3 | 3.29 | 3-(3,3-dimethyl-2,3-dihydro-1H-inden-5-yl)propanal | 10 ppm | 0 | 1.8 |
| | | | | 50 ppm | 1.3 | 1.3 |

-continued

| Table Ref # | CAS# | log P | Name | Conc | FFI | BI |
|---|---|---|---|---|---|---|
| 1139 | 87731-18-8 | 2.11 | (Z)-cyclooct-4-en-1-yl methyl carbonate | 10 ppm<br>50 ppm | 0<br>1.0 | 2.0<br>2.7 |
| | 4430-31-3 | 1.43 | 3,4,4a,5,6,7,8,8a-octahydrochromen-2-one | 10 ppm<br>50 ppm | 0<br>0 | 2.0<br>2.0 |
| 204 | 40379-24-6 | 3.89 | 7-methyloctyl acetate | 10 ppm<br>50 ppm | 0<br>0 | 2.0<br>2.7 |
| 1005 | 93981-50-1 | 5.59 | ethyl (2,3,6-trimethylcyclohexyl) carbonate | 50 ppm | 0.5 | 2.6 |
| 391 | 106-33-2 | 5.73 | Ethyl laurate | 50 ppm | 0.3 | 2.2 |
| 1148 | 1139-30-6 | 4.06 | Caryophyllene Oxide | 50 ppm | 0.5 | 2.3 |
| 524 | 13877-91-3<br>3338-55-4 | 4.31 | 3,7-Dimethyl-1,3,6-Octatriene(cis-β ocimene 70%) | 50 ppm | 0 | 2.8 |
| 1149 | 23787-90-8 | 4 | 1,3,4,6,7,8alpha-hexahydro-1,1,5,5-tetramethyl-2H-2,4alpha-methanophtalen-8(5H)-one | 10 ppm<br>50 ppm | 0<br>0.8 | 1.5<br>2.3 |
| | 112-42-5 | 4.62 | Undecanol | 50 ppm | 0.8 | 2.3 |
| 174 | 112-53-8 | 5.17 | 1-dodecanol | 50 ppm | 0.5 | 2.3 |
| | 98-52-2 | 2.78 | 4-tert-butyl cyclohexane | 10 ppm<br>50 ppm | 0<br>0.3 | 2.0<br>2.0 |
| 109 | 112-39-0 | 6.41 | Methyl palmitate | 10 ppm | | 2.0 |

Malodor Control Materials with Improved Performance at Lower Levels.

Below are some non-limiting examples of preferred behavior by which the malodor control material gives improved malodor control at lower concentration. These nonlimiting data provide additional compelling data that malodor is being blocked, not masked.

| Table Ref # | CAS# | Name | Conc | FFI | BI |
|---|---|---|---|---|---|
| N/A | 68912-13-0 | 8,8-dimethyl-3a,4,5,6,7,7a-hexahydro-1H-4,7-methanoinden-6-yl propionate | 10 ppm<br>50 ppm | 0<br>0 | 1.5<br>2.2 |
| N/A | TBD | 4,8-dimethyl-1-(methylethyl)-7-oxybiciclo[4.3.0]nonane | 10 ppm<br>50 ppm | <br>0.3 | 2.0<br>2.2 |

Retesting Malodor Reduction Compounds at Lower Levels.

The example below demonstrates that while a malodor reduction material could fail to demonstrate odor blocking (BI>2.5) at a higher concentration it should be retested at a lower concentration to determine if it passes.

| Table Ref # | CAS # | Name | Conc | FFI | BI |
|---|---|---|---|---|---|
| N/A | 173445-65-3 | 1H-Indene-5-propanal, 2,3-dihydro-3,3-dimethyl- | 10 ppm<br>50 ppm | 0<br>0.5 | 1.5<br>2.7 |

EXAMPLE 1

Compositions Comprising Malodor Reduction Materials

In the present invention blends enable more potent malodor reduction because blends are useful at a higher % of the product composition before becoming olfactively noticeable. Below are non-limiting examples of malodor reduction agents.

| | | % wt Active | | | | |
|---|---|---|---|---|---|---|
| Component | CAS# | A | B | C | D | E |
| 2,2,8,8-tetramethyl-octahydro-1H-2,4a-methanonapthalene-10-one | 29461-14-1 | 35-45 | 15-25 | 5-20 | 10-30 | 15-25 |
| 1H-Indene-ar-propanal,2,3-dihydro-1,1-dimethyl- | 300371-33-9 | 10-20 | 1-30 | NIL | 5-10 | 1-5 |
| Hexadecanoic acid, (2E)-3,7-dimethyl-2,6-octadien-1-yl ester | 3681-73-0 | 35-45 | 10-25 | NIL | 30-40 | 35-50 |
| 1-Pentanol-3-methyl-5-phenyl | 55066-48-3 | 10-20 | 10-25 | 2-10 | 5-17 | 10 |
| 4,7-Methano-1H-inden-5-ol, 3a,4,5,6,7,7a-hexahydro-, 5-acetate | 171102-41-3 | 0-5 | 10-25 | NIL | 1-6 | 1-5 |
| 4,8-dimethyl-1-(methylethyl)-7-oxybiciclo [4.3.0]nonane | N/A | 0-5 | NIL | NIL | NIL | 1-5 |
| (3Z)-3,7-dimethylocta-1,3,6-triene | 3338-55-4 | NIL | NIL | 10-20 | 2-5 | NIL |
| 1H-Indene-5-propanal, 2,3-dihydro-3,3-dimethyl- | 173445-65-3 | NIL | NIL | NIL | 7.5-16 | 1-15 |
| 3,4,4a,5,6,7,8,8a-octahydrochromen-2-one | 4430-31-3 | NIL | NIL | NIL | 3-7 | 1-15 |
| 1-(2-tert-butylcyclohexyl)oxybutan-2-ol | 139504-68-0 | NIL | NIL | NIL | 0.25-1.5 | NIL |
| ethyl (2,3,6-trimethylcyclohexyl) carbonate | 93981-50-1 | NIL | NIL | 15-30 | NIL | 2 |

-continued

| Component | CAS# | % wt Active A | B | C | D | E |
|---|---|---|---|---|---|---|
| benzyl 2-hydroxypropanoate | 2051-96-9 | NIL | NIL | 2-5 | NIL | NIL |
| (3,5-dimethylcyclohex-3-en-1-yl)methanol | 67634-16-6 | NIL | NIL | 5-30 | NIL | NIL |
| 2-Dodecanol | 10203-28-8 | NIL | 0.25-1 | NIL | 0.5-3 | NIL |

EXAMPLE 2

Compositions Comprising Malodor Reduction Agents

| Ingredient | CAS # | % wt Active A | B | C | B | D | E |
|---|---|---|---|---|---|---|---|
| (E)-1-(2,6,6-trimethyl-1-cyclohex-2-enyl)pent-1-en-3-one | 127-42-4 | 4 | 8 | 2 | 8 | 3 | 2 |
| ethyl dodecanoate | 106-33-2 | NIL | 1 | NIL | 3 | NIL | NIL |
| 3a,4,5,6,7,7a-hexahydro-1H-4,7-methanoinden-1-yl propanoate | 68912-13-0 | 8 | 30 | 1 | 4 | 1 | 3.5 |
| [1R-(1R*,4R*,6R*,10S*)]-4,12,12-trimethyl-9-methylene-5-oxatricyclo[8.2.0.04,6]dodecane | 1139-30-6 | NIL | 0.3 | 2 | 0.5 | NIL | 0.5 |
| (8E)-cyclohexadec-8-en-1-one | 3100-36-5 | NIL | 5 | NIL | 7 | NIL | NIL |
| 3,5,5-trimethylhexyl acetate | 58430-94-7 | 25 | 15 | 50 | 35 | 60 | 56 |
| ethyl (2,3,6-trimethylcyclohexyl) carbonate | 93981-50-1 | NIL | 1 | NIL | 5 | NIL | NIL |
| 2,4-dimethyl-4,4a,5,9b-tetrahydroindeno[1,2-d][1,3]dioxine | 27606-09-3 | 25 | 10 | 15 | 15 | 16 | 15 |
| 2,2,7,7-tetramethyltricyclo[6.2.1.01,6] undecan-5-one | 23787-90-8 | 8 | 9 | 5 | 7 | 5 | 5 |
| (3,5-dimethylcyclohex-3-en-1-yl)methanol | 67634-16-6 | NIL | 0.7 | NIL | 0.5 | NIL | NIL |
| 3-(7,7-dimethyl-4-bicyclo[3.1.1]hept-3-enyl)-2,2-dimethylpropanal | 33885-52-8 | 30 | 20 | 25 | 15 | 15 | 18 |
| Total | | 100 | 100 | 100 | 100 | 100 | 100 |

EXAMPLE 3

Malodor Reduction Agent

| Ingredient | CAS # | % wt Active A | B | C |
|---|---|---|---|---|
| 5-Cyclohexadecen-1-One | 37609-25-9 | 15.0 | 2.00 | 2.00 |
| decahydro-2,2,7,7,8,9,9-heptamethylindeno(4,3a-b)furan | 476332-65-7 | 0.005 | 0.01 | 0.01 |
| 2,3-Dihydro-5,6-dimethoxy-2-(4-piperidinylmethylene)-1H-inden-1-one | 33704-61-9 | 0.3 | 0.5 | 0.5 |
| Cedryl Methyl Ether | 19870-74-7 | 6.0 | 10.0 | 4.0 |
| Trans-4-Decenal | 65405-70-1 | 0.005 | 0.002 | 0.002 |
| Decyl Aldehyde | 112-31-2 | 3.74 | 2.0 | 2.0 |
| 3-methyl cyclopentadecenone | 63314-79-4 | 0.4 | 1.0 | 1.0 |
| Diphenyl Oxide | 101-84-8 | 0.5 | 1.0 | 1.0 |
| 3a,4,5,6,7,7a-hexahydro-4,7-methano-1H-indenyl acetate | 54830-99-8 | 5.0 | 8.0 | 8.0 |
| 3a,4,5,6,7,7a-hexahydro-1H-4,7-methanoinden-1-yl propanoate | 68912-13-0 | 6.0 | 8.0 | 8.0 |

-continued

| Ingredient | CAS # | % wt Active A | B | C |
|---|---|---|---|---|
| 2-(5-methyl-2-propan-2-yl-8-bicyclo[2.2.2]oct-5-enyl)-1,3-dioxolane | 68901-32-6 | 10.0 | 15.0 | 15.0 |
| (E)-3,7-dimethyl-2,6-octadienylhexadecanoate | 3681-73-0 | 10.0 | 10.0 | 16.0 |
| Iso Nonyl Acetate | 58430-94-7 | 6.65 | 8.0 | 3.0 |
| 2,2,7,7-tetramethyltricyclo[6.2.1.01,6]undecan-5-one | 23787-90-8 | 10.0 | 8.0 | 8.0 |
| (1-Methyl-2-(1,2,2-trimethylbicyclo[3.1.0]-hex-3-ylmethyl)cyclopropyl)methanol | 198404-98-7 | 0.1 | 0.3 | 0.3 |
| Lauric Aldehyde | 112-54-9 | 0.625 | 1.0 | 0.7 |
| Methyl Iso Eugenol | 93-16-3 | 18.000 | 10.0 | 13.0 |
| Methyl hexadecanoate | 112-39-0 | 3.000 | 10.0 | 12.0 |
| 2,3-dihydro-1,1-1H-dimethyl-indene-ar-propanal | 300371-33-9 | 0.400 | 0.0 | 0.3 |
| 4-tert-butylcyclohexanol | 98-52-2 | 0.400 | 0.1 | 0.1 |
| 2-isobutyl-4-hydroxy-4-methyltetrahydropyran | 63500-71-0 | 1.600 | 2.0 | 2.0 |
| Undecyl Aldehyde | 112-44-7 | 1.725 | 2.888 | 1.888 |
| Undecylenic Aldehyde | 112-45-8 | 0.550 | 0.2 | 1.2 |
| Total | | 100 | 100.0 | 100.0 |

EXAMPLE 4

Malodor Reducing Agent

| Ingredients | CAS# | % wt Active |
|---|---|---|
| 5-Cyclohexadecen-1-One | 37609-25-9 | 2.6 |
| 2,2,7,7,8,9,9-heptamethyldecahydroindeno[4,3a-b]furan | 647828-16-8 | 0.005 |
| 1,1,2,3,3-pentamethyl-1,2,3,5,6,7-hexahydro-4H-inden-4-one | 33704-61-9 | 0.3 |
| (3R,3aR,6S,7S,8aS)-6-methoxy-3,6,8,8-tetramethyloctahydro-1H-3a,7-methanoazulene | 19870-74-7 | 6 |
| dodecanenitrile | 2437-25-4 | 0.06 |
| Trans 4-Decenal | 65405-70-1 | 0.001 |
| decanal | 112-31-2 | 3 |
| (E)-3-methylcyclopentadec-4-en-1-one | 82356-51-2 | 0.4 |
| oxydibenzene | 101-84-8 | 0.5 |
| Dipropylene Glycol | 25265-71-8 | 0.054 |
| 3a,4,5,6,7,7a-hexahydro-4,7-methano-1H-inden-(5 and 6)-yl acetate | 54830-99-8 | 4 |
| 3-(2-ethylphenyl)-2,2-dimethylpropanal | 67634-15-5 | 3 |
| 3-(3-isopropylphenyl)butanal | 125109-85-5 | 0.6 |
| 8,8-dimethyl-3a,4,5,6,7,7a-hexahydro-1H-4,7-methanoinden-6-yl propionate | 68912-13-0 | 6 |
| 2-(8-isopropyl-6-methylbicyclo[2.2.2]oct-5-en-2-yl)-1,3-dioxolane | 68901-32-6 | 10 |
| d E)-3,7-dimethylocta-2,6-dien-1-yl palmitate | 3681-73-0 | 10 |
| 7-methyloctyl acetate | 40379-24-6 | 3 |

-continued

| Ingredients | CAS# | % wt Active |
|---|---|---|
| 2,2,7,7-tetramethyltricyclo(6.2.1.0(1,6))-undecan-5-one | 23787-90-8 | 10 |
| (1-methyl-2-((1,2,2-trimethylbicyclo[3.1.0]hexan-3-yl)methyl)cyclopropyl)methanol | 198404-98-7 | 0.1 |
| dodecanal | 112-54-9 | 0.6 |
| Linalyl Benzoate | 126-64-7 | 1.74 |
| 4-(tert-butyl)cyclohexyl acetate | 32210-23-4 | 4 |
| octahydro-1H-4,7-methanoindene-1-carbaldehyde | 30772-79-3 | 0.26 |
| methyl 2-(3-oxo-2-pentylcyclopentyl)acetate | 24851-98-7 | 4.15 |
| (Z)-1,2-dimethoxy-4-(prop-1-en-1-yl)benzene | 93-16-3 | 18.23 |
| Methyl Palmitate | 112-39-0 | 3 |
| 3-(3,3-dimethyl-2,3-dihydro-1H-inden-5-yl)propanal | 300371-33-9 | 0.4 |
| 4-tert-butyl cyclohexanol | 98-52-2 | 0.05 |
| 3-methyl-5-phenylpentan-1-ol | 55066-48-3 | 3.5 |
| 2-isobutyl-4-methyltetrahydro-2H-pyran-4-ol | 63500-71-0 | 1.6 |
| (E)-4-methyldec-3-en-5-ol | 81782-77-6 | 0.8 |
| undecanal | 112-44-7 | 1.7 |
| undec-10-enal | 112-45-8 | 0.35 |

EXAMPLE 5

Particles Comprising a Malodor Agent

Examples of Particles 10 that Comprise a Malodor Reduction Agent

| Component | Function | GCAS/CAS | Blue Formula Wt % | Purple Formula Wt % | Green Formula Wt % |
|---|---|---|---|---|---|
| PEG 8000 | Carrier | 95229421 | 80.79% | 80.85% | 80.89% |
| 1-((2-(tert-butyl)cyclohexyl)oxy)butan-2-ol | Malodor reduction | 139504-68-0 | 9.60% | 9.60% | 9.60% |
| Malodor reduction agent of Example 5 | Malodor reduction | | 2.40% | 2.40% | 2.40% |
| Blue AH | Dye | 95559345 | 0.0021% | | |
| Liquitint Violet FL | Dye | 92038834 | | 0.015% | |
| Liquitint Green 101 | Dye | 10053851 | | | 0.0011% |

-continued

| Component | Function | GCAS/CAS | Blue Formula Wt % | Purple Formula Wt % | Green Formula Wt % |
|---|---|---|---|---|---|
| Water | Carrier | | 0.2079% | 0.1350% | 0.1089% |
| Unencapsulated Perfume | Perfume | | 7.00% | 7.00% | 7.00% |

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as “40 mm” is intended to mean “about 40 mm ”

Every document cited herein, including any cross referenced or related patent or application is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests, or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is, therefore, intended to cover in the appended claims all such changes and modifications that are within the scope of this invention.

What is claimed:

1. A composition comprising a plurality of particles, wherein said particles comprise:

about 30% to about 95% by weight of a carrier;

about 0.1% to about 30% by weight of a perfume; and about 0.00025% to about 30% by weight of a malodor agent;

wherein said malodor agent comprises one or more malodor reduction materials having a Blocker Index of less than 3 or a Blocker Index average of 3 to about 0.001; and wherein each of said particles has a mass between about 0.1 mg to about 5 g.

2. The composition according to claim 1, wherein said carrier is selected from the group consisting of water soluble organic alkali metal salt, water soluble inorganic alkaline earth metal salt, water soluble organic alkaline earth metal salt, water soluble carbohydrate, water soluble silicate, water soluble urea, starch, clay, water insoluble silicate, citric acid carboxymethyl cellulose, fatty acid, fatty alcohol, glyceryl diester of hydrogenated tallow, glycerol, polyethylene glycol, and combinations thereof.

3. The composition according to claim 1, wherein said carrier is selected from the group consisting of polyvinyl alcohol, modified polyvinyl alcohol, polyvinyl pyrrolidone, polyvinyl alcohol/polyvinyl pyrrolidone, polyvinyl alcohol/polyvinyl amine, partially hydrolyzed polyvinyl acetate, polyalkylene oxide, polyethylene glycol, acrylamide, acrylic acid, cellulose, alkyl cellulosics, methyl cellulose, ethyl cellulose, propyl cellulose, cellulose ethers, cellulose esters, cellulose amides, polyvinyl acetates, polycarboxylic acids and salts, polyaminoacids or peptides, polyamides, polyacrylamide, copolymers of maleic/acrylic acids, polysaccharides, starch, modified starch, gelatin, alginates, xyloglucans, hemicellulosic polysaccharides, xylan, glucuronoxylan, arabinoxylan, mannan, glucomannan, galactoglucomannan, natural gums, pectin, xanthan, carrageenan, locus bean, arabic, tragacanth, polyacrylates, sulfonated polyacrylates, water-soluble acrylate copolymers, alkylhydroxy cellulosics, methylcellulose, carboxymethylcellulose sodium, modified carboxy-methylcellulose, dextrin, ethylcellulose, propylcellulose, hydroxyethyl cellulose, hydroxypropyl methylcellulose, maltodextrin, polymethacrylates, polyvinyl alcohol copolymers, hydroxypropyl methyl cellulose, and mixtures thereof.

4. The composition according claim 1, wherein said carrier is water soluble.

5. The composition according to claim 1, wherein said perfume comprises encapsulated perfume.

6. The composition according to claim 5, wherein said carrier is polyethylene glycol having a weight average molecular weight from about 2000 to about 13000.

7. The composition according to claim 1, wherein at least a portion of said malodor agent is unencapsulated.

8. The composition according to claim 1, wherein at least a portion of said malodor agent is encapsulated.

9. The composition according to claim 1, wherein said particles comprise occlusions of gas.

10. The composition according to claim 9, wherein said perfume comprises unencapsulated perfume.

11. The composition according to claim 10, wherein each of said particles has a volume and said occlusions of gas within said particles comprise between about 0.5% to about 50% by volume of said particles.

12. The composition according to claim 11, wherein said occlusions of gas have an effective diameter between about 1 micron to about 2000 microns.

13. The composition according to claim 12, wherein said occlusions of gas are spherical occlusions of gas.

14. The composition according to claim 1, wherein said malodor reduction materials have a Fragrance Fidelity Index of from about 3 to about 0.001.

15. The composition according to claim 1, wherein said malodor agent comprises one or more malodor reduction materials having a log P greater than 3 and said one or more malodor reduction materials are selected from the group consisting of 2-ethylhexyl (Z)-3-4-methoxyphenyl)acrylate; 2,4-dimethyl-2-(5,5,8,8-tetramethyl-5,6,7,8-tetrahydronaphthalen-2-yl)-1,3-dioxolane; 1,1-dimethoxynon-2-yne; 3-methoxy-7,7-dimethyl-10-methylenebicyclo[4.3.1]decane; methoxycyclododecane; 1,1-dimethoxycyclododecane; (Z)-tridec-2-enenitrile; (2-hydroxy-4-methoxyphenyl)(phenyl)methanone; 2,4a,5,8a-tetramethyl-1,2,3,4,4a,7,8,8a-octahydronaphthalen-1-yl formate; 1,8-dioxacycloheptadec an-9-one; 4-(tert-pentyl)cyclohexan-1-one; 2-methoxy-1,1'-biphenyl; 3a,5,6,7,8,8b-hexahydro-2,2,6,6,7,8,8-heptamethyl-4H-indeno(4,5-d)-1, 3-dioxole; 7-isopropyl-8,8-dimethyl-6,10-dioxaspiro[4.5] decane; octyl furan-2-carboxylate; octyl acetate; 2-heptyl-4-methyl-1,3-dioxolane; octanal; 1,1-dimethoxyoctane; 7-methyl-3-methyleneocta-1,6-diene; 2-methyl-6-methyleneoct-7-en-2-yl acetate; tetradecanal; tetradecanenitrile; 2,2,6,8-tetramethyl-1,2,3,4,4a,5,8,8a-octahydronaphthalen-1-ol; 2-((1S,5R)-6,6-dimethylbicyclo[3.1.1]hept-2-en-2-yl) ethyl acetate; (4R,4aS,6R)-4,4a-dimethyl-6-(prop-1-en-2-yl)-4,4a,5,6,7,8-hexahydronaphthalen-2(3H)-one; nonan-1-ol; nonanal; 12-methyl-14-tetradec-9-enolide; N-ethyl-2-isopropyl-5-methylcyclohexane-1-carboxamide; 2-methoxynaphthalene; (E)-3,7,11-trimethyldodeca-1,6,10-trien-3-ol; (Z)-3,7-dimethylocta-2,6-dien-1-ol; methyl (E)-non-2-enoate; 10-isopropyl-2,7-dimethyl-1-oxaspiro[4.5] deca-3,6-diene; 2-(2-(4-methylcyclohex-3-en-1-yl)propyl) cyclopentan-1-one; (E)-4-(2,2,3,6-tetramethylcyclohexyl) but-3-en-2-one; (4-(4-methylpent-3-en-1-yl)cyclohex-3-en-1-yl)methyl acetate; 2-(tert-butyl)-4,5,6-trimethyl-1,3-phenylene dinitrite; 1,7-dioxacycloheptadecan-8-one; 1-(4-(tert-butyl)-2,6-dimethyl-3,5-dinitrophenyl)ethan-1-one; 1-(tert-butyl)-2-methoxy-4-methyl-3,5-dinitrobenzene; 3-methylcyclopentadecan-1-one; (E)-3-methylcyclopentadec-4-en-1-one; 1-(4-isopropylcyclohexyl)ethan-1-ol; (E)-dec-5-enoic acid; methyl non-2-ynoate; 2-methyldecanal; 6,6-dimethoxy-2,5,5-trimethylhex-2-ene; methyl stearate; 1,1-dimethoxy-2-methylundecane; undecan-2-one; 2-methylundecanal; methyl tetradecanoate; methyl (9Z, 12Z)-octadeca-9,12-dienoate; methyl palmitate; 1-methyl-2-phenoxybenzene; 1-allyl-4-methoxybenzene; 1-(naphthalen-2-yl)ethan-1-one; methyl oct-2-ynoate; methyl 2,6,6-trimethylcyclohex-2-ene-1-carboxylate; 7-isopropyl-10-methyl-1,5-dioxaspiro[5.5]undecan-3-ol; 3-(3-(tert-butyl) phenyl) -2-methylpropanal; (E)-4-(4,8-dimethylnona-3,7-dien-1-yl)pyridine; (E)-trideca-3,12-dienenitrile; 2,2-dimethyl-3-(m-tolyl)propan-1-ol; 8-isopropyl-6-methylbicyclo[2.2.2]oct-5-ene-2-carbaldehyde; (S)-1-methyl-4-(prop-1-en-2-yl)cyecyclohex-1-ene; 3,7-dimethylocta-1,6-dien-3-yl octanoate; 3,7-dimethylocta-1, 6-dien-3-yl isobutyrate; 3,7-dimethylocta-1,6-dien-3-yl benzoate; 3,7-dimethylocta-1,6-dien-3-yl 2-aminobenzoate; (2Z,6E)-3,7-dimethylnona-2,6-dienenitrile; 3-(4-methylcyclohex-3-en-1-yl)butanal; (2,5-dimethyl-1,3-dihydroinden-2-yl)methanol; 3-(4-(tert-butyl)phenyl)-2-methylpropanal; dodecan-1-ol; dodecyl acetate; dodecanoic acid; 5-hexyl-5-methyldihydrofuran-2(3H)-one; dodecanal; 4-(1-ethoxyvinyl)-3,3,5,5-tetramethylcyclohexan-1-one; ((3S,3aR,6R, 8aS)-7,7-dimethyl-8-methyleneoctahydro-1H-3a,6-methanoazulen-3-yl)methanol; 5-(sec-butyl)-2-(2,4-dimethylcyclohex-3-en-1-yl)-5-methyl-1,3-dioxane; (1-methyl-2-((1,2,2-trimethylbicyclo[3.1.0]hexan-3-yl) methyl)cyclopropyllmethanol; 2-propylheptanenitrile; 2-hexylcyclopentan-1-one; 2,6,9,10-tetramethyl-1-oxaspiro (4.5)deca-3,6-diene; isopropyl palmitate; isopropyl tetradecanoate; isopropyl dodecanoate; (E)-cyclohexadec-8-en-1-one; (2S,5S)-2-isopropyl-5-methylcyclohexan-1-one; 2-hexylcyclopent-2-en-1-one; (2S,5S)-2-isopropyl-5-methylcyclohexan-1-one; 4-(4-methylpent-3-en-1-yl)cyclohex-3-ene-1-carbaldehyde; (Z)-1-(benzyloxy)-2-methoxy-4-(prop-1-en-1-yl)benzene; 1-((2S,3S)-2,3,8,8-tetramethyl-1, 2,3,4,5,6,7,8-octahydronaphthalen-2-yl)ethan-1-one; 6-(sec-butyl)quinoline; 2-(cyclohexyloxy)-1,7,7-trimethylbicyclo[2.2.1]heptane; (1R,2R,4S)-1,7,7-trimethylbicyclo [2.2.1]heptan-2-yl propionate; (1S,2S,4S)-1,7,7-trimethylbicyclo[2.2.1]heptan-2-yl isobutyrate; 4-(( 2 R)-1,7,7-trimethylbicyclo[2.2.1]heptan-2-yl)cyclohexan-1-ol; (1R, 4S)-1,7,7-trimethylbicyclo[2.2.1]heptan-2-yl acetate; 2-(4-isopropylcyclohexa-1,4-dien-1-yl)ethyl formate; isopentyl (E)-undec-6-enoate; isopentyl dodecanoate; (E)-oxacycloheptadec-10-en-2-one; (E)-non-2-enenitrile; (E)-8-(1H-indol-1-yl)-2,6-dimethyloct-7-en-2-ol; 8,8-di(1H-indol -1-yl)-2,6-dimethyloctan-2-ol; 2-cyclododecylpropan-1-ol; 3-methyl-5-phenylpentanenitrile; 2,3-dihydro-3,3-dimethyl-1H-indene-5-propanal; 3-(3,3-dimethyl-2,3-dihydro-1H-inden-5-yl)propanal; hexyl octanoate; hexyl hexanoate; (Z)-2-benzylideneoctanal; hexyl benzoate; (Z)-hex-1-en-1-yl (Z)-2-methylbut-2-enoate; (E)-3,7-dimethylocta-2,6-dien-1-yl palmitate; oxacycloheptadecan-2-one; ethyl (1R,2R,3R, 4R)-3-isopropylbicyclo[2.2.1]hept-5-ene-2-carboxylate; 2-(1-(3,3-dimethylcyclohexyl)ethoxy)-2-methylpropyl propionate; (E)-oxacyclohexadec-13-en-2-one; 6-butyl-2,4-dimethyl-3,6-dihydro-2H-pyran; 2-((3S,5R,8S)-3,8-dimethyl-1,2,3,4,5,6,7,8-octahydroazulen-5-yl)propan-2-ol; 1-(2,6,6-trimethylcyclohex-2-en-1-yl)pentan-3-one; ethyl 2-ethyl-6, 6-dimethylcyclohex-2-ene-1-carboxylate; (1Z,5Z)-1,5-dimethyl-8-(propan-2-ylidene)cyclodeca-1,5-diene; (1E, 6E)-8-isopropyl-1-methyl-5-methylenecyclodeca-1,6-diene; (E)-3,7-dimethylocta-2,6-dien-1-yl 2-phenylacetate; (E)-3,7-dimethylocta-2,6-dien-1-yl 2-phenylacetate; (6E, 10E)-3,7,11,15-tetramethylhexadeca-1,6,10,14-tetraen-3-ol; (E)-2-(3,7-dimethylocta-2,6-dien-1-yl)cyclopentan-1-one; 5-heptyldihydrofuran-2(3H)-one; 1-methyl-4-(propan-2-ylidene)cyclohexyl acetate; 1-methyl-4-(propan-2-ylidene) cyclohexan-1-ol; (1R,4aR,8aS)-1-isopropyl-7-methyl-4-methylene-1,2,3,4,4a,5,6,8a-octahydronaphthalene; (Z)-4-(2,2-dimethyl-6-methylenecyclohexyl)but-3-en-2-one; (4aS,9aR)-3,5,5,9-tetramethyl-2,4a,5,6,7,9a-hexahydro-1H-benzo[7]annulene; (1R,3aR,4R,7R)-1,4-dimethyl-7-(prop-1-en-2-yl)-1,2,3,3a,4,5,6,7-octahydroazulene; 2-((2R,4aR)-4a,8-dimethyl-1,2,3,4,4a,5,6,7-octahydronaphthalen-2-yl) propan-2-ol; 5-octyldihydrofuran-2(3H)-one; (Z)-1-(2,2-dimethyl-6-methylenecyclohexyl)but-2-en-1-one; (1R,4aS, 8aS)-1-isopropyl-7-methyl-4-methylene-1,2,3,4,4a,5,6,8a-octahydronaphthalene;1-(3,3-dimethylcyclohexyl)pent-4-en-1-one; 4,6,6,7,8,8-hexamethyl-1,3,4,6,7,8-hexahydrocyclopenta[g]isochromene; furan-2-ylmethyl octanoate; furan-2-ylmethyl hexanoate; furan-2-ylmethyl heptanoate; 2-methyldecanenitrile; 8,8-dimethyl-3a,4,5,6,7, 7a-hexahydro-1H-4,7-methanoinden-6-yl propionate; ethyl (3aR,4S,7R,7aR)-octahydro-3aH-4,7-methanoindene-3a-carboxylate; (6-isopropyl-9-methyl-1,4-dioxaspiro[4.5]decan-2-yl)methanol; undec-10-enenitrile; 3-(2-ethylphenyl)-2,2-dimethylpropanal; (E)-4,8-dimethyldeca-4,9-dienal; (E)-4-((3aR,4R,7R,7aR)-1,3a,4,6,7,7a-hexahydro-5H-4,7-methanoinden-5-ylidene)-3-methylbutan-2-ol; 8,8-dimethyl-3a,4,5,6,7,7a-hexahydro-1H-4,7-methanoinden-6-yl acetate; 3-(4-ethylphenyl)-2,2-dimethylpropanenitrile; 2-heptylcyclopentan-1-one; 1-ethoxyethoxy Cyclododecane; 3-cyclohexene-1-carboxylic acid, 2,6,6-trimethyl-, methyl ester; (2E,6E)-3,7,11-trimethyldodeca-2,6,10-trien-1-yl acetate; (2E,6E)-3,7,11-trimethyldodeca-2,6,10-trien-1-ol; oxacyclohexadecan-2-one; (E)-cyclopentadec-4-en-1-one; 1-cyclopentadec-4-en-1-one; 1,4-dioxacycloheptadecane-5,17-dione; ethyl undec-10-enoate; ethyl palmitate; ethyl nonanoate; ethyl tetradecanoate; (E)-3,7-dimethylnona-1,6-dien-3-ol; ethyl dodecanoate; ethyl decanoate; ethyl 6,6-dimethyl-2-methylenecyclohex-3-ene-1-carboxylate; 6-ethyl-2,10,10-trimethyl-1-oxaspiro[4.5] deca-3,6-diene; 2-9(1R,3S,4S)-4-methyl-3-(prop-1-en-2-yl)-4-vinylcyclohexyl)propan-2-ol; (E)-3-methyl-5-(2,2,3-trimethylcyclopent-3-en-1-yl)pent-4-en-2-ol; (E)-4-((3aS, 7aS)-octahydro-5H-4,7-methanoinden-5-ylidene)butanal; 1,1-dimethoxydodecane; (R)-1-methyl-4-(prop-1-en-2-yl) cyclohex-1-ene; 7,9-Dimethylspirol[5.5]undecan-3-one; oxydibenzene; diphenylmethane; 2-methyl-1-phenylpropan- 2-yl butyrate; octahydro-1H-4,7-methanoinden-5-yl acetate; 2-methyl-5-(prop-1-en-2-yl)cyclohexyl acetate; 3,7-dimethyloct-6-en-3-ol; dibutylsulfane; 1,2-diphenylethane; 6-hexyltetrahydro-2H-pyran-2-one; (3R,4R)-1-isopropyl-4-methyl-3-(prop-1-en-2-yl)-4-vinylcyclohex-1-ene; (3S,3aS,5R)-3,8-dimethyl-5-(prop-1-en-2-yl)-1,2,3,3a,4,5,6,7-octahydroazulene; 6-heptyltetrahydro-2H-pyran-2-one; (1S,8aR)-4,7-dimethyl-1-(prop an-2-yl)-1,2,3,5,6,8a-hexahydronaphthalene; (Z)-1((1R,2S)-2,6,6-trimethylcyclohex-3-en-1-yl)but-2-en-1-one; (1S,8aS)-1-isopropyl-4,7-dimethyl-1,2,3,5,6,8a-hexahydronaphthalene; 3,7,7-trimethylbicyclol[4.1.0]hept-3-ene; dec-9-en-1-ol; decyl propionate; 1,1-diethoxydecane; 1-cyclohexylethyl (E)-but-2-enoate; 3-(4-isopropylphenyl)-2-methylpropanal; cyclotetradecane; cyclopentadecanone; cyclohexyl 2-hydroxybenzoate; 3a,4,5,6,7,7a-hexahydro-1H-4,7-methanoinden-6-yl butyrate; 8,8-dimethyl-1,2,3,4,5,6,7,8-octahydronaphthalene-2-carbaldehyde; 3a,4,5,6,7,7a-hexahydro-1H-4,7-methanoinden-5-yl isobutyrate; (5R,6R)-3,6-dimethyl-5-(prop-1-en-2-yl)-6-vinyl-4,5,6,7-tetrahydrobenzofuran; 2-(3-phenylpropyl)pyridine; dodecanenitrile; (E)-cycloheptadec-9-en-1-one; 3-(4-methylcyclohex-3-en-1-yl)but-3-en-1-yl acetate; 3-(4-methylcyclohex-3-en-1-yl)butan-1-ol; (E)-3-methyl-5-phenylpent-2-enenitrile; (E)-2-(2,6-dimethylhepta-1,5-dien-1-yl)-4-methyl-1,3-dioxolane; (E)-1,1-dimethoxy-3,7-dimethylocta-2,6-diene; (E)-1,1-diethoxy-3,7-dimethylocta-2,6-diene; (E)-3,7-dimethylocta-1,3,6-triene; (E)-oxacycloheptadec-11-en-2-one; (Z)-dec-4-enal; (E)-hex-3-en-1-yl (E)-hex-3-enoate; (Z)-hex-3-en-1-yl 2-hydroxybenzoate; (Z)-hex-3-en-1-yl benzoate; (Z)-hex-3-en-1-yl 2-methylbutanoate; cinnamyl propionate; cinnamyl isobutyrate; cinnamyl cinnamate; hexadecan-1-ol; (E)-1-(2,6,6-trimethylcyclohex-2-en-1-yl)hepta-1,6-dien-3-one; 2-methyl-4-(2,6,6-trimethylcyclohex-1-en-1-yl)butanal; (3aR,5aR,9aR,9bR)-3a,6,6,9a-tetramethyldodecahydronaphtho[2,1-b]furan; 1,6-dioxacycloheptadecan-7-one; 1-(6-(tert-butyl)-1,1-dimethyl-2,3-dihydro-1H-inden-4-yl)ethan-1-one; (3R,3aR,6S,7S,8aS)-6-methoxy-3,6,8,8-tetramethyloctahydro-1H-3a,7-methanoazulene; (3R,3aS,6R,7R,8aS)-3,6,8,8-tetramethyloctahydro-1H-3a,7-methanoazulen-3-yl formate; (3R,3aS,6R,7R,8aS)-3,6,8,8-tetramethyloctahydro-1H-3a,7-methanoazulen-6-yl acetate; (4Z,8Z)-1,5,9-trimethyl-13-oxabicyclo[10.1.0]trideca-4,8-diene; (3R,3aS,6R,7R,8aS)-3,6,8,8-tetramethyloctahydro-1H-3a,7-methanoazulen-6-ol; 5-methyl-1-(2,2,3-trimethylcyclopent-3-en-1-yl)-6-oxabicyclol[3.2.1]octane; 5-methyl-1-(2,2,3-trimethylcyclopent-3-en-1-yl)-6-oxabicyclo[3.2.1]octane; 1,1,2,3,3-pentamethyl-1,2,3,5,6,7-hexahydro-4H-inden-4-one; (Z)-4,11,11-trimethyl-8-methylenebicyclo[7.2.0]undec-3-en-5-yl acetate; (1S,2S,5R,8S)-4,4,8-trimethyltricyclol[6.3.1.02,5]dodecan-1-ol; 2-methyl-5-(prop-1-en-2-yl)cyclohex-2-en-1-yl acetate; octanenitrile; decanoic acid; decanal; 2,2-dimethyl-3-methylenebicyclol[2.2.1]heptane; ethyl 2-methyl-4-oxo-6-pentylcyclohex-2-ene-1-carboxylate; 2,6-di-tert-butyl-4-methylphenol; butyl stearate; butyl undec-10-enoate; 2-methyl-4-(2,2,3-trimethylcyclopent-3-en-1-yl)butan-1-ol; 3-(4-(tert-butyl)phenyl)propanal; (1S,2S)-1,7,7-trimethylbicyclo[2.2.1]heptan-2-yl isobutyrate; 1,7,7-trimethylbicyclo[2.2.1]heptan-2-yl acetate; 2-ethoxy-2,6,6-trimethyl-9-methylenebicyclo[3.3.1]nonane; (ethoxymethoxy)cyclododecane; (E)-1-methyl-4-(6-methylhept-5-en-2-ylidene)cyclohex-1-ene; 3,3,6,7-tetramethyloctahydro-2H-chromene; (5R,10R)-6,10-dimethyl-2-(propan-2-ylidene)spirol[4.5]dec-6-en-8-one; 1-methyl-4-(prop-1-en-2-yl)cyclohexyl acetate; (2Z,6E)-2,6-dimethyl-10-methylenedodeca-2,6,11-trienal; (R)-3-methylene-6-((S)-6-methylhept-5-en-2-yl)cyclohex-1-ene; (4aR,7R,8aS)-4a-methyl-1-methylene-7-(prop-1-en-2-yl)decahydronaphthalene; (Z)-2-methyl-5-((1S,2R,4R)-2-methyl-3-methylenebicyclo[2.2.1]heptan-2-yl)pent-2-en-1-ol; 6,6-dimethyl-2-methylenebicyclo[3.1.1]heptane; 2-ethoxynaphthalene; (1S,4R,7R)-1,4,9,9-tetramethyl-1,2,3,4,5,6,7,8-octahydro-4,7-methanoazulene; (1aS,5aR,9aR)-1a,5,5,7-tetramethyl-1a,2,3,4,5,5a,8,9-octahydrobenzo[1,7]cyclohepta[1,2]-b oxirene; (R)-3 5,5,9-tetramethyl-2,4a,5,6,7,8-hexahydro-1H-benzo[7]annulene; (1S,4S)-1,4-dimethyl-7-(propan-2-ylidene)-1,2,3,4,5,6,7,8-octahydroazulene; (E)-7,11-dimethyl-3-methylenedodeca-1,6,10-triene; (1R,2S,6S,7S,8S)-8-isopropyl-1-methyl-3-methylenetricyclo[4.4.0.02,7]decane; (3R,3aS,7S,8aS)-3,8,8-trimethyl-6-methyleneoctahydro-1H-3a,7-methanoazulene; (1R,9S,Z)-4,11,11-trimethyl-8-methylenebicyclo[7.2.0]undec-4-ene; (S)-4-methyl-1-((S)-6-methylhept-5-en-2-yl)cyclohex-3-en-1-ol; benzyl dodecanoate; benzyl cinnamate; benzyl benzoate; 2'-isopropyl-1,7,7-trimethylspiro[bicyclo[2.2.1]heptane-2,4'-[1,3]dioxane]; 4-(4-methylpent-3-en-1-yl)cyclohex-3-ene-1-carbonitrile; methyl (E)-2-((7-hydroxy-3,7-dimethyloctylidene)amino)benzoate; 4-methoxybenzyl 2-phenylacetate; pentyl (Z)-3-phenylacrylate; (3aR,5aS,9aS,9bR)-3a,6,6,9a-tetramethyldodecahydronaphtho[2,1-b]furan; (4aR,5R,7aS,9R)-2,2,5,8,8,9a-hexamethyloctahydro-4H-4a,9-methanoazuleno[5,6-d][1,3]dioxole; 2,5,5-trimethyl-1,2,3,4,5,6,7,8-octahydronaphthalen-2-ol; 2,5,5-trimethyl-1,2,3,4,4a,5,6,7-octahydronaphthalen-2-ol; 1-((2-(tert-butyl)cyclohexyl)oxy)butan-2-ol; (3S,5aR,7aS,11aS,11bR)-3,8,8,11a-tetramethyldodecahydro-5H-3,5a-epoxynaphtho[2,1-c]oxepine; 2,2,6,6,7,8,8-heptamethyldecahydro-2H-indeno[4,5-b]furan; 2,2,7,7,8,9,9-heptamethyldecahydroindeno[4,3a-b]furan; 2-(sec-butyl)-1-vinylcyclohexyl acetate; (4R,4aS)-4,4a-dimethyl-6-(propan-2-ylidene)-4,4a,5,6,7,8-hexahydronaphthalen-2(3H)-one; 2-(4-methylcyclohex-3-en-1-yl)propan-2-yl propionate; (2Z,6E,9E)-2,6,10-trimethyldodeca-2,6,9,11-tetraenal; (2R,4aR,8aR)-4a,8-dimethyl-2-(prop-1-en-2-yl)-1,2,3,4,4a,5,6,8a-octahydronaphthalene; 1,7-dimethyl-7-(4-methylpent-3-en-1-yl)tricyclo[2.2.1.02,6]heptane; (E)-5-(2,3-dimethyltricyclo[2.2.1.02,6]heptan-3-yl)-2-methylpent-2-en-1-ol; (1R,3aS,7S,8aR)-1,4,9,9-tetramethyl-2,3,6,7,8,8a-hexahydro-1H-3a,7-methanoazulene; 1-(5,5-dimethylcyclohex-1-en-1-yl)pent-4-en-1-one; (1S,4aS,8aR)-1-isopropyl-4,7-dimethyl-1,2,4a,5,6,8a-hexahydronaphthalene; (R,Z)-1(2,6,6-trimethylcyclohex-2-en-1-yl)pent-1-en-3-one; 1-methyl-4-(prop-1-en-2-yl)cyclohex-1-ene; (Z)-4-(2,5,6,6-tetramethylcyclohex-2-en-1-yl)but-3-en-2-one; (1Z,4E,8Z)-2,6,6,9-tetramethylcycloundeca-1,4,8-triene; (4aR,8S,9aS)-3,5,5,8tetramethyl-9-methylene-2,4a,5,6,7,8,9,9a-octahydro-1H-benzo[7]annulene; (1aR,4R,4aR,7bS)-1,1,4,7-tetramethyl-1a,2,3,4,4a,5,6,7b-octahydro-1H-cyclopropa[e]azulene; 1,4-dimethyl-7-(prop-1-en-2-yl)-1,2,3,4,5,6,7,8-octahydroazulene; (3E,6E)-3,7,11-trimethyldodeca-1,3,6,10-tetraene; 7,7-dimethyl-2-methylenebicyclo[2.2.1]heptane; 2-((2R,4aR,8aR)-4a,8-dimethyl-1,2,3,4,4a,5,6,8a-octahydronaphthalen-2-yl)propan -2-ol; (R)-1-methyl-4-(6-methylhept-5-en-2-yl)benzene; (3aR,3bR,4S,7R,7aS)-4-isopropyl-7-methyl-3a,3b,4,5,6,7-hexahydro-1H-cyclopenta[1,3]cyclopropa[1,2]benzene; (1aS,2aR,3R,5aS,7R,7aR)-3,6,6,7a-tetramethyloctahydro-2H-2a,7-methanoazuleno[5,6-b]oxirene; (1R,4S,4aR,8aR)-4-isopropyl-1,6-dimethyl-1,2,3,4,4a,7,8,8a-octahydronaphthalen-1-ol; (1S,4aR,8aR)-1-isopropyl-4,7-dimethyl-1,2,4a,5 6,8a-hexahydronaphthalene; (R)-2-((R)-4-methylcyclohex-3-en- 1-yl)hex-5-en-2-ol; (Z)-1-methyl-4-(6-methylhepta-2,5-dien-2-yl)cyclohex-1-ene; 2,6-dimethyl-6-(4-methylpent-3-en-1-yl)bicyclo[3.1.1]hept-2-ene; (E)-2-benzylideneheptan-1-ol; (E)-2-benzylideneheptyl acetate; (Z)-(2-(diethoxymethyl)hept-1-en-1-yl)benzene; (E)-2-benzylideneheptanal; (1S,4aR,8aS)-1-isopropyl-4,7-dimethyl-1,2,4a,5,6,8a-hexahydronaphthalene; (3R,5aS,9aR)-2,2,5a,9-tetramethyl-3,4,5,5a,6,7-hexahydro-2H-3,9a-methanobenzo[b]oxepine; 1-methyl-4-(4-methylpent-3-en-1-yl)cyclohex-3-ene-1-carbaldehyde; 3-methyl-1-phenylpentan-3-ol; 2,6,10-trimethylundecanal; allyl 3-cyclohexylpropanoate; (1aR,4aS,7R,7aR,7bS)-1,1,7-trimethyl-4-methylenedecahydro-1H-cyclopropa[e]azulene; (E)-undec-9-enal; methyl (E)-2-(((3,5-dimethylcyclohex-3-en-1-yl)methylene)amino)benzoate; 2,6,10-trimethylundec-9-enal; (7,7,8,8-tetramethyloctahydro-2,3b-methanocyclopenta[1,3]cyclopropa[1,2]benzen-4-yl)methyl acetate; nonyl acetate; (2-(1-propoxyethoxy)ethyl)benzene; (Z)-2-(4-methylbenzylidene)heptanal; dec-9-enal; (Z)-oxacycloheptadec-8-en-2-one; (2S,4aR,8aR)-4a,8-dimethyl-2-(prop-1-en-2-yl)-1,2,3,4,4a,5,6,8a-octahydronaphthalene; 2-((2S,4aR,8aR)-4a,8-dimethyl-1,2,3,4,4a,5,6,8a-octahydronaphthalen-2-yl)propan-2-ol; 1-(3,5,5,6,8,8-hexamethyl-5,6,7,8-tetrahydronaphthalen-2-yl)ethan-1-one; 6-isopropylquinoline; 3-(6,6-dimethylbicyclo[3.1.1]hept-2-en-2-yl)propanal; 6,10,14-trimethylpentadecan-2-one; (E)-cyclohexadec-5-en-1-one; 1-isopropyl-4-methylcyclohex-3-en-1-ol; 1-isopropyl-4-methylcyclohex-3-en-1-ol; 3,6-dimethyl-4,5,6,7-tetrahydrobenzofuran; (1aR,2S,4aS)-2,4a,8,8-tetramethyloctahydrocyclopropa[d]naphthalen-3(1H)-one; (Z)-dodec-2-enal; (E)-hex-3-en-1-yl 3-methylbutanoate; 3,6-dimethyloctan-3-yl acetate; 3-(4-isopropylphenyl)propanal; (Z)-undec-2-enenitrile; (E)-undec-2-enal; phenethyl butyrate; (Z)-non-2-enal; nonan-2-ol; nonan-2-one; 2-isobutylquinoline; (E)-2-hexylidenecyclopentan-1-one; 2-heptyltetrahydrofuran; (E)-dec-2-enal; 2,6-dimethyloctanal; decan-1-ol; (E)-hept-1-en-1-yl acetate; undec-10-en-1-ol; undec-10-enal; 2-((2R,4aS)-4a,8-dimethyl-1,2,3,4,4a,5,6,7-octahydronaphthalen-2-yl)propan-2-ol; 1-isopropyl-4-methyl-7-thiabicyclo[2.2.1]heptane; (3E,5Z)-undeca-1,3,5-triene; 3,7-dimethyloct-6-en-3-ol; 1,3,3-trimethylbicyclo[2.2.1]heptan-2-yl acetate; 1,1,2,3,3-pentamethyl-2,3-dihydro-1H-indene; (Z)-6,10-dimethylundeca-5,9-dien-2-yl acetate; (Z)-dodec-3-enal; (S)-5-heptyldihydrofuran-2(3H)-one; (R)-5-heptyldihydrofuran-2(3H)-one; (E)-6,10-dimethylundeca-5,9-dien-2-yl acetate; (Z)-3-methyl-5-phenylpent-2-enenitrile; (2S,5S,6S)-2,6,10,10-tetramethyl-1-oxaspiro[4.5]decan-6-ol; (2E)-3-methyl-5-phenyl-2-pentenenitrile; (2S,5R)-2-isopropyl-5-methylcyclohexan-1-one; (R,E)-2-methyl-4-(2,2,3-trimethylcyclopent-3-en-1-yl)but-2-en-1-ol; 2-(8-isopropyl-6-methylbicyclo[2.2.2]oct-5-en-2-yl)-1,3-dioxolane; (E)-4-(2,2-dimethyl-6-methylenecyclohexyl)-3-methylbut-3-en-2-one; 3-(3-isopropylphenyl)butanal; 3-(1-ethoxyethoxy)-3,7-dimethylocta-1,6-diene; 3a,4,5,6,7,7a-hexahydro-1H-4,7-methanoinden-6-yl propionate; 2-((3S,3aS,5R)-3,8-dimethyl-1,2,3,3a,4,5,6,7-octahydroazulen-5-yl)propan-2-ol; benzyl 2-phenylacetate; 3-(6,6-dimethylbicyclo[3.1.1]hept-2-en-2-yl)-2,2-dimethylpropanal; 2-methyl-5-(6-methylhept-5-en-2 -yl)bicyclo[3.1.0]hex-2-ene; 1-(1,1,2,3,3,6-hexamethyl-2,3-dihydro-1H-inden-5-yl)ethan-1-one; (E)-tridec-2-enal; (1R,4S,4aS,6R,8aS)-4,8a,9,9-tetramethyloctahydro-1,6-methanonaphthalen-1(2H)-ol; p-tolyl hexanoate; 5-hexyl-4-methyldihydrofuran-2(3H)-one; ethyl (2Z,4E)-deca-2,4-dienoate; 2,4-dimethyl-6-phenyl-3,6-dihydro-2H-pyran; 2-cyclohexylidene-2-phenylacetonitrile; (4-(prop-1-en-2-yl)cyclohex-1-en-1-yl)methyl acetate; (4-(prop-1-en-2-yl)cyclohex-1-en-1-yl)methanol; 2-isopropoxyethyl)benzene; 2-cyclohexylhepta-1,6-dien-3-one; (2-(cyclohexyloxy)ethyl)benzene; phenethyl 2-methylbutanoate; phenethyl 2-phenylacetate; phenyl benzoate; phenethyl benzoate; 2-(6,6-dimethylbicyclo[3.1.1]hept-2-en-2-yl)acetaldehyde; 3a,4,5,6,7,7a-hexahydro-1H-4,7-methanoinden-6-yl pivalate; (E)-3 3-dimethyl-5-(2,2,3-trimethylcyclopent-3-en-1-yl)pent-4-en-2-ol; 1-methyl-4-(4-methylpent-3-en-1-yl)cyclohex-3-ene-1-carbaldehyde; p-tolyl 2-phenylacetate; Ethyl 2,4,7-decatrienoate; 2-benzyl-4,4,6-trimethyl-1,3-dioxane; 2,4-dimethyl-4-phenyltetrahydrofuran; (2R,4a'R,8a'R)-3,7'-dimethyl-3',4',4a',5',8',8a'-hexahydro-1'H-spiro[oxirane-2,2'-[1,4]methanonaphthalene]; (Z)-6-ethylideneoctahydro-2H-5,8-methanochromene; 2-((S)-1-((S)-3,3-dimethylcyclohexyl)ethoxy)-2-oxoethyl propionate; methyl 2,2-dimethyl-6-methylenecyclohexane-1-carboxylate; 4-methyl-2-phenyl-3,6-dihydro-2H-pyran; 2,2,7,9-tetramethylspiro(5.5)undec-8-en-1-one; 3-methyl-5-(2,2,3-trimethylcyclopent-3-en-1-yl)pentan-2-ol; (Z)-2-ethyl-4-(2,2,3-trimethylcyclopent-3-en-1-yl)but-2-en-1-ol; (E)-2-methyl-4-(2,2,3-trimethylcyclopent-3-en-1-yl)but-2-en-1-ol; 1-(3-hydroxy-3-methylpent-4-en-1-yl)-2,5,5,8a-tetramethyldecahydronaphthalen-2-ol; (4aR,6aS,10aS,10bR)-3,4a,7,7,10a-pentamethyl-4a,5,6,6a,7,8,9,10,10a,10b-decahydro-1H-benzo[f]chromene; (4aR,8aR)-4a,8-dimethyl-2-(propan-2-ylidene)-1,2,3,4,4a,5,6,8a-octahydronaphthalene; 2-(1-(3,3-dimethylcyclohexyl)ethoxy)-2-methylpropyl cyclopropanecarboxylate; 3-(4-isobutylphenyl)-2-methylpropanal; (1aR,4aR,7S,7aR,7bR)-1,1,7-trimethyl-4-methylenedecahydro-1H-cyclopropa[e]azulen-7-ol; 1-(spiro[4.5]dec-7-en-7-yl)pent-4-en-1-one; (Z)-dodec-4-enal; (1S,4S,4aR,8aR)-4-isopropyl-1,6-dimethyl-1,2,3,4,4a,7,8,8a-octahydronaphthalen-1-ol; (1S,4S,4aR,8aS)-4-isopropyl-1,6-dimethyl-1,2,3,4,4a,7,8,8a-octahydronaphthalen-1-ol; 3-methyl-2-pentylcyclopentan-1-one; 2,6,10,10-tetramethyl-1-oxaspiro[4.5]dec-6-ene; (1aR,4aS)-2,4a,8,8-tetramethyl-1,1a,4,4a,5,6,7,8-octahydrocyclopropa[d]naphthalene; 1-isopropyl-2-methoxy-4-methylbenzene; 1-(2,2,6-trimethylcyclohexyl)hexan-3-ol; (2E,6E)-3,7,11-trimethyldodeca-2,6,10-trien-1-ol; (Z)-dec-2-enal; (E)-non-2-enal; (E)-dec-4-enal; (Z)-oxacycloheptadec-8-en-2-one; (Z)-3,7-dimethylocta-1,3,6-triene; (Z)-3,7-dimethylocta-1,3,6-triene; (E)-3,7-dimethylocta-2,6-dien-1-ol; (1R-(1alpha,3alpha,4aalpha))-2,3,4,4a,5,6-hexahydro-2,2-dimethyl-1,3-methanonaphthalen-7(1H)-one; tridecan-1-ol; methyl 2-((1-hydroxy-3-phenylbutyl)amino)benzoate; 1-((2E,5Z,9Z)-2,6,10-trimethylcyclododeca-2,5,9-trien-1-yl)ethan-1-one; decahydro-2,6,6,7,8,8-hexamethyl-2h-indeno(4,5-b)furan; pentamethyl octahydroindenodioxane; undecanal; (E)-4-methyldec-3-en-5-ol; (3R,4aS,5R)-4a,5-dimethyl-3-(prop-1-en-2-yl)-1,2,3,4,4a,5,6,7-octahydronaphthalene; 2-((2R,8R,8aS)-8,8a-dimethyl-1,2,3,4,6,7,8,8a-octahydronaphthalen-2-yl)propan-2-ol; (Z)-2-methyl-4-(2,6,6-trimethylcyclohex-2-en-1-yl)but-2-enal; 1-methoxy-3a,4,5,6,7,7a-hexahydro-1H-4,7-methanoindene; methyl (Z)-2-((3-(4-(tert-butyl)phenyl)-2-methylpropylidene)amino)benzoate; 2,4,6-trimethyl-4-phenyl-1,3-dioxane; 1-((3R,3aR,7R,8aS)-3,6,8,8-tetramethyl-2,3,4,7,8,8a-hexahydro-1H-3a,7-methanoazulen-5-yl)ethan-1-one; methyl (Z)-2-(((2,4-dimethylcyclohex-3-en-1-yl)methylene)amino)benzoate; 4,8-dimethyl-2-(propan-2-ylidene)-1,2,3,3a,4,5,6,8a-octahydroazulen-6-ol; 4,8-dimethyl-2-(propan-2-ylidene)-1,2,3,3a,4,5,6,8a-octahydroazulen-6-yl acetate; decahydro-3H-spiro[furan-2,5'-[4,7]methanoindene]; (2Z,6E)-nona-2,6-dienenitrile; (1aR,4S,4aS,7R,7aS,7bS)-1,1,4, 7-tetramethyldecahydro-1H-cyclopropa[e]azulen-4-ol; 3,5,5,6,7,8,8-heptamethyl-5,6,7,8-tetrahydronaphthalene-2-carbonitrile; (1S,2S,3S,5R)-2,6,6-trimethylspiro[bicyclo[3.1.1]heptane-3,1'-cyclohexan]-2'-en-4'-one; 1',1',5',5'-tetramethylhexahydro-2'H,5'H-spiro[[1,3]dioxolane-2,8'-[2,4a]methanonaphthalene]; (2'S,4a'S,8a'S)-1',1',5',5'-tetramethylhexahydro-2'H,5'H-spiro[[1,3]dioxolane-2,8'-[2,4a]methanonaphthalene]; (1R,8aR)-4-isopropyl-1,6-dimethyl-1,2,3,7,8,8a-hexahydronaphthalene; (7,7,8,8-tetramethyloctahydro-2,3b-methanocyclopenta[1,3]cyclopropa[1,2]benzen-4-yl)methanol; 1-ethoxy-4-(tert-pentyl)cyclohexane; (3Z)-1-(2-buten-1-yloxy)-3-hexene; 4-(2-methoxypropan-2-yl)-1-methylcyclohex-1-ene; 3-methoxy-3,7-dimethylocta-1,6-diene; 3,7-dimethyloctanal; hexyl 2-hydroxybenzoate; hexyl (Z)-but-2-enoate; (Z)-3,7-dimethylocta-2,6-dien-1-yl formate; (Z)-1-(2,6,6-trimethylcyclohex-1-en-1-yl)pent-1-en-3-one; (E)-3,7-dimethylocta-4,6-dien-3-ol; methyl (Z)-3,7-dimethylocta-2,6-dienoate; ((1s,4s)-4-isopropylcyclohexyl)methanol; 3,7-dimethylocta-1,6-dien-3-yl propionate; 3,7-dimethylocta-1,6-dien-3-yl formate; 3,7-dimethylocta-1,6-dien-3-yl butyrate; 3,7-dimethylocta-1,6-dien-3-yl acetate; 3,7-dimethylocta-1,6-dien-3-ol; 2,2-dimethyl-5-phenylhexanenitrile; (Z)-4-(6,6-dimethylcyclohex-2-en-1-yl)-3-methylbut-3-en-2-one; 7-methyloctyl acetate; isopentyl octanoate; hexyl propionate; hexyl butyrate; hexyl 2-methylbutanoate; hexyl furan-2-carboxylate; heptyl acetate; (Z)-3,7-dimethylocta-2,6-dienenitrile; (E)-3,7-dimethylocta-2,6-dien-1-yl formate; (E)-3,7-dimethylocta-2,6-dien-1-yl octanoate; (E)-3,7-dimethylocta-2,6-dien-1-yl benzoate; (E)-3,7-dimethylocta-2,6-dienal; 1-isopropyl-4-methylcyclohexa-1,4-diene; 2-(sec-butyl)cyclohexan-1-one; 3-(2-ethylphenyl)-2,2-dimethylpropanal; 2-(tert-butyl)cyclohexyl ethyl carbonate; ethyl octanoate; ethyl 2-cyclohexylpropanoate; 4-methyl-2-phenyltetrahydro-2H-pyran; 2,6-dimethyloct-7-en-2-ol; 3-methyl-2-pentylcyclopent-2-en-1-one; 2-(4-methylcyclohexyl)propan-2-yl acetate; 4-(2,6,6-trimethylcyclohex-2-en-1-yl)butan-2-one; (oxybis(methylene))dibenzene; dibutyl phthalate; decyl 2-aminobenzoate; methyl (1s,4s)-1,4-dimethylcyclohexane-1-carboxylate; 2-cyclohexylethyl acetate; (3Z,5Z)-2,6-dimethylocta-1,3,5,7-tetraene; 4-cyclohexyl-2-methylbutan-2-ol; 2-benzyl-2-methylbut-3-enenitrile; 3,7-dimethyloct-6-enenitrile; 3,7-dimethyloct-6-en-1-yl 2-phenylacetate; 3,7-dimethyloct-6-en-1-yl formate; 3,7-dimethyloct-6-en-1-yl benzoate; 3,7-dimethyloct-6-en-1-ol; 3,7-dimethyloct-6-enal; (E)-3,7-dimethylocta-2,6-dienal; (1R,2S,5R)-2,6,6-trimethylbicyclol[3.1.1]heptane; (Z)-hex-3-en-1-yl pentanoate; (E)-hex-3-en-1-yl (E)-2-methylbut-2-enoate; (Z)-hex-3-en-1-yl butyrate; 4-chloro-3,5-dimethylphenol; 5-isopropyl-2-methylphenol; (E)-2-methyl-4-(2,6,6-trimethylcyclohex-1-en-1-yl)but-2-enal; 3-isopropyl-6-methylenecyclohex-1-ene; benzyl 2-hydroxybenzoate; benzyl 3-methylbutanoate; 1-(3,3-dimethylcyclohexyl)ethyl formate; (Z)-1-methoxy-4-(prop-1-en-1-yl)benzene; pentyl benzoate; 2-(4-methylcyclohex-3-en-1-yl)propan-2-yl acetate; (Z)-3-methyl-4-(2,6,6-trimethylcyclohex-2-en-1-yl)but-3-en-2-one; (2-(allyloxy)ethyl)benzene; allyl heptanoate; 6,8-dimethylnonan-2-ol; -methyl-5-phenylhexan-3-one; 3,7-dimethyl-2-methyleneoct-6-enal; 3,7-dimethyloctan-1-ol; 2-pentylcyclopentan-1-ol; (2S,4S)-2-heptyl-2,4-dimethyl-1,3-dioxolane; (E)-2-isopropyl-5-methylhex-2-enal; 1-isopropyl-4-methyl-7-oxabicyclo[2.2.1]heptane; (Z)-1-(2,6,6-trimethylcyclohex-2-en-1-yl)but-2-en-1-one; (R)-3,7-dimethylocta-1,6-dien-3-ol;3 7-dimethyloct-6-enal; (R)-3,7-dimethyloct-6-enal; 3,7-dimethyloct-6-en-1-ol; 3,7-dimethyloct-6-en-1-ol; (1R,5R)-2,6,6-trimethylbicyclo[3.1.1]hept-2-ene; (1S,5S)-2,6,6-trimethylbicyclo[3.1.1]hept-2-ene; hexyl (Z)-2-methylbut-2-enoate; p-cymene; phenethyl isobutyrate; phenethyl (Z)-2-methylbut-2-enoate; phenethyl methacrylate; (2Z,5Z)-5,6,7-trimethylocta-2,5-dien-4-one; 1-methoxy-4-propylbenzene; 2-(4-(tert-butyl)phenyl)acetaldehyde; 4-(tert-pentyl)cyclohexan-1-ol; 2,6,6-trimethylbicyclo[3.1.1]hept-2-ene; ethyl (2,3,6-trimethylcyclohexyl) carbonate; 1-(3,3-dimethylcyclohexyl)ethyl acetate; (S)-3,7-dimethylocta-1,6-dien-3-ol; 1-isopropyl-4-methylenebicyclo[3.1.0]hexane; 3,7-dimethyloctanal; 4-(2,2,6-trimethylcyclohexyl)butan-2-ol; 3,7-dimethyloctan-3-ol; 3,7-dimethyloctan-3-yl acetate; ethyl (1R,6S)-2,2,6-trimethylcyclohexane-1-carboxylate; 2-isopropyl-5-methylphenol; (Z)-1-(2,6,6-trimethylcyclohex-2-en-1-yl)but-2-en-1-one; (Z)-1-methoxy-4-(prop-1-en-1-yl)benzene; 2,2,2-trichloro-1-phenylethyl acetate; 2,2,5-trimethyl-5-pentylcyclopentan-1-one; (4-tert-butylcyclohexyl) acetate; 4-(tert-butyl)cyclohexyl acetate; 4-methyl-4-phenylpentan-2-yl acetate; (Z)-1-((2-methylallyl)oxy)hex-3-ene; 4,5-epoxy-4,11,11-trimethyl-8-methylenebicyclo(7.2.0)undecane; 1,3,4,6,7,8alpha-hexahydro-1,1,5,5-tetramethyl-2H-2,4alpha-methanophtalen-8(5H)-one, and mixtures thereof.

16. The composition according to claim 1, wherein said malodor reduction materials are not selected from the group consisting of geranyl nitrile; helional; nonanal; linalool; (S)-(+)-linalool; (R)-(−)-linalool; nerol; tetrahydrolinalool; 2-phenylethyl acetate; eugenol; ethyl linalool; allyl heptoate; agrumen nitrile; citronitrile; 2,2-dimethyl-3-(m-tolyl)propan-1-ol; 2-methyl-5-phenylpentan-1-ol; dodecanenitrile; 2-heptylcyclopentan-1-one; methyl nonyl acetaldehyde; 3-(2-ethylphenyl)-2,2-dimethylpropanal; (Z)-1-(2,6,6-trimethylcyclohex-2-en-1-yl)but-2-en-1-one; (R,E)-2-methyl-4-(2,2,3 -trimethylcyclopent-3-en-1-yl)but-2-en-1-ol; 4-(tert-butyl)cyclohexyl acetate; 1-cyclohexylethyl (E)-but-2-enoate; allyl 2-(cyclohexyloxy)acetate; alpha terpinyl acetate; beta terpinyl acetate; gamma terpinyl acetate; methyl dodecyl ether; 2,4-dimethyl-4,4a,5,9b-tetrahydroindeno[1,2-d][1,3]dioxine; cinnamyl isobutyrate; (E)-2-methyl-4-(2,6,6-trimethylcyclohex-1-en-1-yl)but-2-enal; gamma methyl ionone; ethyl 2,3,6-trimethyl cyclohexyl carbonate ethyl 2,3,6-trimethyl cyclohexyl carbonate; Citral diethyl acetal; Dimethoxycyclododecane; 1-((2S,3S)-2,3,8,8-tetramethyl-1,2,3,4,5,6,7,8-octahydronaphthalen-2-yl)ethan-1-one; oxacyclohexadecan-2-one; 4,6,6,7,8,8-hexamethyl-1,3,4,6,7,8-hexahydrocyclopentalglisochromene; Ethylene brassylate; Methyl (Z)-2-((3-(4-(tert-butyl)phenyl)-2-methylpropylidenelamino)benzoate; 4,7-Methano-1H-inden-5-ol, 3a,4,5,6,7,7a-hexahydro-, 5-acetate; cedryl methyl ether; vetivert acetate; 1-((3R,3aR,7R,8aS)-3,6,8,8-tetramethyl-2,3,4,7,8,8a-hexahydro-1H-3a,7-methanoazulen-5-yl)ethan-1-one; Benzophenone; Farnesol; trans,trans-farnesol; 3-(3-isopropylphenyl)butanal; 2,6,10-trimethylundec-9-enal; 3-(4-(tert-butyl)phenyl)propanal; 3-(4-isopropylphenyl)-2-methylpropanal; Citronellal (1); Citronellal (d); (E)-4,8-dimethyldeca-4,9-dienal; Pino Acetaldehyde; 3-(4-(tert-butyl)phenyl)-2-methylpropanal; Cinnamic aldehyde; Citral; Geranial; MethoxyMelonal; o-methoxycinnamaldehyde; (E)-4-((3aS,7aS)-octahydro-5H-4,7-methanoinden-5-ylidene)butanal; Methyl Octyl Acetaldehyde; 3-(4-methoxyphenyl)-2-methylpropanal; 5-methoxyoctahydro-1H-4,7-methanoindene-2-carbaldehyde; Iso Cyclocitral; Octanal; 2-Undecenal; 10-Undecenal; Trans -trans-2,6-Nonadienal; Trans-2, cis-6-nondienal; Heliotropin; Hexyl Cinnamic aldehyde; p-methyl-alpha-pentylcinnamaldehyde; Alpha-methyl cinnamaldehyde; 3,4-dimethoxybenzaldehyde; Myrtenal; Perillaldehyde; Maceal; Methyl palmitate; Methyl iso eugenol; and mixtures thereof.

17. The composition according to claim 1, wherein said composition comprises from about 0.005% to about 10% of said malodor agent, wherein said malodor agent comprises from about 1 to about 30 malodor reduction materials having a Blocker Index of 3 to about 0.001, wherein at least a portion of said malodor reduction materials are encapsulated.

18. A process for treating a laundry article using the composition according to claim 1 comprising the steps of:

providing about 1 mg to about 100 g of said particles in a washing machine or laundry wash basin; and washing said laundry article in a wash liquor in said washing machine or laundry wash basin into which said particles are dissolved.

19. A process for reducing malodor from a laundry article using the composition according to claim 1 comprising the steps of:

providing about 1 mg to about 100 g of said particles in a fluid pervious package; and placing said package proximal to said laundry article or contacting said laundry article with said fluid pervious package.

* * * * *